(12) United States Patent
Beswick et al.

(10) Patent No.: US 7,199,239 B2
(45) Date of Patent: Apr. 3, 2007

(54) CHEMICAL COMPOUNDS

(75) Inventors: Paul John Beswick, Stevenage (GB); John David Harling, Harlow (GB); Savvas Kleanthous, Stevenage (GB); Millard Hurst Lambert, III, Durham, NC (US); Vipulkumar Kantibhai Patel, Stevenage (GB); Juliet Simpson, Stevenage (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 14 days.

(21) Appl. No.: 10/518,778

(22) PCT Filed: Jun. 18, 2003

(86) PCT No.: PCT/EP03/06416

§ 371 (c)(1), (2), (4) Date: Dec. 17, 2004

(87) PCT Pub. No.: WO04/000762

PCT Pub. Date: Dec. 31, 2003

(65) Prior Publication Data

US 2006/0074111 A1  Apr. 6, 2006

(30) Foreign Application Priority Data

Jun. 20, 2002 (GB) .................. 0214254.5

(51) Int. Cl.
*C07D 211/70* (2006.01)
*C07D 239/02* (2006.01)
*C07D 241/04* (2006.01)
*C07C 69/74* (2006.01)

(52) U.S. Cl. .............. 544/297; 544/382; 546/342; 560/126

(58) Field of Classification Search .......... 546/342; 544/297, 382; 514/275, 252.12; 560/126
See application file for complete search history.

(56) References Cited

U.S. PATENT DOCUMENTS 3,912,756 A  10/1975  Wolff et al.
4,214,094 A * 7/1980  Kamiya et al. ........... 560/42

FOREIGN PATENT DOCUMENTS

| FR | 2273518 | 1/1976 |
| WO | WO 00/23407 | 4/2000 |
| WO | 1067109 | 1/2001 |
| WO | WO 02/28821 | 4/2002 |

OTHER PUBLICATIONS

Hcaplus 68:49243.*
Hcaplus 86:55153.*

* cited by examiner

*Primary Examiner*—Thomas McKenzie
*Assistant Examiner*—Binta Robinson
(74) *Attorney, Agent, or Firm*—Jennifer L. Fox

(57) ABSTRACT

A compound of formula (I) or a pharmaceutically acceptable salt, solvate, or hydrolysable ester thereof,

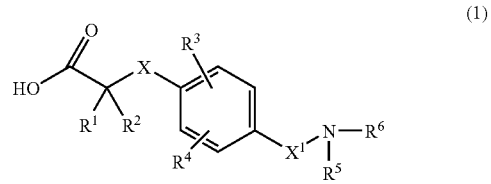

Wherein:
$R^1$ and $R^2$ are independently hydrogen or $C_{1-3}$ alkyl;
X represents a bond, $CH_2$ or O;
$R^3$ and $R^4$ are independently hydrogen, $C_{1-6}$ alkyl, $OCH_3$, $CF_3$, allyl or halogen;
$X^1$ is $CH_2$, $SO_2$, or CO;
$R^5$ is —$C_{1-6}$ alkyl (optionally substituted by $C_{1-6}$alkoxy or $C_{1-6}$alkylthio), —$C_{2-6}$ alkenyl, —$C_{0-6}$ alkyl phenyl (wherein the phenyl is optionally substituted by one or more $CF_3$, halogen, $C_{1-3}$ alkyl, $C_{1-3}$ alkoxy), —$COC_{1-6}$ alkyl, $SO_2C_{1-6}$ alkyl;
$R^6$ is phenyl or a 6 membered heteroaryl group containing 1, 2 or 3 N atoms wherein the phenyl or heteroaryl group is optionally substituted with 1, 2 or 3 moieties selected from the group consisting of $C_{1-6}$ alkyl, halogen, —$OC_{1-6}$ alkyl, —$SO_2C_{1-3}$ alkyl, phenyl (optionally substituted by one or more groups selected from halogen, $CF_3$, $C_{1-3}$ alkyl, $OC_{1-3}$ alkyl, acetyl, CN).

12 Claims, No Drawings

CHEMICAL COMPOUNDS

This application is filed pursuant to 35 U.S.C. § 371 as a United States National Phase Application of International Application No. PCT/EP03/006416 filed Jun. 18, 2003, which claims priority from 0214254.5 GB filed Jun. 20, 2002

The present invention relates to certain novel compounds. In particular, the present invention relates to compounds that activate human peroxisome proliferator activated receptors ("hPPARs"). The present invention also relates to method for preparing the compounds, their use in medicine, pharmaceutical compositions containing them and methods for the prevention or treatment of PPAR mediated diseases or conditions.

Several independent risk factors have been associated with cardiovascular disease. These include hypertension, increased fibrinogen levels, high levels of triglycerides, elevated LDL cholesterol, elevated total cholesterol, and low levels of HDL cholesterol. HMG CoA reductase inhibitors ("statins") are useful for treating conditions characterized by high LDL-c levels. It has been shown that lowering LDL-c is not sufficient for reducing the risk of cardiovascular disease in some patients, particularly those with normal LDL-c levels. This population pool is identified by the independent risk factor of low HDL-c. The increased risk of cardiovascular disease associated with low HDL-c levels has not yet been totally successfully addressed by drug therapy (Bisgaier, C. L.; Pape, M. E. Curr. Pharm. Des. 1998, 4, 53–70).

Syndrome X (including metabolic syndrome) is loosely defined as a collection of abnormalities including hyperinsulemia, obesity, elevated levels of the following:—triglycerides, uric acid, fibrinogen, small dense LDL particles, and plasminogen activator inhibitor 1 (PAI-1), and decreased levels of HDL-c.

NIDDM is described as insulin resistance, which in turn causes anomalous glucose output and a decrease in glucose uptake, by skeletal muscle. These factors eventually lead to impaired glucose tolerance (IGT) and hyperinsulinemia.

Peroxisome Proliferator Activated Receptors (PPARs) are orphan receptors belonging to the steroid/retinoid receptor superfamily of ligand-activated transcription factors. See, for example Willson T. M. and Wahli, W., Curr. Opin. Chem. Biol., 1, pp 235–241 (1997) and Willson T. M. et. al., J. Med. Chem., 43, p 527–549 (2000). The binding of agonist ligands to the receptor results in changes in the expression level of mRNAs encoded by PPAR target genes.

Three mammalian Peroxisome Proliferator Activated Receptors have been isolated and termed PPAR alpha, PPAR gamma, and PPAR delta (also known as NUC1 or PPAR beta). These PPARs regulate expression of target genes by binding to DNA sequence elements, termed PPAR response elements (PPRE). To date, PPREs have been identified in the enhancers of a number of genes encoding proteins that regulate lipid metabolism suggesting that PPARs play a pivotal role in the adipogenic signalling cascade and lipid homeostasis (H. Keller and W. Wahli, Trends Endocrinol. Metab 291–296, 4 (1993)).

It has now been reported that the thiazolidinedione class of drugs are potent and selective activators of PPAR gamma and bind directly to the PPAR gamma receptor (J. M. Lehmann et. al., J. Biol. Chem. 12953–12956, 270 (1995)), providing evidence that PPAR gamma is a possible target for the therapeutic actions of the thiazolidinediones.

Activators of the nuclear receptor $PPAR_\gamma$, for example rosiglitazone, have been shown in the clinic to enhance insulin-action, reduce serum glucose and have small but significant effects on reducing serum triglyceride levels in patients with Type 2 diabetes. See, for example, D. E. Kelly et al., Curr. Opin. Endocrinol. Diabetes, 90–96, 5 (2), (1998); M. D. Johnson et al., Ann. Pharmacother., 337–348, 32 (3), (1997); and M. Leutenegger et al., Curr. Ther. Res., 403–416, 58 (7), (1997).

The mechanism for this triglyceride lowering effect appears to be predominantly increased clearance of very low density lipoproteins (VLDL) through induction of lipoprotein lipase (LPL) gene expression. See, for example, B. Staels et al., Arterioscler. Thromb., Vasc. Biol., 1756–1764, 17 (9), (1997).

Fibrates are a class of drugs which may lower serum triglycerides 20–50%, lower LDLc 10–15%, shift the LDL particle size from the more atherogenic small dense to normal dense LDL, and increase HDLc 10–15%. Experimental evidence indicates that the effects of fibrates on serum lipids are mediated through activation of PPARα. See, for example, B. Staels et al., Curr. Pharm. Des., 1–14, 3 (1), (1997). Activation of PPARα results in transcription of enzymes that increase fatty acid catabolism and decrease de-novo fatty acid synthesis in the liver resulting in decreased triglyceride synthesis and VLDL production/secretion. In addition, PPARα activation decreases production of apoC-III. Reduction in apoC-III, an inhibitor of LPL activity, increases clearance of VLDL. See, for example, J. Auwerx et al., Atherosclerosis, (Shannon, Irel.), S29–S37, 124 (Suppl), (1996).

Certain compounds that activate or otherwise interact with one or more of the PPARs have been implicated in the regulation of triglyceride and cholesterol levels in animal models. See, for example, U.S. Pat. No. 5,847,008 (Doebber et al.) and U.S. Pat. No. 5,859,051 (Adams et al.) and PCT publications WO 97/28149 (Leibowitz et al.), WO99/04815 (Shimokawa et al.) and WO01/00603 (Glaxo Group Ltd). Oliver et al Proc Natl Acad Sci 98, 5306–5311 (2001) reports raising of HDLc and lowering of serum triglycerides in the obese rhesus monkey following administration of a PPAR delta agonist.

Accordingly the invention provides a compound of formula (I) and pharmaceutically acceptable salts and solvates and hydrolysable esters thereof.

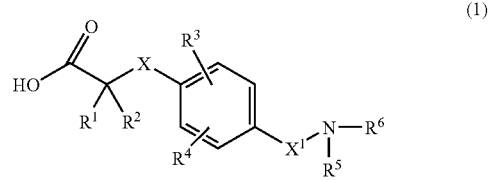

(1)

Wherein:
$R^1$ and $R^2$ are independently hydrogen or $C_{1-3}$ alkyl;
X represents a bond, $CH_2$ or O;
$R^3$ and $R^4$ are independently hydrogen, $C_{1-6}$ alkyl, $OCH_3$, $CF_3$, allyl or halogen;
$X^1$ is $CH_2$, $SO_2$, or CO;
$R^5$ is —$C_{1-6}$alkyl (optionally substituted by $C_{1-6}$-alkoxy or $C_{1-6}$-alkylthio), —$C_{2-6}$alkenyl, —$C_{0-6}$ alkyl phenyl (wherein the phenyl is optionally substituted by one or more $CF_3$, halogen, $C_{1-3}$ alkyl, $C_{1-3}$ alkoxy), —$COC_{1-6}$ alkyl, —$SO_2C_{1-6}$ alkyl;
$R^6$ is phenyl or a 6 membered heteroaryl group containing 1, 2 or 3 N atoms wherein the phenyl or heteroaryl group is optionally substituted with 1, 2 or 3 moieties selected from the group consisting of $C_{1-6}$ alkyl, halogen, —$OC_{1-6}$ alkyl, —$SO_2C_{1-3}$ alkyl, phenyl (optionally substituted by one or more groups selected from halogen, $CF_3$, $C_{1-3}$ alkyl, $OC_{1-3}$ alkyl, acetyl, CN).

In another aspect, the present invention discloses a method for prevention or treatment of a disease or condition mediated by one or more human PPAR alpha, gamma or delta ("hPPARs") comprising administration of a therapeutically effective amount of a compound of this invention. hPPAR mediated diseases or conditions include dyslipidemia including associated diabetic dyslipidemia and mixed dyslipidemia, syndrome X (as defined in this application this embraces metabolic syndrome), heart failure, hypercholesterolemia, cardiovascular disease including atherosclerosis, arteriosclerosis, and hypertriglyceridemia, type II diabetes mellitus, type I diabetes, insulin resistance, hyperlipidemia, inflammation, epithelial hyperproliferative diseases including eczema and psoriasis and conditions associated with the lung and gut and regulation of appetite and food intake in subjects suffering from disorders such as obesity, anorexia bulimia, and anorexia nervosa, cancer, Alzheimers disease or other cognitive disorders. In particular, the compounds of this invention are useful in the treatment and prevention of diabetes, obesity and cardiovascular diseases and conditions including atherosclerosis, arteriosclerosis, hypertriglyceridemia, and mixed dyslipidaemia.

In another aspect, the present invention provides pharmaceutical compositions comprising a compound of the invention, preferably in association with a pharmaceutically acceptable diluent or carrier.

In another aspect, the present invention provides a compound of the invention for use in therapy, and in particular, in human medicine.

In another aspect, the present invention provides the use of a compound of the invention for the manufacture of a medicament for the treatment of a hPPAR mediated disease or condition.

As used herein, "a compound of the invention" means a compound of formula (I) or a pharmaceutically acceptable salt, or solvate, or hydrolysable ester thereof.

While hydrolyzable esters are included in the scope of this invention, the acids are preferred because the data suggests that while the esters are useful compounds, it may actually be the acids to which they hydrolyse that are the active compounds. Esters that hydrolyse readily can produce the carboxylic acid in the assay conditions or in vivo. Generally the carboxylic acid is active in both the binding and transient transfection assays, while the ester does not usually bind well but is active in the transient transfection assay presumably due to hydrolysis. Preferred hydrolysable esters are $C_{1-6}$ alkyl esters wherein the alkyl group may be straight chain or branched chain. Methyl or ethyl esters are more preferred.

Preferably each $R^1$ and $R^2$ is independently H or methyl. More preferably $R^1$ and $R^2$ are both H or both methyl. Even more preferably, $R^1$ and $R^2$ are both H.

Preferably X is O.

Preferably $R^3$ and $R^4$ are independently H or $C_{1-3}$alkyl. More preferably at least one of $R^3$ and $R^4$ is hydrogen and when one of $R^3$ and $R^4$ is hydrogen and the other is not, then the one that is not hydrogen is preferably ortho to the depicted moiety X. More preferably the one that is not hydrogen is methyl.

Preferably $X^1$ is $CH_2$.

Preferably $R^5$ is butyl or methoxyethyl.

Preferably $R^6$ is phenyl or a 6 membered heterocycle selected from pyrimidine, pyridine, pyridazine, pyrazine, each of which is substituted by phenyl (optionally substituted by one or more $CF_3$, $C_{1-3}$alkyl, halogen, CN) and optionally a further $C_{1-3}$alkyl substituent. Preferably this phenyl substituent is meta to the depicted N. More preferably the substituent on the phenyl or 6 membered heterocycle is para $C_6H_4CF_3$, $C_6H_4Me$ or $C_6H_4Cl$.

Preferred compounds of the invention are:

2-Methyl-2-{2-methyl-4-[([4-(trifluoromethyl)benzyl]{6-[4-(trifluoromethyl)phenyl]pyridin-2-yl}amino)methyl]phenoxy}propanoic acid 2-{4-[(Butyl{6-[4-(trifluoromethyl)phenyl]pyridin-2-yl}amino) methyl]-2-methylphenoxy}-2-methylpropanoic acid {4-[(Butyl{6-[4-(trifluoromethyl)phenyl]pyridin-2-yl}amino)methyl]-2-methylphenoxy}acetic acid

[4-({Butyl[4'-(trifluoromethyl)-1,1'-biphenyl-3-yl]amino}methyl)-2-methylphenoxy]acetic acid

[4-({(2-Methoxyethyl)[4'-(trifluoromethyl)-1,1'-biphenyl-3-yl]amino}methyl)-2-methylphenoxy]acetic acid

[2-Methyl-4-({pentyl[4'-(trifluoromethyl)-1,1'-biphenyl-3-yl]amino}methyl)phenoxy]acetic acid

[4-({(2-Cyclopropylethyl)[4'-(trifluoromethyl)-1,1'-biphenyl-3-yl]amino}methyl)-2-methylphenoxy]acetic acid

[2-Methyl-4-({propyl[4'-(trifluoromethyl)-1,1'-biphenyl-3-yl]amino}methyl)phenoxy]acetic acid

[2-Methyl-4-({[2-(methylthio)ethyl][4'-(trifluoromethyl)-1,1'-biphenyl-3-yl]amino}methyl)phenoxy]acetic acid

[4-({Butyl[2-methyl-4'-(trifluoromethyl)-1,1'-biphenyl-3-yl]amino}methyl)-2-methylphenoxy]acetic acid

[4-({(2-Methoxyethyl)[2-methyl-4'-(trifluoromethyl)-1,1'-biphenyl-3-yl]amino}methyl)-2-methylphenoxy]acetic acid

[4-({Butyryl[4'-(trifluoromethyl)-1,1'-biphenyl-3-yl]amino}methyl)-2-methylphenoxy]acetic acid

[2-Methyl-4-({(propylsulfonyl)[4'-(trifluoromethyl)-1,1'-biphenyl-3-yl]amino}methyl)phenoxy]acetic acid

[4-({Butyl[4'-(trifluoromethyl)-1,1'-biphenyl-3-yl]amino}sulfonyl)-2-methylphenoxy]acetic acid

[2-Methyl-4-({pentyl[4'-(trifluoromethyl)-1,1'-biphenyl-3-yl]amino}sulfonyl)phenoxy]acetic acid

[4-({(2-Cyclopropylethyl)[4'-(trifluoromethyl)-1,1'-biphenyl-3-yl]amino}sulfonyl)-2-methylphenoxy]acetic acid {4-[(Butyl{4-[4-(trifluoromethyl)phenyl]pyrimidin-2-yl}amino) methyl]-2-methylphenoxy}acetic acid

[4-({Butyl[4-(4-chlorophenyl)pyrimidin-2-yl]amino}methyl)-2-methylphenoxy]acetic acid {4-[((2-Methoxyethyl){4-[4-(trifluoromethyl)phenyl]pyrimidin-2-yl}amino)methyl]-2-methylphenoxy}acetic acid (4-{[[4-(4-Chlorophenyl)pyrimidin-2-yl](2-methoxyethyl)amino]methyl}-2-methylphenoxy)acetic acid {2-Methyl-4-[(propyl{4-[4-(trifluoromethyl)phenyl]pyrimidin-2-yl}amino)methyl]phenoxy}acetic acid {4-[(Butyl{6-[4-(trifluoromethyl)phenyl]pyrazin-2-yl}amino)methyl]-2-methylphenoxy}acetic acid

[4-({Butyl[6-(4-methylphenyl)pyrazin-2-yl]amino}methyl)-2-methylphenoxy]acetic acid {4-[((2-Methoxyethyl){6-[4-(trifluoromethyl)phenyl]pyrazin-2-yl}amino)methyl]-2-methylphenoxy}acetic acid (4-{[Butyl(2,4'-dimethyl-1,1'-biphenyl-3-yl)amino]methyl}-2-methylphenoxy)acetic acid (4-{[Butyl(4'-fluoro-2-methyl-1,1'-biphenyl-3-yl)amino]methyl}-2-methylphenoxy)acetic acid (4-{[Butyl(4'-cyano-2-methyl-1,1'-biphenyl-3-yl)amino]methyl}-2-methylphenoxy)acetic acid (4-{[Butyl(4'-methoxy-2-methyl-1,1'-biphenyl-3-yl)amino] methyl}-2-methylphenoxy)acetic acid
(4-{[Butyl(4'-chloro-2-methyl-1,1'-biphenyl-3-yl)amino] methyl}-2-methylphenoxy)acetic acid
(4-{[(4'-Chloro-2-methyl-1,1'-biphenyl-3-yl)(2-methoxyethyl)amino]methyl}-2-methylphenoxy)acetic acid
(4-{[(2,4'-Dimethyl-1,1'-biphenyl-3-yl)(2-methoxyethyl)amino]methyl}-2-methylphenoxy)acetic acid
(4-{[(2-Methoxyethyl)(4'-methoxy-2-methyl-1,1'-biphenyl-3-yl)amino]methyl}-2-methylphenoxy)acetic acid
(2-Methyl-4-{[[2-methyl-4'-(trifluoromethyl)-1,1'-biphenyl-3-yl](propyl)amino]methyl}phenoxy)acetic acid
(4-{[(4'-Chloro-2-methyl-1,1'-biphenyl-3-yl)(propyl)amino]methyl}-2-methylphenoxy)acetic acid
(4-{[(2,4'-Dimethyl-1,1'-biphenyl-3-yl)(propyl)amino]methyl}-2-methylphenoxy)acetic acid
(4-{[(4'-Fluoro-2-methyl-1,1'-biphenyl-3-yl)(propyl)amino] methyl}-2-methylphenoxy)acetic acid
(4-{[(4'-Cyano-2-methyl-1,1'-biphenyl-3-yl)(propyl)amino] methyl}-2-methylphenoxy)acetic acid
(4-{[(4'-Methoxy-2-methyl-1,1'-biphenyl-3-yl)(propyl) amino]methyl}-2-methylphenoxy)acetic acid
{4-[(Butyl{5-methyl-6-[4-(trifluoromethyl)phenyl]pyrimidin-4-yl}amino)methyl]-2-methylphenoxy}acetic acid
[4-({Butyl[6-(4-methoxyphenyl)-5-methylpyrimidin-4-yl] amino}methyl)-2-methylphenoxy]acetic acid
[4-({Butyl[5-methyl-6-(4-methylphenyl)pyrimidin-4-yl] amino}methyl)-2-methylphenoxy]acetic acid
[4-({Butyl[6-(4-chlorophenyl)-5-methylpyrimidin-4-yl] amino}methyl)-2-methylphenoxy]acetic acid
[4-({Butyl[6-(4-chlorophenyl)-2-pyrazin-2-yl] amino}methyl)-2-methylphenoxy]acetic acid
[4-({[6-(4-Chlorophenyl)pyrazin-2-yl][2-(methyloxy)ethyl] amino}methyl)-2-methylphenoxy]acetic acid
{2-Methyl-4-[(propyl{6-[4-(trifluoromethyl)phenyl] pyrazin-2-yl}amino)methyl]phenoxy}acetic acid
(2-Methyl-4-{[{5-methyl-6-[4-(trifluoromethyl)phenyl]pyrimidin-4-yl}(propyl)amino]methyl}phenoxy)acetic acid
(4-{[[6-(4-Chlorophenyl)-5-methylpyrimidin-4-yl](propyl) amino]methyl}-2-methylphenoxy)acetic acid
(2-Methyl-4-{[[5-methyl-6-(4-methylphenyl)pyrimidin-4-yl](propyl)amino]methyl}phenoxy)acetic acid
(2-Methyl-4-{[{5-methyl-6-[4-(methyloxy)phenyl]pyrimidin-4-yl}(propyl)amino]methyl}phenoxy)acetic acid
{4-[(Butyl{6-[4-(trifluoromethyl)phenyl]pyrazin-2-yl}amino)methyl]-2-ethylphenoxy}acetic acid
{2-Ethyl-4-[(2-methyloxyethyl){6-[4-(trifluoromethyl)phenyl]pyrazin-2-yl}amino)methyl]phenoxy}acetic acid
[4-({Butyl[5-methyl-6-(4-methylphenyl)pyrimidin-4-yl] amino}methyl)-2-ethylphenoxy]acetic acid
[4-({Butyl[2-methyl-4'-(trifluoromethyl)-1,1'-biphenyl-3-yl]amino}sulfonyl)-2-methylphenoxy]acetic acid
[2-Methyl-4-({(propylsulfonyl)[4'-(trifluoromethyl)-1,1'-biphenyl-3-yl]amino}methyl)pheoxy]acetic acid
[4-({Butyl[6-(4-chlorophenyl)-5-methylpyrimidin-4-yl] amino}methyl)-2-ethylphenoxy]acetic acid
{4-[(Butyl{5-methyl-6-[4-(trifluoromethyl)phenyl]pyrimidin-4-yl}amino)methyl]-2-ethylphenoxy}acetic acid
{2-Ethyl-4-[([2-(methyloxy)ethyl]{4-[4-(trifluoromethyl) phenyl]pyrimidin-2-yl}amino)methyl]phenoxy}acetic acid
{2-Methyl-4-[(2-propen-1-yl{6-[4-(trifluoromethyl)phenyl] pyridin-2-yl}amino)methyl]phenoxy}acetic acid While the preferred groups for each variable have generally been listed above separately for each variable, preferred compounds of this invention include those in which several or each variable in Formula (I) is selected from the preferred, more preferred, or most preferred groups for each variable. Therefore, this invention is intended to include all combinations of preferred and most preferred groups.

Those skilled in the art will recognize that stereocenters exist in compounds of formula (I). Accordingly, the present invention includes all possible stereoisomers and geometric isomers of formula (I) and includes not only racemic compounds but this invention is also intended to cover each of these isomers in their racemic, enriched, or purified forms. When a compound of formula (I) is desired as a single enantiomer, it may be obtained either by resolution of the final product or by stereospecific synthesis using an optically active catalyst or a catalytic system with optically active ligands or isomerically pure starting material or any convenient intermediate. Resolution of the final product, an intermediate or a starting material may be effected by any suitable method known in the art. See, for example, Stereochemistry of Carbon Compounds by E. L. Eliel (Mcgraw Hill, 1962) and Tables of Resolving Agents by S. H. Wilen. Additionally, in situations where tautomers of the compounds of formula (I) are possible, the present invention is intended to include all tautomeric forms of the compounds. In some of these chiral compounds the activities at the various PPAR receptors varies between the S and R isomers. Which of these isomers is preferred depends on the particular desired utility of the compound. In other words, even with the same compound, it is possible that the S isomer will be preferred for some uses, while the R isomer will be preferred for others.

The hPPAR agonists of formula (I) may be agonists of only one type ("selective agonists"), agonists for two PPAR subtypes ("dual agonists"), or agonists for all three subtypes ("pan agonists"). As used herein, by "agonist", or "activating compound", or "activator", or the like, is meant those compounds which have a pKi of at least 6.0 preferably at least 7.0 to the relevant PPAR, for example hPPARδ, in the binding assay described below, and which achieve at least 50% activation of the relevant PPAR relative to the appropriate indicated positive control in the transfection assay described below at concentrations of $10^{-5}$ M or less. More preferably, the agonists of this invention achieve 50% activation of at least one human PPAR in the relevant transfection assay at concentrations of $10^{-6}$ M or less. Preferably, the compounds of formula (I) are hPPAR agonists. More preferably the compounds are hPPARδ agonists. More preferably they are selective hPPARδ agonists.

It will also be appreciated by those skilled in the art that the compounds of the present invention may also be utilised in the form of a pharmaceutically acceptable salt or solvate thereof. The physiologically acceptable salts of the compounds of formula (I) include conventional salts formed from pharmaceutically acceptable inorganic or organic acids or bases as well as quaternary ammonium acid addition salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic, naphthalene-2-sulfonic, benzenesulfonic hydroxynaphthoic, hydroiodic, malic, steroic, tannic and the like. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts. Those skilled in the art of organic chemistry will appreciate that many organic compounds can form complexes with solvents in which they are reacted or from which they are precipitated or crystallized. These complexes are known as "solvents". For example, a complex with water is known as a "hydrate". Solvates of the compound of formula (I) are within the scope of the invention. References hereinafter to a compound according to the invention include both compounds of formula (I) and their pharmaceutically acceptable salts and solvates.

The compounds of the invention and their pharmaceutically acceptable derivatives are conveniently administered in the form of pharmaceutical compositions. Such compositions may conveniently be presented for use in conventional manner in admixture with one or more physiologically acceptable carriers or excipients.

While it is possible that compounds of the present invention may be therapeutically administered as the raw chemical, it is preferable to present the active ingredient as a pharmaceutical formulation. The carrier(s) must be "acceptable" in the sense of being compatible with the other ingredients of the formulation and not deleterious to the recipient thereof.

Accordingly, the present invention further provides for a pharmaceutical formulation comprising a compound of formula (I) or a pharmaceutically acceptable salt or solvate thereof together with one or more pharmaceutically acceptable carriers therefore and, optionally, other therapeutic and/or prophylactic ingredients.

The formulations include those suitable for oral, parenteral (including subcutaneous e.g. by injection or by depot tablet, intradermal, intrathecal, intramuscular e.g. by depot and intravenous), rectal and topical (including dermal, buccal and sublingual) administration although the most suitable route may depend upon for example the condition and disorder of the recipient. The formulations may conveniently be presented in unit dosage form and may be prepared by any of the methods well known in the art of pharmacy. All methods include the step of bringing into association the compounds ("active ingredient") with the carrier, which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations suitable for oral administration may be presented as discrete units such as capsules, cachets or tablets (e.g. chewable tablets in particular for paediatric administration) each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a other conventional excipients such as binding agents, (for example, syrup, acacia, gelatin, sorbitol, tragacanth, mucilage of starch or polyvinylpyrrolidone), fillers (for example, lactose, sugar, microcrystalline cellulose, maize-starch, calcium phosphate or sorbitol), lubricants (for example, magnesium stearate, stearic acid, talc, polyethylene glycol or silica), disintegrants (for example, potato starch or sodium starch glycollate) or wetting agents, such as sodium lauryl sulfate. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The tablets may be coated according to methods well-known in the art.

Alternatively, the compounds of the present invention may be incorporated into oral liquid preparations such as aqueous or oily suspensions, solutions, emulsions, syrups or elixirs, for example. Moreover, formulations containing these compounds may be presented as a dry product for constitution with water or other suitable vehicle before use. Such liquid preparations may contain conventional additives such as suspending agents such as sorbitol syrup, methyl cellulose, glucose/sugar syrup, gelatin, hydroxyethylcellulose, carboxymethyl cellulose, aluminum stearate gel or hydrogenated edible fats; emulsifying agents such as lecithin, sorbitan mono-oleate or acacia; non-aqueous vehicles (which may include edible oils) such as almond oil, fractionated coconut oil, oily esters, propylene glycol or ethyl alcohol; and preservatives such as methyl or propyl p-hydroxybenzoates or sorbic acid. Such preparations may also be formulated as suppositories, e.g., containing conventional suppository bases such as cocoa butter or other glycerides.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations may be presented in unit-dose or multi-dose containers, for example sealed ampoules and vials, and may be stored in a freeze-dried (lyophilised) condition requiring only the addition of a sterile liquid carrier, for example, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter, hard fat or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

The compounds may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

In addition to the ingredients particularly mentioned above, the formulations may include other agents conventional in the art having regard to the type of formulation in question, for example those suitable for oral administration may include flavouring agents.

It will be appreciated by those skilled in the art that reference herein to treatment extends to prophylaxis as well as the treatment of established diseases or symptoms. Moreover, it will be appreciated that the amount of a compound of the invention required for use in treatment will vary with the nature of the condition being treated and the age and the condition of the patient and will be ultimately at the discretion of the attendant physician or veterinarian. In general, however, doses employed for adult human treatment will typically be in the range of 0.02–5000 mg per day, preferably 1–1500 mg per day. The desired dose may conveniently be presented in a single dose or as divided doses administered at appropriate intervals, for example as two, three, four or more sub-doses per day. The formulations according to the invention may contain between 0.1–99% of the active ingredient, conveniently from 30–95% for tablets and capsules and 3–50% for liquid preparations.

The compound of formula (I) for use in the instant invention may be used in combination with other therapeutic agents for example, statins and/or other lipid lowering drugs for example MTP inhibitors and LDLR upregulators. The compounds of the invention may also be used in combination with antidiabetic agents, e.g. metformin, sulfonylureas and/or PPAR gamma, PPAR alpha or PPAR alpha/gamma agonists (for example thiazolidinediones such as e.g. Pioglitazone and Rosiglitazone). The compounds may also be used in combination with antihypertensive agents such as angiotensin antagonists e.g. telmisartan, calcium channel antagonists e.g. lacidipine and ACE inhibitors e.g. enalapril. The invention thus provides in a further aspect the use of a combination comprising a compound of formula (I) with a further therapeutic agent in the treatment of a hPPAR mediated disease.

When the compounds of formula (I) are used in combination with other therapeutic agents, the compounds may be administered either sequentially or simultaneously by any convenient route.

The combinations referred to above may conveniently be presented for use in the form of a pharmaceutical formulation and thus pharmaceutical formulations comprising a combination as defined above optimally together with a pharmaceutically acceptable carrier or excipient comprise a further aspect of the invention. The individual components of such combinations may be administered either sequentially or simultaneously in separate or combined pharmaceutical formulations.

When combined in the same formulation it will be appreciated that the two compounds must be stable and compatible with each other and the other components of the formulation and may be formulated for administration. When formulated separately they may be provided in any convenient formulation, conveniently in such a manner as are known for such compounds in the art.

When a compound of formula (I) is used in combination with a second therapeutic agent active against the same hPPAR mediated disease, the dose of each compound may differ from that when the compound is used alone. Appropriate doses will be readily appreciated by those skilled in the art.

Compounds of this invention may be conveniently prepared by general processes illustrated by the schemes below.

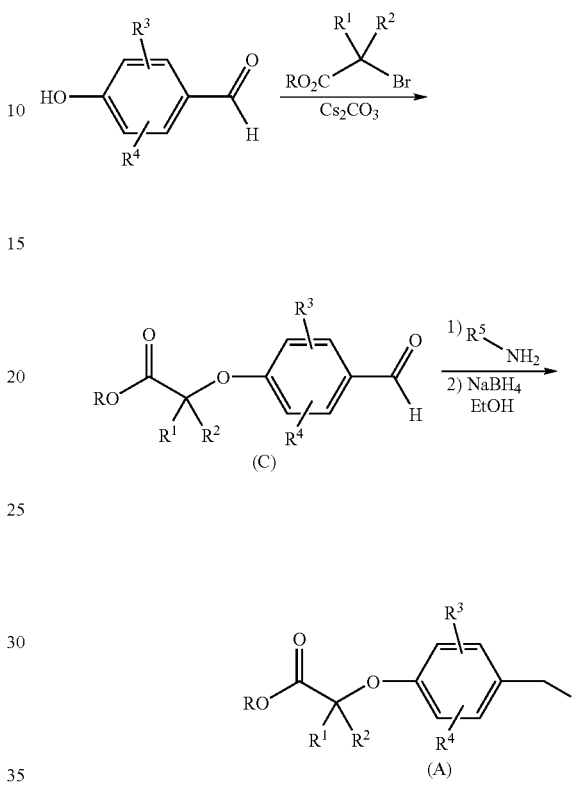

Scheme 1

Intermediates (A) can be prepared by alkylating a suitable 4-hydroxybenzaldehyde to afford benzaldehydes (intermediate C), followed by reductive amination of the aldehyde moiety.

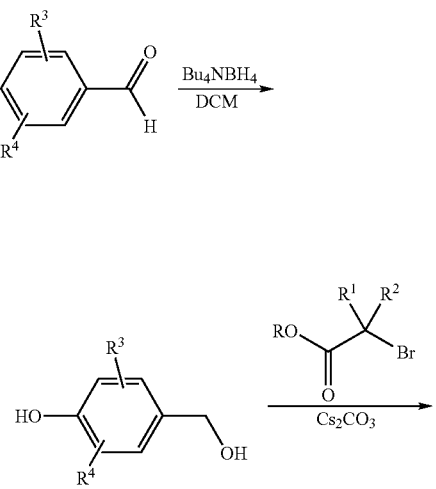

Scheme 2

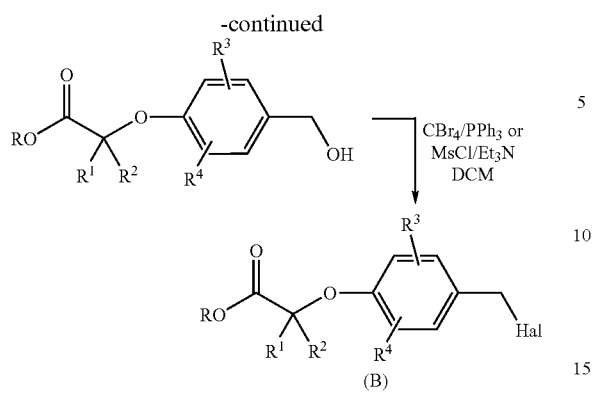

Intermediates (B) can be prepared by reducing a suitable 4-hydroxybenzaldehyde to the alcohol. Alkylation of the phenol moiety with a suitable bromoacetate, followed by halogenation of the benzylic alcohol affords intermediates (B).

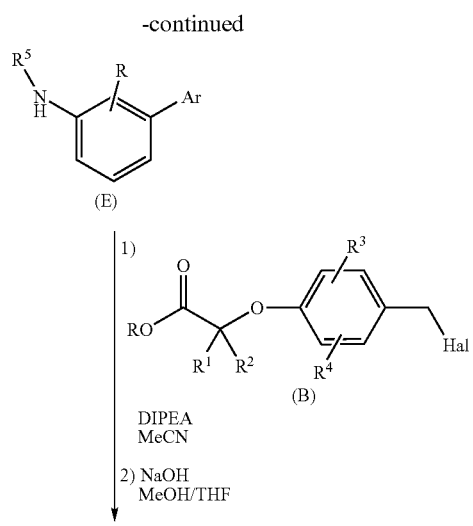

Scheme 3

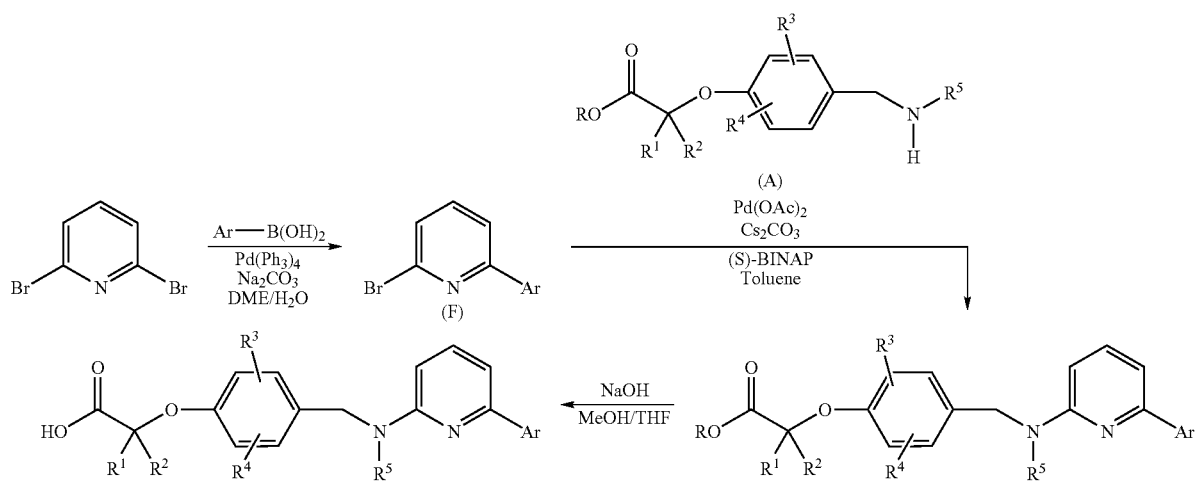

Commerical 2,6-dibromopyridine may be coupled with boronic acids using Suzuki coupling conditions. The resultant monobromides can then be treated with an amine (intermediate A) in a Buchwald reaction to yield the coupled products. The ester group can then be hydolysed to the corresponding carboxylic acids under standard conditions.

Scheme 4

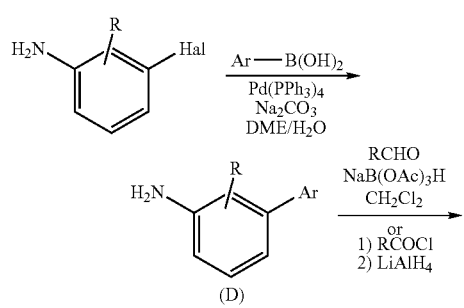

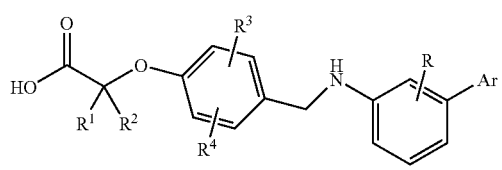

Suitable halogenated-anilines can be coupled with boronic acids under Suzuki coupling conditions to afford coupled products (intermediate D). Reductive amination, or acylation and reduction, of the resulting compounds yield the secondary anilines (intermediate E) which are alkylated with halides (intermediate B). Hydrolysis of the carboxylic esters, under standard conditions yield the carboxylic acids.

Scheme 5

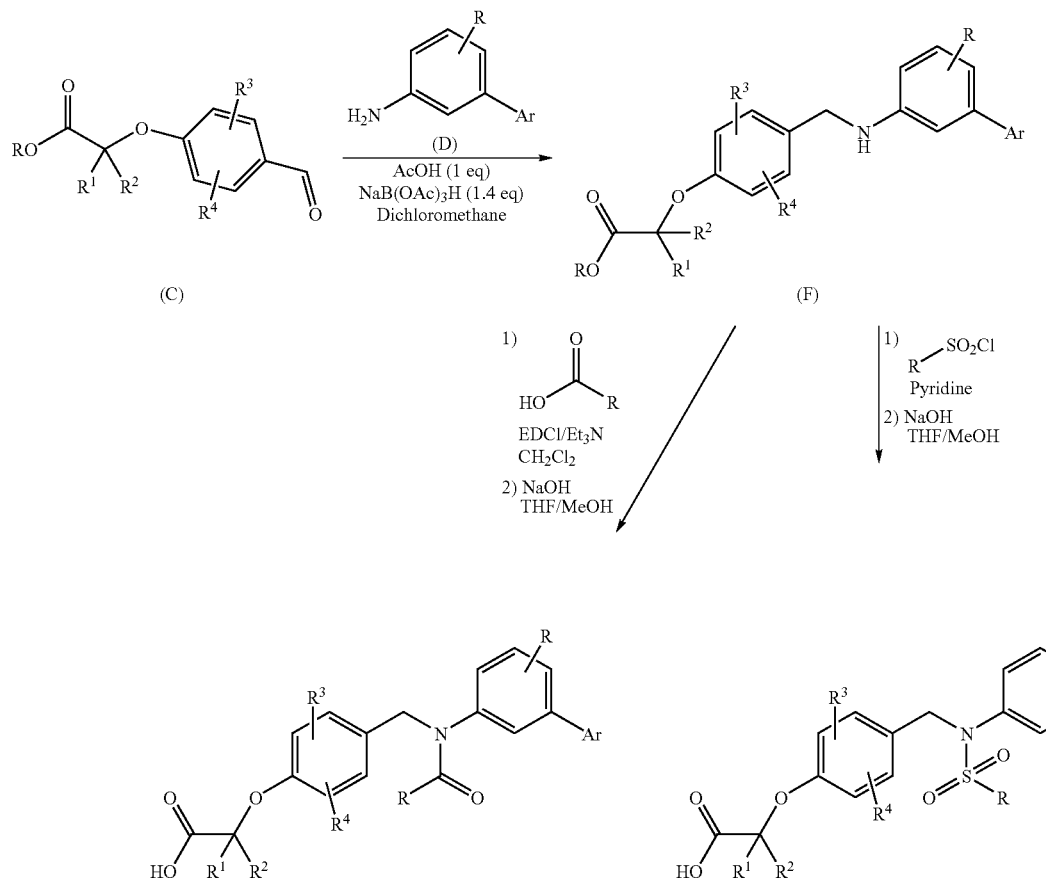

Reductive amination of an aniline (intermediate D) with an aldehyde (intermediate C) affords a secondary aniline (intermediate F), which can be converted to an amide by coupling with a suitable carboxylic acid and to the sulfonamide by reaction with an appropriate alkyl sulfonyl chloride. The resultant esters are hydrolysed under standard conditions to yield the carboxylic acids.

Scheme 6

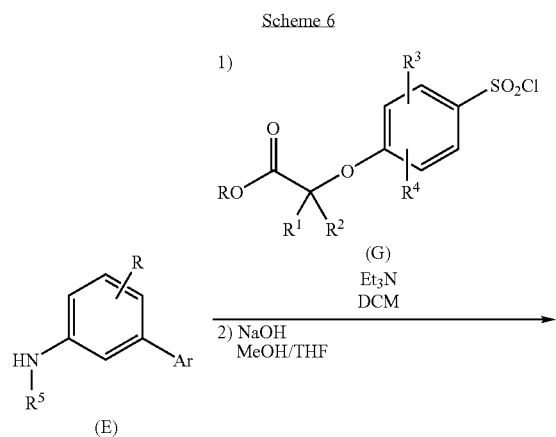

-continued

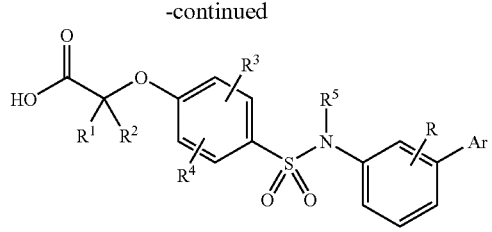

Reaction of a secondary aniline (intermediate E) with a sulfonyl chloride (intermediate G) affords sulfonamide linked compounds. Hydrolysis of the esters, under standard conditions yield the carboxylic acids.

Scheme 7

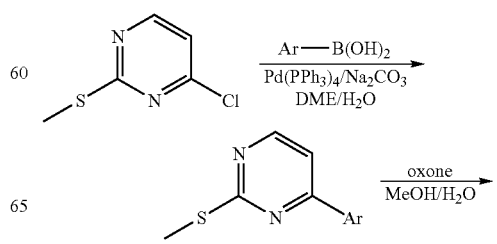

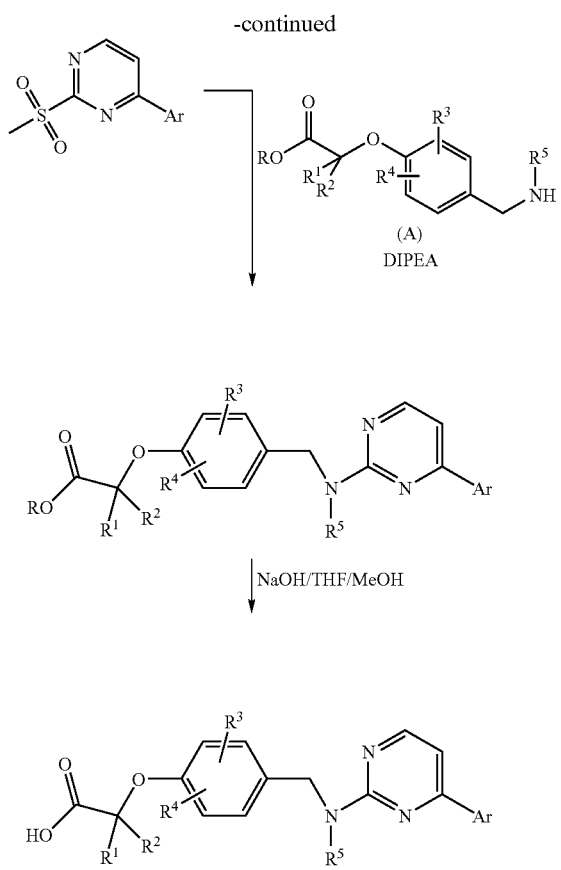

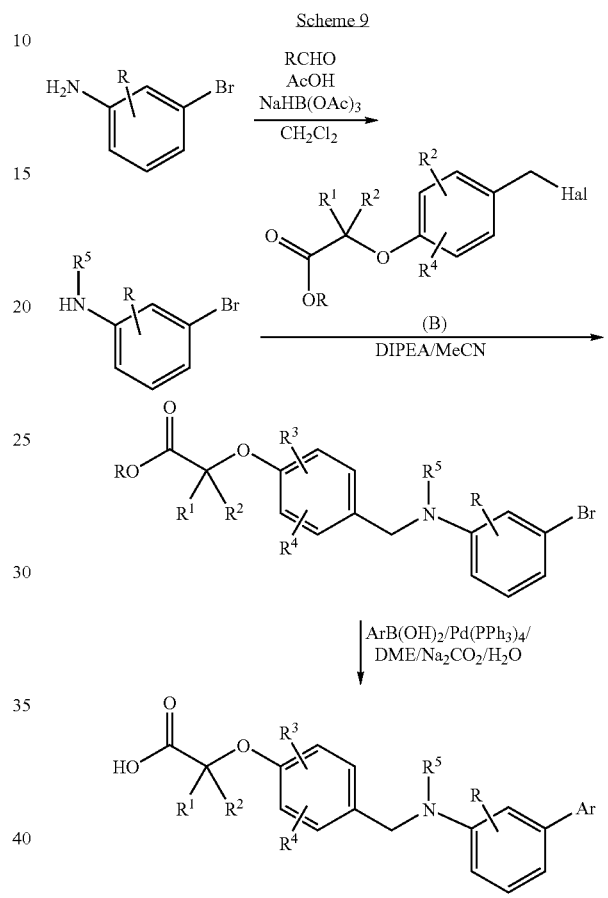

Commercial dichloropyrazine can be coupled with boronic acids using Suzuki coupling conditions. The resultant mono chloropyrazine can be converted to the bromide by treatment with phosphorus tribromide. Displacement of the bromide with an amine (intermediate A) in the presence of N,N-diisopropylethylamine yield the esters which are hydrolysed to the acids, under standard conditions.

Commercially available 4-chloro-2-(methylthio)pyrimidine and boronic acids can be coupled under Suzuki conditions. Oxidation of thiols affords the corresponding sulfones. The sulfones can then be reacted with amines (intermediates A). The resultant coupled compounds are hydrolysed under standard conditions to yield the carboxylic acids.

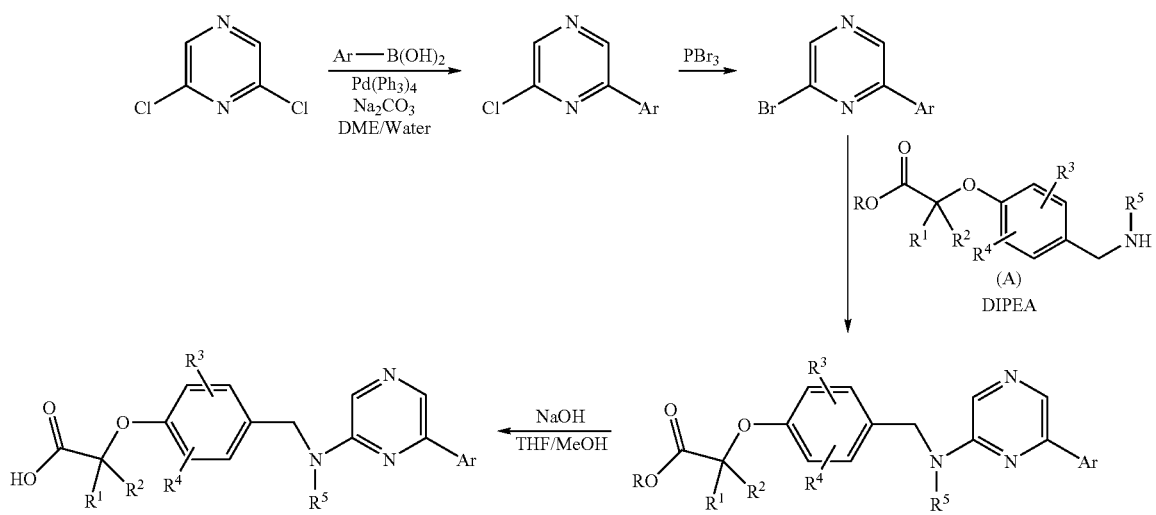

Reductive amination of a suitable aniline with an aldehyde affords a secondary aniline which can then alkylated with a suitable halide (intermediate B). This product can be coupled with an appropriate boronic acid under standard Suzuki coupling conditions affording carboxylic acids directly.

Scheme 10

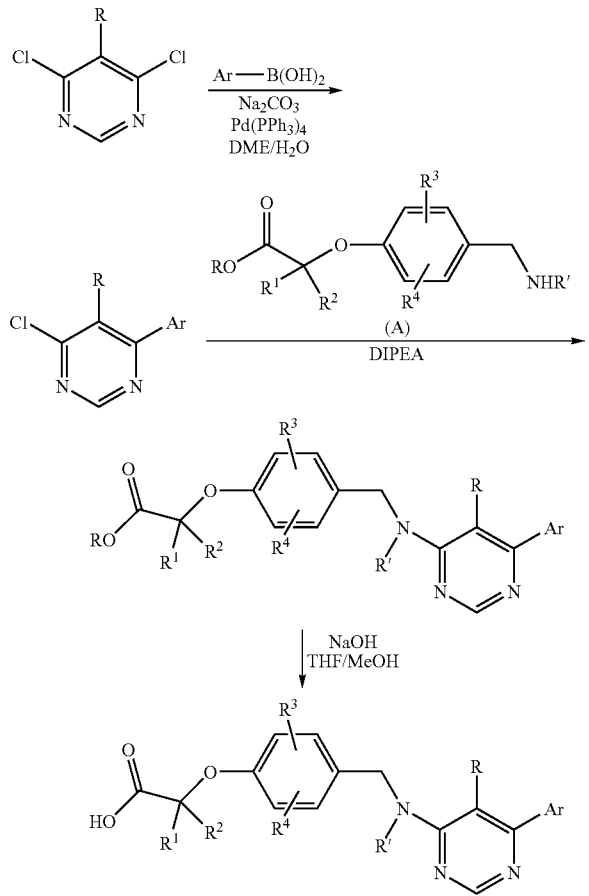

A suitable dichloropyrimidine can be coupled with boronic acids using Suzuki coupling conditions. The resultant mono-chloro pyrimidines can be treated with an amine (intermediate A) in the presence of N,N-diisopropylethylamine to yield the esters which are hydrolysed under standard conditions to the carboxylic acids.

The following illustrates Intermediates and Examples of Formula 1 which should not be construed as constituting a limitation thereto.

General purification and analytical methods:

LC/MS refers to analysis by analytical HPLC which was conducted on a Supelcosil LCABZ+PLUS column (3 μm, 3.3 cm×4.6 mm ID) eluting with 0.1% $HCO_2H$ and 0.01 M ammonium acetate in water (solvent A), and 95% acetonitrile and 0.05% $HCO_2H$ in water (solvent B), using the following elution gradient 0–0.7 minutes 0% B, 0.7–4.2 minutes 0→100% B, 4.2–5.3 minutes 100% B, 5.3–5.5 minutes 100→0% B at a flow rate of 3 ml/minute. The mass spectra (MS) were recorded on a Fisons VG Platform mass spectrometer using electrospray positive ionisation [(ES+ve to give $[M+H]^+$ and $[M+NH_4]^+$ molecular ions] or electrospray negative ionisation [(ES−ve to give $[M-H]^-$ molecular ion] modes.

$^1H$ NMR spectra were recorded using a Bruker DPX 400 MHz spectrometer.

Biotage™ chromatography refers to purification carried out using equipment sold by Dyax Corporation (either the Flash 40i or Flash 150i) and cartridges pre-packed with KP-Sil™ silica.

Reactivials used are those supplied by Perbio Science UK Ltd.

Mass directed auto-prep HPLC refers to the method where the material was purified by high performance liquid chromatography on a HPLCABZ+ 5 μm column (5 cm×10 mm i.d.) with 0.1% $HCO_2H$ in water and 95% MeCN, 5% water (0.5% $HCO_2H$) utilising the following gradient elution conditions: 0–1.0 minutes 5% B, 1.0–8.0 minutes 5→30% B, 8.0–8.9 minutes 30% B, 8.9–9.0 minutes 30→95% B, 9.0–9.9 minutes 95% B, 9.9–10 minutes 95→0% B at a flow rate of 8 ml/minute. The Gilson 202-fraction collector was triggered by a VG Platform Mass Spectrometer on detecting the mass of interest.

Hydrophobic frits refers to filtration tubes sold by Whatman.

SPE (solid phase extraction) refers to the use of cartridges sold by International Sorbent Technology Ltd. SCX is a benzene sulfonic acid stationary phase.

TLC (thin layer chromatography) refers to the use of TLC plates sold by Merck coated with silica gel 60 $F_{254}$.

Abbreviations:
TLC: thin layer chromatography
DMSO-$d_6$: deuterated dimethylsulfoxide
$CDCl_3$: deuterated chloroform
MeOH-$d^4$: deuterated methanol
DCM: dichloromethane
DMF: N,N-dimethylformamide
$Et_2O$: diethyl ether
EtOAc: ethyl acetate
MeCN: acetonitrile
MeOH: methanol
$nBu_3P$: tributylphosphine
$R_t$: retention time
THF: tetrahydrofuran
br: broad
s: singlet
d: doublet
dd: doublet of doublets
t: triplet
q: quartet
m: multiplet
rt: room temperature Intermediate 1: 2-Bromo-6-[4-(trifluoromethyl)phenyl] pyridine

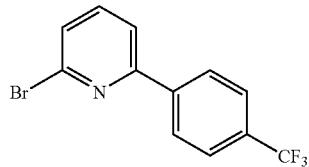

To a solution of 2,6-dibromopyridine (1.25 g, 5.28 mmol) in dimethoxyethane (100 mL) and water (50 mL), was added 4-trifluromethylphenylboronic acid (1 g, 5.27 mmol) and sodium carbonate (1.45 g, 13.7 mmol). The resulting mixture was flushed with nitrogen prior to addition of tetrakis (triphenylphosphine) palladium (0) (60 mg, 0.05 mmol). The reaction mixture was heated to reflux under nitrogen for 5 h and then allowed to attain room temperature. The solvents were removed in vacuo and the residue diluted with water (50 mL) and then extracted EtOAc (2×100 mL). The organic solution was dried (MgSO$_4$), filtered and the solvents removed in vacuo. Purification by Biotage™ chromatography (Silica, 90 g) eluting with 4:1 cyclohexane:chloroform afforded the title compound as a white solid (0.35 g).

$^1$H NMR (400 MHz; CDCl$_3$) δ: 7.49 (1H, d, J 7.5 Hz), 7.65 (1H, t, J 8 Hz), 7.73 (3H, m), 8.11 (2H, d, J 8.5 Hz).

Intermediate 2: Ethyl 2-methyl-2-{2-methyl-4-[([4-(trifluoromethyl)benzyl]{6-[4-(trifluoromethyl)phenyl]pyridin-2-yl}amino)methyl]phenoxy}propanoate

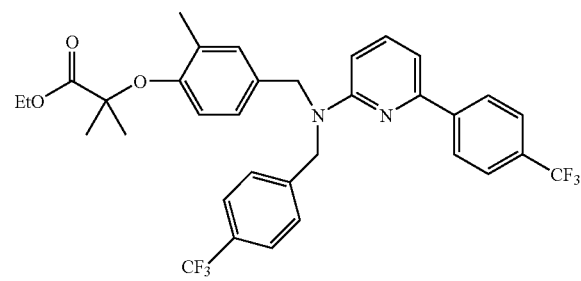

A mixture of ethyl 2-methyl-2-[2-methyl-4-({[4-(trifluoromethyl)benzyl]amino}methyl)phenoxy]propanoate (0.13 g, 0.318 mmol ), 2-bromo-6-[4-(trifluoromethyl) phenyl]pyridine (78.5 mg, 0.26 mmol), palladium (II) acetate (4.8 mg, 0.021 mmol), (R)-2,2'-bis(diphenylphosphino)-1,1'-binapthyl (19.8 mg, 0.032 mmol) and caesium carbonate (0.13 g, 0.397 mmol) in toluene (1.8 mL) were heated at 70° C. in a reactivial for 18 hours. After cooling to room temperature, the reaction mixture was filtered and the solvent removed in vacuo. Purification by SPE (Silica, 10 g) eluting with 99:1–19:1 cyclohexane:EtOAc afforded the title compound as a colourless oil (75 mg).

LC/MS: m/z 631.3 [M+H]$^+$, R$_t$4.7 min.

Intermediate 3: Ethyl 2-{4-[(butyl{6-[4-(trifluoromethyl)phenyl]pyridin-2-yl}amino)methyl]-2-methylphenoxy}-2-methylpropanoate

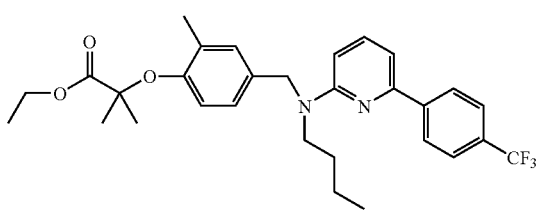

Palladium (II) acetate (1.4 mg, 0.006 mmol) and (S)-2,2'-bis(diphenylphosphino)-1,1'-binapthyl (5.9 mg, 0.0095 mmol) in anhydrous toluene (0.32 mL) were stirred together at 70° C. in a sealed reactivial for 30 minutes. The vial was then allowed to attain room temperature before the ethyl 2-{4-[(butylamino)methyl]-2-methylphenoxy}-2-methylpropanoate (29 mg, 0.095 mmol), 2-bromo-6-[4-(trifluoromethyl)phenyl]pyridine (24 mg, 0.08 mmol) and caesium carbonate (36 mg, 0.11 mmol) were added. The vial was then sealed and heated at 80° C. for 18 h, then allowed to cool to room temperature the reaction mixture filtered and the solvent removed in vacuo. Purification by SPE (Silica, 10 g) eluting with 99:1 cyclohexane:EtOAc afforded the title compound as a colourless oil (18 mg).

LC/MS: m/z 529.2 [M+H]$^+$, R$_t$4.7 min.

Intermediate 4: Methyl {4-[(butyl{6-[4-(trifluoromethyl)phenyl]pyridin-2-yl}amino)methyl]-2-methylphenoxy}acetate

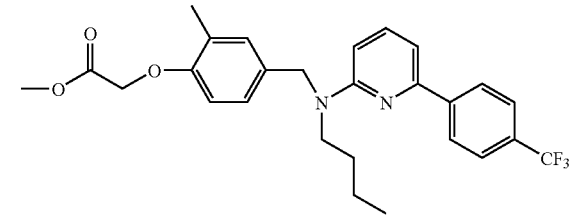

Palladium (II) acetate (5.4 mg, 0.024 mmol) and (S)-2,2'-bis(diphenylphosphino)-1,1'-binapthyl (22 mg, 0.036 mmol) in anhydrous toluene (1.2 mL) were stirred together at 70° C. in a sealed reactivial for 30 minutes. The vial was then allowed to attain room temperature before the methyl {4-[(butylamino)methyl]-2-methylphenoxy}acetate (96 mg, 0.36 mmol), 2-bromo-6-[4-(trifluoromethyl)phenyl]pyridine (90.6 mg, 0.3 mmol) and caesium carbonate (137 mg, 0.42 mmol) were added. The vial was then sealed and heated at 80° C. for 18 h. The reaction mixture was allowed to cool to room temperature, the reaction mixture filtered and the solvent removed in vacuo. Purification by SPE (Silica, 10 g) eluting 99:1–50:1 cyclohexane:EtOAc afforded the title compound as a colourless oil (50 mg).

LC/MS: m/z 487.3 [M+H]$^+$, R$_t$4.5 min.

Intermediate 5: Ethyl 2-(4-formyl-2-methylphenoxy)-2-methylpropanoate

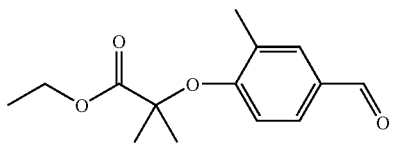

To a solution of 4-hydroxy-3-methyl benzaldehyde (3 g, 22 mmol) and ethyl 2-bromo-2-methylpropionate (6.5 mL, 44 mmol) in DMF (100 mL) was added caesium carbonate (15.8 g, 48 mmol). The resulting mixture was heated at 40° C. for 42 h, then allowed to cool to room temperature. The reaction mixture was diluted with water (200 mL) and extracted with EtOAc (2×150 mL). The organic solution was dried (MgSO$_4$), filtered and evaporated. Purification by Biotage™ chromatography (Silica, 90 g) eluting 9:1 cyclohexane:EtOAc afforded the title compound as a pale yellow oil (3.5 g).

$^1$H NMR (400 MHz; CDCl$_3$) δ: 1.21 (3H, t, J 7 Hz), 1.68 (6H, s) 2.29 (3H, s), 4.23 (2H, q, J 7 Hz), 6.68 (1H, d, J 8 Hz), 7.59 (1H, dd, J 8, 2 Hz), 7.70 (1H, d, J 2 Hz), 9.85 (1H, s).

Intermediate 6: Ethyl (4-formyl-2-methylphenoxy)acetate

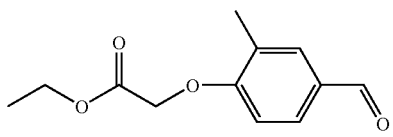

To a solution of 4-hydroxy-3-methylbenzaldehyde (8 g, 58.8 mmol) in an hydrous acetonitrile (300 mL), under nitrogen at 0° C., was added caesium carbonate (21 g, 64.6 mmol) and ethyl bromoacetate (6.52 mL, 58.8 mmol). The resulting mixture was allowed to come to room temperature and stirred for 16 h. The reaction mixture was diluted with water (400 mL) and extracted with EtOAc (2×500 mL). The combined organic extracts were dried (MgSO$_4$) and the solvents removed in vacuo, to afford the title compound as brown solid (11.5 g).

LC/MS: m/z 223.2 [M+H]$^+$, R$_t$ 2.8 min.

Intermediate 7: Ethyl {4-[(butylamino)methyl]-2-methylphenoxy}acetate

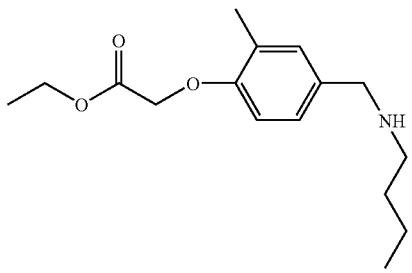

To a solution of ethyl (4-formyl-2-methylphenoxy)acetate (3 g, 13.5 mmol) in anhydrous ethanol (50 mL) at room temperature, was added n-butylamine (1.6 mL, 16.2 mmol) and 4A molecular sieves. The resultant mixture was stirred at room temperature for 18 h under nitrogen, prior to portion wise addition of sodium triacetoxyborohydride (3.43 g, 16.2 mmol). After a further 3 h stirring at room temperature, the reaction was quenched by cautious addition of sat. sodium bicarbonate solution (40 mL) and then diluted with water (50 mL), before extracting with EtOAc (2×100 mL). The combined organic extracts were dried (MgSO$_4$) and the solvents removed in vacuo, to afford the title compound as brown oil (2.6 g).

LC/MS: m/z 280.2 [M+H]$^+$, R$_t$ 2.2 min.

Intermediate 8: Ethyl {2-methyl-4-[(propylamino)methyl]phenoxy}acetate

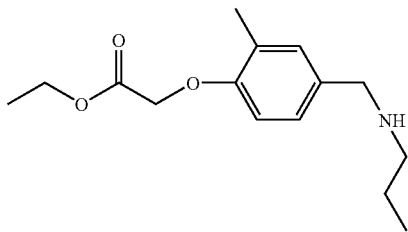

Prepared using n-propyl amine (1.67 mL, 20.3 mmol) and the synthetic procedure described for Intermediate 7. Purification of the crude product by SCX SPE (5×10 g) loading and washing with EtOH and then eluting product with 5% NH$_3$ in EtOH, and removal of the solvent in vacuo yielded the title compound as a brown oil (2.4 g).

LC/MS: m/z 266.2 [M+H]$^+$, R$_t$ 2.08 min.

Intermediate 9: Ethyl (4-{[(2-methoxyethyl)amino]methyl}-2-methyl phenoxy)acetate

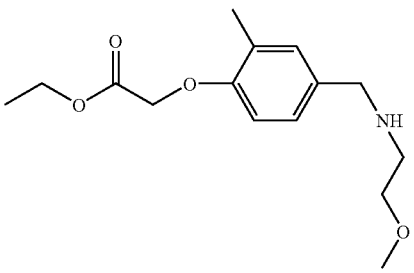

Prepared using 2-methoxyethylamine (1.4 mL, 16.2 mmol) and the synthetic procedure described for Intermediate 7. Purification of the crude product by SCX SPE (5×10 g) loading and washing with EtOH and then eluting product with 5% NH$_3$ in EtOH, and removal of the solvent in vacuo yielded the title compound as a brown oil (1.8 g).

LC/MS: m/z 282.1 [M+H]$^+$, R$_t$2.0 min.

Intermediate 10: Ethyl 2-methyl-2-[2-methyl-4-({[4-(trifluoromethyl)benzyl]amino}methyl)phenoxy]propanoate

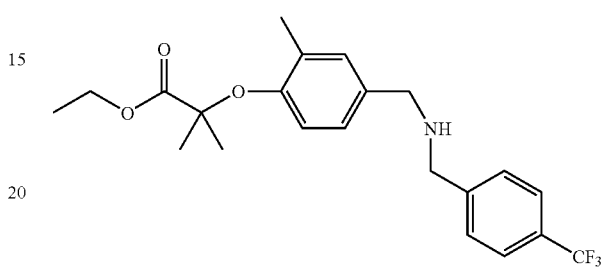

To a solution of ethyl 2-(4-formyl-2-methylphenoxy)-2-methylpropanoate (0.563 g, 2.25 mmol) in CH$_2$Cl$_2$ (10 mL) under nitrogen at room temperature, was added 4-trifluoromethylbenzyl amine (0.34 mL, 2.37 mmol). The resulting solution was stirred for 30 minutes prior to addition of sodium triacetoxyborohydride (0.668 g, 3.15 mmol). After 18 h stirring the reaction mixture was quenched by cautious addition of sat. sodium bicarbonate aq. (30 mL) and extracted CH$_2$Cl$_2$ (2×50 mL). The organic solution was dried (MgSO$_4$) and the solvent removed in vacuo. Purification by SPE (Silica, 20 g) eluting 9:1 cyclohexane:EtOAc afforded the title compound as a colourless oil (0.485 g).

LC/MS: m/z 410.2 [M+H]$^+$, R$_t$2.9 min.

Intermediate 11: Ethyl 2-{4-[(butylamino)methyl]-2-methylphenoxy}-2-methylpropanoate

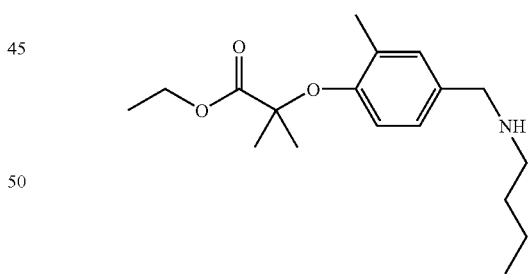

To a solution of ethyl 2-(4-formyl-2-methylphenoxy)-2-methylpropanoate (0.56 g, 2.25 mmol) in anhydrous CH$_2$Cl$_2$ (10 mL) was added n-butylamine (0.33 mL, 3.38 mmol). After stirring for 90 mins under nitrogen at room temperature, sodium triacetoxyborohydride (0.668 g, 3.15 mmol) was added and stirring continued for 18 h. The reaction was quenched by cautious addition of sat. sodium carbonate aq. (20 mL) and then extracted CH$_2$Cl$_2$ (2×40 mL). The organic solution was dried (MgSO$_4$) and the solvents removed in vacuo to afford the title compound as a pale yellow oil (0.48 g).

LC/MS: m/z 308.2 [M+H]$^+$, R$_t$2.5 min.

Intermediate 12: Methyl {4-[(butylamino)methyl]-2-methylphenoxy}acetate

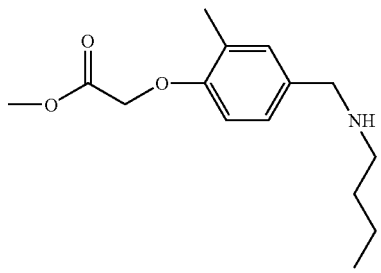

To a solution of ethyl (4-formyl-2-methylphenoxy)acetate (0.65 g, 2.93 mmol) in anyhdrous methanol (12 mL) under nitrogen was added n-butylamine (0.3 mL, 3.07 mmol) and the resultant mixture stirred for 18 h at room temperature, prior to portion wise addition of sodium borohydride (0.144 g, 3.8 mmol). After 30 minutes stirring at room temperature the reaction was quenched by cautious addition of sat. sodium bicarbonate aq. and then extracted into ethyl acetate (2×40 mL). The organic solution was dried (MgSO$_4$) and the solvents removed in vacuo to afford the title compound as a pale yellow oil (0.65 g).

LC/MS: m/z 266.1 [M+H]$^+$, R$_t$2.1 min.

Intermediate 13: 4-(Hydroxymethyl)-2-methylphenol

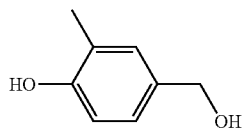

To a solution of 4-hydroxy-3-methylbenzaldehyde (10 g, 73.5 mmol) in dry CH$_2$Cl$_2$ (550 mL) under nitrogen at 5° C. was added tetra-N-butylammonium borohydride (20.58 g, 80 mmol) and the resultant mixture stirred for 1.25 h at 5° C. Saturated ammonium chloride solution (30 mL) was added to the reaction mixture and the resultant mixture stirred for 1 h at 5° C. Saturated ammonium chloride solution (60 mL) was added and the reaction mixture extracted with CH$_2$Cl$_2$, dried (Na$_2$SO$_4$) and the solvents removed in vacuo. Purification by flushing through silica (2×150 g) eluting with EtOAc afforded the title compound as an oily yellow solid (8.01 g).

$^1$H NMR (400 MHz; MeOH-d$^4$) δ: 2.19 (3H, s), 4.46 (2H, s), 6.71 (1H, d, J 8 Hz), 6.99 (1H, dd, J 8 Hz, 2 Hz), 7.06 (1H, d, J 2 Hz), OH not observed.

Intermediate 14: Ethyl [4-(hydroxymethyl)-2-methylphenoxy]acetate (Method A)

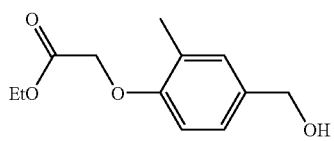

To a solution of 4-(hydroxymethyl)-2-methylphenol (7.95 g, 57 mmol) in dry acetonitrile (300 mL) at 5° C., was added cesium carbonate (20.42 g, 62 mmol) and ethyl bromoacetate (6.38 mL, 57 mmol). The resultant mixture was stirred for 3 h at 5° C. under nitrogen. The reaction mixture was diluted with water (500 mL), extracted with EtOAc (2×750 mL), dried (Na$_2$SO$_4$) and the solvents removed in vacuo to afford the title compound as a yellow oil (12.3 g).

$^1$H NMR (400 MHz; CDCl$_3$) δ: 1.3 (3H, t, J 7 Hz), 2.3 (3H, s), 4.26 (2H, q, J 7 Hz), 4.59 (2H, s), 4.64 (2H, s), 6.68 (1H, d, J 8.5 Hz), 7.12 (1H, dd, J 8.5 Hz, 1.5 Hz), 7.18 (1H, d, J 1.5 Hz), OH not observed.

Intermediate 14: Ethyl [4-(hydroxymethyl)-2-methylphenoxy]acetate (Method B)

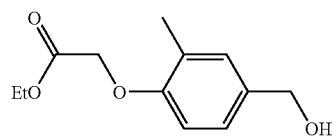

Ethyl (4-formyl-2-methylphenoxy) acetate (29.2 g, 0.131 mol) was dissolved in ethanol (450 mL) and cooled to 10° C. under nitrogen. Sodium borohydride (5.45 g, 0.144 mol) was added over 10 mins to the stirred reaction mixture, and stirred at 10° C. for a further 20 mins. The reaction was cautiously quenched with water/saturated NaHCO$_3$ (3:1, 25 mL) and then diluted with water/brine (3:1, 730 mL) and extracted with EtOAc (2×730 mL). The combined organic extract was washed with brine (1 L), dried (Na$_4$SO$_4$) and concentrated in vacuo. The residue was diluted with dichloromethane (400 mL) washed with water (250 mL) and brine (250 mL), dried (Na$_4$SO$_4$), and concentrated in vacuo to give the title compound as a brown oil (28.2 g).

$^1$H NMR (400 MHz; CDCl$_3$) δ: 1.30 (3H, t, J 7 Hz), 2.31 (3H, s), 4.27 (2H, q, J 7 Hz), 4.60 (2H, s), 4.64 (2H, s), 6.69 (1H, d, J 8.5 Hz), 7.13 (1H, dd, J 8.5 Hz, 1.5 Hz), 7.18 (1H, d, J 1.5 Hz), OH not observed.

Intermediate 15: Ethyl [4-(bromomethyl)-2-methylphenoxy]acetate

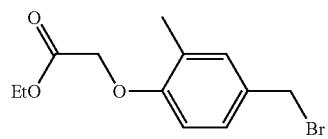

To a solution of ethyl [4-(hydroxymethyl)-2-methylphenoxy]acetate (4.27 g, 19 mmol) in dry CH$_2$Cl$_2$ (150 mL) under nitrogen at 5° C., was added tetrabromomethane (6.91 g, 20.9 mmol) then triphenylphosphine (5.71 g, 21.8 mmol) portion wise over 0.5 h. The resultant mixture was then stirred for 16 h at room temperature. The solvents were removed in vacuo. Purification by Biotage™ chromatography (silica, 2×90 g) eluting with 30:1 cyclohexane:EtOAc afforded the title compound as a yellow solid (2.95 g).

$^1$H NMR (400 MHz; CDCl$_3$) δ: 1.3 (3H, t, J 7 Hz), 2.28 (3H, s), 4.26 (2H, q, J 7 Hz), 4.47 (2H, s), 4.63 (2H, s), 6.64 (1H, d, J 8.5 Hz), 7.16 (1H, dd, J 8.5 Hz, 2 Hz) 7.2 (1H, d, J 2 Hz).

Intermediate 16: 4'-(Trifluoromethyl)-1,1'-biphenyl-3-ylamine

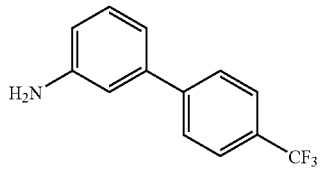

To a solution of 3-iodoaniline in DME (40 mL) and water (20 mL), was added para-trifluoromethylphenyl boronic acid (2.6 g, 13.7 mmol) and sodium carbonate (2.5 g, 23.6 mmol). The apparatus was flushed with nitrogen prior to the addition of tetrakis (triphenylphosphine) palladium (0) (0.312 g, 0.27 mmol). The reaction mixture was stirred at 95° C. for 17 h under nitrogen, then allowed to cool to rt and the solvents removed in vacuo. The residue was partitioned between EtOAc (2×75 mL) and water (75 mL). The organic solution was dried (MgSO$_4$) and the solvent was removed in vacuo. Purification by Biotage™ chromatography (90 g Silica column) eluted with 1:4 EtOAc:cyclohexane afforded the title compound as a white solid (1.33 g).

$^1$H NMR (400 MHz; CDCl$_3$) δ: 6.73 (1H, ddd, J 8 Hz, 2.5 Hz, 1 Hz), 6.90 (1H, m), 6.99 (1H, dm, J 7.5 Hz), 7.26 (1H, m), 7.66 (4H, s), NH$_2$ not observed.

Intermediate 17: N-Butyl-N-[4'-(trifluoromethyl)-1,1'-biphenyl-3-yl]amine

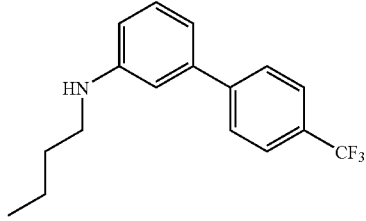

To a solution of butyraldehyde (0.114 mL, 1.26 mmol) in anhydrous CH$_2$Cl$_2$ under nitrogen, was added 4'-(trifluoromethyl)-1,1'-biphenyl-3-ylamine (0.3 g, 1.26 mmol). After 15 mins sodium triacetoxyborohydride (0.375 g, 1.77 mmol) was added portion wise, followed by acetic acid (0.072 mL, 1.26 mmol). After stirring the mixture for 18 h the reaction was quenched by cautious addition of sat. sodium bicarbonate aq. (20 mL) and extracted with CH$_2$Cl$_2$ (2×30 mL). The organic extract was separated by hydrophobic frit and the solvents removed in vacuo. Purification by SPE (Silica, 10 g) eluting with 99:1 cyclohexane:EtOAc, afforded the title compound as a colourless oil (0.25 g).

LC/MS: m/z 293.8 [M+H]$^+$, R$_t$4.1 min

Intermediate 18: N-(2-Methoxyethyl)-N-[4'-(trifluoromethyl)-1,1'-biphenyl-3-yl]amine

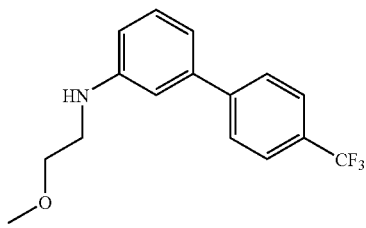

A solution of methoxyacetaldehyde dimetylacetal (0.162 mL, 1.26 mmol) in 0.5 M HCl aq. (2.52 mL, 1.26 mmol) was heated to 50° C. and stirred under nitrogen for 1 h. The reaction mixture was allowed to cool to room temperature and extracted with CH$_2$Cl$_2$ (10 mL). The organic extract was separated by hydrophobic frit and dried by standing over molecular sieves for 2 h. To this solution was added 4'-(trifluoromethyl)-1,1'-biphenyl-3-ylamine (0.3 g, 1.26 mmol), then after 20 minutes sodium triacetoxyborohydride (0.375 g, 1.77 mmol) and acetic acid (0.072 mL, 1.26 mmol) were added. The resultant mixture was stirred at room temperature under nitrogen for 18 h. The reaction was quenched by cautious addition of sat. NaHCO$_3$ aq. (30 mL) and extracted into CH$_2$Cl$_2$ (2×30 mL). The organic extract was passed through a hydrophobic frit and the solvents removed in vacuo. Purification by Biotage™ chromatography eluting with 19:1 cyclohexane:EtOAc afforded the title compound as a pale yellow oil (0.1 g).

$^1$H NMR (400 MHz; CDCl$_3$) δ: 3.35 (2H, t, J 5 Hz), 3.41 (3H, s), 3.64 (2H, t, J 5 Hz), 4.2 (1H, br. s), 6.68 (1H, dm, J 8 Hz), 6.83 (1H, t, J 2 Hz), 6.94 (1H, dm, J 8 Hz), 7.27 (1H, t, J 8 Hz), 7.97 (4H, s).

Intermediate 19: N-Pentyl-N-[4'-(trifluoromethyl)-1,1'-biphenyl-3-yl]amine

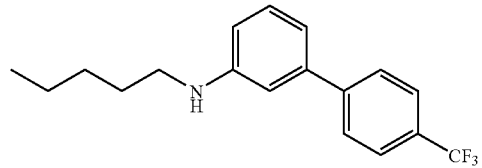

To a solution of 4'-(trifluoromethyl)-1,1'-biphenyl-3-ylamine (0.3 g, 1.26 mmol) in anhydrous CH$_2$Cl$_2$ (10 mL) under nitrogen at room temperature was added valeraldehyde (0.134 mL, 1.26 mmol), sodium triacetoxyborohydride (0.374 g, 1.76 mmol) and acetic acid (72 μl, 1.26 mmol). The resultant mixture was stirred for 17 h at room temperature. The reaction mixture was quenched with sat. NaHCO$_3$ aq. (15 mL), then extracted with CH$_2$Cl$_2$ (2×20 mL). The organic solution was dried (Na$_2$SO$_4$) and the solvent was removed in vacuo. Purification by SPE (20 g Silica column) eluted with 1:200 EtOAc:cyclohexane afforded the title compound as a colourless oil (0.17 g).

LC/MS: m/z 308.1 [M+H]$^+$, R$_t$4.3 min.

Intermediate 20: N-Propyl-N-[4'-(trifluoromethyl)-1,1'-biphenyl-3-yl]amine

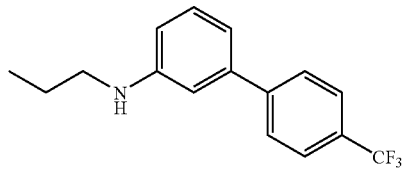

Prepared using propionaldehyde (91 μl, 1.26 mmol) and the synthetic procedure described for Intermediate 19. Purification by Biotage™ chromatography (40 g Silica column), eluted with 1:50 EtOAc:cyclohexane afforded the title compound as a white crystalline solid (0.22 g).

LC/MS: m/z 279.9 [M+H]$^+$, R$_t$4.0 min.

Intermediate 21: N-[2-(Methylthio)ethyl]-N-[4'-(trifluoromethyl)-1,1'-biphenyl-3-yl]amine

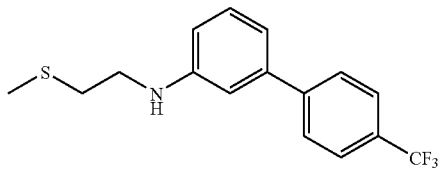

A solution of 2-(methylthio)-acetaldehyde diethyl acetal (0.465 g, 2.83 mmol) in 0.5 M HCl (5.66 mL, 2.83 mmol) was heated to 50° C. and stirred under nitrogen for 1 h. The reaction mixture was allowed to cool and extracted with CH$_2$Cl$_2$ (20 mL). The organic solution was dried (hydrophobic frit), and stood over molecular sieves for 2 h then decanted off into a clean flask. To this solution was added 4'-(trifluoromethyl)-1,1'-biphenyl-3-ylamine (0.67 g, 2.83 mmol) followed by sodium triacetoxyborohydride (1.68 g, 7.93 mmol) and acetic acid (0.162 mL, 2.83 mmol). The resultant mixture was stirred at room temperature under nitrogen for 16 h. The reaction was quenched with sat. NaHCO$_3$ aq. (30 mL) and extracted with CH$_2$Cl$_2$ (2×40 mL), the organic solution was passed through a hydrophobic frit and the solvent removed in vacuo. Purification by Biotage™ chromatography (90 g Silica column) eluted with 1:19 EtOAc:cyclohexane afforded the title compound as a pale yellow oil (397 mg).

$^1$H NMR (400 MHz; CDCl$_3$) δ: 2.13 (3H, s), 2.81 (2H, t, J 6.5 Hz), 3.40 (2H, t, J 6.5 Hz), 4.23 (1H, br.s), 6.68 (1H, d, J 8 Hz), 6.83 (1H, t, J 2 Hz), 6.95 (1H, d, J 7.5 Hz), 7.28 (1H, t, J 8 Hz), 7.67 (4H, s).

Intermediate 22: N-(2-Cyclopropylethyl)-N-[4'-(trifluoromethyl)-1,1'-biphenyl-3-yl]amine

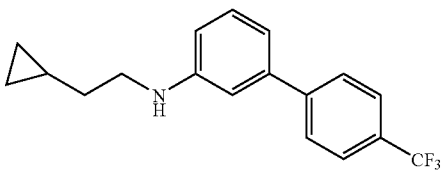

To a solution of oxalyl chloride (0.17 mL, 1.95 mmol) in anhydrous CH$_2$Cl$_2$ (5 mL) under nitrogen at −78° C. was added dropwise a solution of anhydrous DMSO (0.18 mL, 2.6 mmol) in anhydrous CH$_2$Cl$_2$ (2.5 mL), ensuring the temperature remained below −60° C. To this was added a solution of 2-cyclopropyl ethanol (0.132 g, 1.3 mmol) in anhydrous CH$_2$Cl$_2$ (2.5 mL), again ensuring temperature remained below −60° C. The reaction mixture was stirred at −78° C. for 20 mins, then treated with triethylamine (0.543 mL, 3.9 mmol) in anhydrous CH$_2$Cl$_2$ (3 mL). The resultant mixture was allowed to gradually warm to room temperature and stirred for 16 h. The reaction mixture was diluted with CH$_2$Cl$_2$ (10 mL) and water (5 mL) prior to the addition of 2M HCl (0.5 mL). The mixture was stirred vigorously for 20 mins, then passed through a hydrophobic frit. The organic solution was stood over molecular sieves for 2 h, then decanted into a clean flask. To this solution was added 4'-(trifluoromethyl)-1,1'-biphenyl-3-ylamine (0.31 g, 1.3 mmol), followed by sodium triacetoxyborohydride (0.386 g, 1.82 mmol) and acetic acid (74.3 μL, 1.3 mmol). The resultant mixture was stirred at room temperature under nitrogen for 20 h. The reaction mixture was quenched with sat. NaHCO$_3$ aq. (15 mL) and extracted with CH$_2$Cl$_2$ (2×20 mL). The organic solution was passed through a hydrophobic frit and the solvent was removed in vacuo. Purification by SPE (20 g Silica column) eluted with 1:200 EtOAc:cyclohexane afforded the title compound as a colourless oil (255 mg).

LC/MS: m/z 306.2 [M+H]$^+$ R$_t$ 4.1 min.

Intermediate 23: Ethyl [4-({butyl[4'-(trifluoromethyl)-1,1'-biphenyl-3-yl]amino}methyl)-2-methylphenoxy]acetate

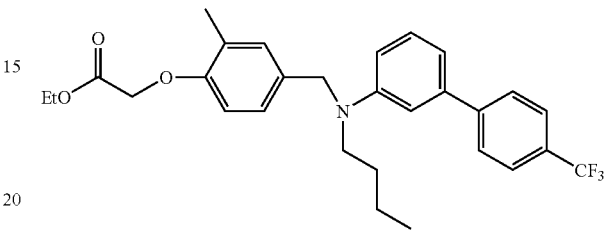

To a solution of N-butyl-N-[4'-(trifluoromethyl)-1,1'-biphenyl-3-yl]amine (73 mg, 0.25 mmol) in anhydrous acetonitrile (5 mL) was added ethyl [4-(bromomethyl)-2-methylphenoxy]acetate (75 mg, 0.25 mmol) and N,N-diisopropylethylamine (43 μL, 0.25 mmol). The resulting solution was heated at reflux under nitrogen for 2 h and then cooled to room temperature. The solvent was removed in vacuo and the residue diluted with water (10 mL) and extracted with CH$_2$Cl$_2$ (30 mL). The organic extract was separated by hydrophobic frit and the solvent removed in vacuo. Purification by SPE (Silica, 5 g) eluting 99:1 cyclohexane:EtOAc afforded the title compound as a pale yellow oil (105 mg).

$^1$H NMR (400 MHz; CDCl$_3$) δ: 0.96 (3H, t, J 7.5 Hz), 1.28 (3H, t, J 7 Hz), 1.38 (2H, m), 1.67 (2H, m), 2.27 (3H, s), 3.43 (2H, t, 7.5 Hz), 4.25 (2H, q, J 7 Hz), 4.50 (2H, s), 4.61 (2H, s), 6.64 (1H, d, J 8 Hz), 6.71 (1H, dd, J 8 Hz, 2 Hz), 6.80–6.90 (2H, m), 6.98 (1H, d, J 8 Hz), 7.04 (1H, m), 7.26 (1H, m), 7.59 (2H, d, J 8.5 Hz), 7.64 (2H, d, J 8.5 Hz).

LC/MS: m/z 500.2 [M+H]$^+$, R$_t$ 4.5 min.

Intermediate 24: Ethyl [4-({(2-methoxyethyl)[4'-(trifluoromethyl)-1,1'-biphenyl-3-yl]amino}methyl)-2-methylphenoxy]acetate

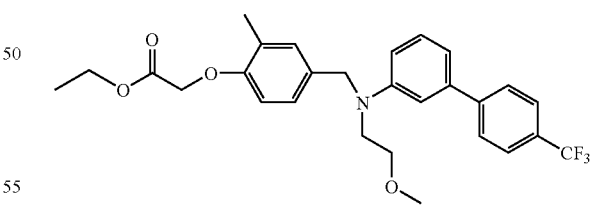

To a solution of N-(2-methoxyethyl)-N-[4'-(trifluoromethyl)-1,1'-biphenyl-3-yl]amine (0.1 g, 0.34 mmol) in anhydrous acetonitrile (10 mL) was added ethyl [4-(bromomethyl)-2-methylphenoxy]acetate (0.097 g, 0.34 mmol) and N,N-diisopropylethylamine (0.059 mL, 0.34 mmol). The resulting mixture was heated to reflux and stirred under nitrogen for 3 h. The reaction mixture was concentrated in vacuo and the residue partitioned between water (20 mL) and CH$_2$Cl$_2$ (40 mL), the organic extract was separated by hydrophobic frit and the solvents removed in vacuo. Purification by Biotage™ chromatography (Silica, 12 g) eluting 9:1 cyclohexane:EtOAc afforded the title compound as a colourless oil (90 mg).

¹H NMR (400 MHz; CDCl₃) δ: 1.28 (3H, t J 7 Hz), 2.27 (3H, s), 3.36 (3H, s), 3.60–3.70 (4H, m), 4.24 (2H, q, J 7 Hz), 4.57 (2H, s), 4.61 (2H, s), 6.64 (1H, d, J 8.5 Hz), 6.76 (1H, d, J 8.5 Hz), 6.87–6.93 (2H, m), 6.99 (1H, d, J 8 Hz), 7.05 (1H, s), 7.26 (1H, m), 7.59 (2H, d, J 8 Hz), 7.64 (2H, d, J 8 Hz).

Intermediate 25: Ethyl [2-methyl-4-({pentyl[4'-(trifluoromethyl)-1,1'-biphenyl-3-yl]amino}methyl)phenoxy]acetate

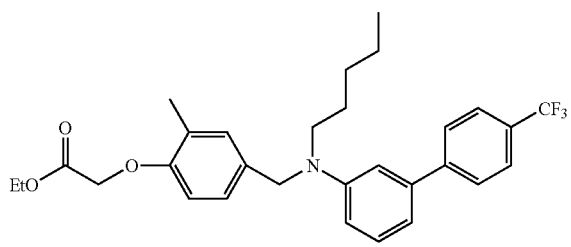

To a solution of N-pentyl-N-[4'-(trifluoromethyl)-1,1'-biphenyl-3-yl]amine (70 mg, 0.23 mmol) in anhydrous MeCN (6 mL) under nitrogen at room temperature, was added ethyl [4-(bromomethyl)-2-methylphenoxy]acetate (65.4 mg, 0.23 mmol) and N,N-diisopropyethylamine (39.6 μL, 0.23 mmol). The resultant solution was heated to reflux and stirred for 4 h. The reaction mixture was allowed to cool to room temperature and the solvent was removed in vacuo. The residue was partitioned between CHCl₃ (20 mL) and water (10 mL). The organic solution was passed through a hydrophobic frit and the solvent was removed in vacuo. Purification by SPE (5 g Silica cartridge) eluted with 1:200–1:100 EtOAc:cyclohexane afforded the title compound as a colourless oil (66 mg).

¹H NMR (400 MHz; CDCl₃) δ: 0.91 (3H, t, J 7 Hz), 1.28 (3H, t, J 7 Hz), 1.31–1.38 (4H, m), 1.68 (2H, m), 2.27 (3H, s), 3.41 (2H, t, J 7.5 Hz), 4.25 (2H, q, J 7 Hz), 4.49 (2H, s), 4.61 (2H, s), 6.64 (1H, d, J 8 Hz), 6.71 (1H, dd, J 8.5 Hz, 2.5 Hz), 6.82–6.88 (2H, m), 6.98 (1H, m), 7.05 (1H, s), 7.26 (1H, m), 7.59 (2H, d, J 8.5 Hz), 7.64 (2H, d, J 8.5 Hz).

Intermediate 26: Ethyl [4-({(2-cyclopropylethyl)[4'-(trifluoromethyl)-1,1'-biphenyl-3-yl]amino}methyl)-2-methylphenoxy]acetate

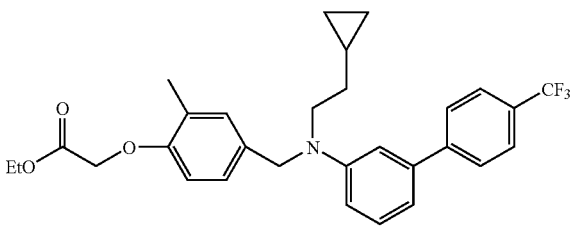

To a solution of N-(2-cyclopropylethyl)-N-[4'-(trifluoromethyl)-1,1'-biphenyl-3-yl]amine (100 mg, 0.33 mmol) in anhydrous MeCN (7 mL) under nitrogen at room temperature was added ethyl [4-(bromomethyl)-2-methylphenoxy]acetate (94 mg, 0.33 mmol) and N,N-diisopropyethylamine (57.5 μl, 0.33 mmol). The resultant solution was heated to reflux and stirred for 2.5 h. The reaction mixture was allowed to cool to room temperature and the solvent was removed in vacuo. The residue was partitioned between CHCl₃ (2×10 mL) and water (10 mL). The organic solution was passed through a hydrophobic frit and the solvent was removed in vacuo. Purification by SPE (5 g Silica cartridge) eluted with 1:200–1:100 EtOAc:cyclohexane afforded the title compound as a colourless oil (141 mg).

¹H NMR (400 MHz; CDCl₃) δ: 0.08 (2H, m), 0.47 (2H, m), 0.69 (1H, m), 1.28 (3H, t, J 7.5 Hz), 1.56 (2H, m), 2.28 (3H, s), 3.55 (2H, t, J 7.5 Hz), 4.25 (2H, q, J 7 Hz), 4.51 (2H, s), 4.61 (2H, s), 6.64 (1H, d, J 8.5 Hz), 6.71 (1H, m), 6.83–6.88 (2H, m), 6.99 (1H, m), 7.05 (1H, s), 7.25 (1H, m), 7.59 (2H, d, J 8.5 Hz), 7.65 (2H, d, J 8.5 Hz).

Intermediate 27: Ethyl [2-methyl-4-({propyl[4'-(trifluoromethyl)-1,1'-biphenyl-3-yl]amino}methyl)phenoxy]acetate

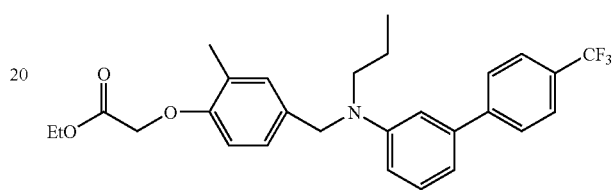

To a solution of N-propyl-N-[4'-(trifluoromethyl)-1,1'-biphenyl-3-yl]amine (69.8 mg, 0.25 mmol) in anhydrous MeCN (6 mL) under nitrogen at room temperature, was added ethyl [4-(bromomethyl)-2-methylphenoxy]acetate (71.8 mg, 0.25 mmol) and N,N-diisopropyethylamine (43.5 μL, 0.25 mmol). The resultant mixture was heated to reflux and stirred for 3 h. The reaction mixture was allowed to cool to room temperature and the solvent was removed in vacuo. The residue was partitioned between CHCl₃ (2×10 mL) and water (10 mL). The organic solution was passed through a hydrophobic frit and the solvent was removed in vacuo. Purification by SPE (5 g Silica cartridge eluted with 1:200 EtOAc:cyclohexane afforded the title compound as a colourless oil (88 mg).

¹H NMR (400 MHz; CDCl₃) δ: 0.95 (3H, t, J 7.5 Hz), 1.28 (3H, t, J 7 Hz), 1.71 (2H, m), 2.27 (3H, s), 3.39 (2H, t, J 8 Hz), 4.25 (2H, q, J 7 Hz), 4.51 (2H, s), 4.61 (2H, s), 6.64 (1H, d, J 8.5 Hz), 6.71 (1H, dd, J 8 Hz, 2.5 Hz), 6.84 (1H, m), 6.86 (1H, d, J 7.5 Hz), 6.99 (1H, dd, J 8.5 Hz, 2 Hz), 7.05 (1H, d, J 1.5 Hz), 7.26 (1H, m) 7.59 (2H, d, J 8 Hz), 7.64 (2H, d, J 8 Hz).

Intermediate 28: Methyl 2-methyl-4-({[2-(methylthio)ethyl][4'-(trifluoromethyl)-1,1'-biphenyl-3-yl]amino}methyl)phenoxy]acetate

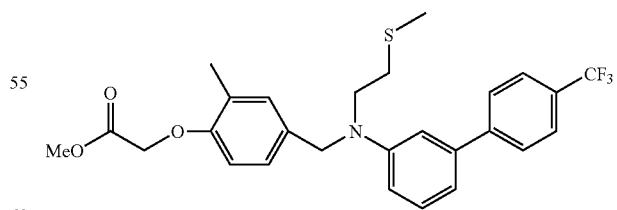

To a solution of N-[2-(methylthio)ethyl]-N-[4'-(trifluoromethyl)-1,1'-biphenyl-3-yl]amine (0.27 g, 0.864 mmol) in anhydrous MeCN (22 mL) under nitrogen at room temperature was added methyl [4-(bromomethyl)-2-methylphenoxy]acetate (0.248 g, 0.864 mmol) and N,N-diisopropyethylamine (0.15 mL, 0.864 mmol). The resultant mixture was heated to reflux and stirred for 3 h. The reaction mixture was allowed to cool to room temperature and the solvent was removed in vacuo. The residue was partitioned between CHCl₃ (2×30 mL) and water (30 mL). The organic solution was passed through a hydrophobic frit and the solvent was removed in vacuo. Purification by SPE (20 g Silica cartridge), eluted with 1:99–1:33 EtOAc:cyclohexane afforded the title compound as a yellow oil (249 mg).

LC/MS: m/z 504.4 [M+H]⁺ R$_t$ 4.2 min.

Intermediate 29: 2-Methyl-4'-(trifluoromethyl)-1,1'-biphenyl-3-ylamine

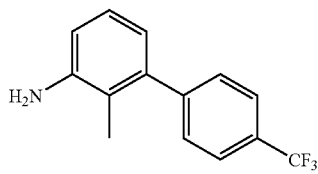

To a solution of 3-bromo-2-methylaniline (1.19 g, 6.4 mmol) in DME (30 mL) and water (15 mL) was added para-trifluoromethylphenyl boronic acid (1.82 g, 9.6 mmol) and sodium carbonate (1.76 g, 16.6 mmol). The apparatus was flushed with nitrogen prior to the addition of tetrakis (triphenylphosphine) palladium (0) (0.22 g, 0.19 mmol). The resultant mixture was heated to reflux and stirred under nitrogen for 17 h, then allowed to cool to room temperature and the solvents removed in vacuo. The residue was partitioned between EtOAc (2×60 mL) and water (60 mL). The organic solution was dried (MgSO₄) and the solvent was removed in vacuo. Purification by Biotage™ chromatography (90 g Silica column) eluted with 1:4 EtOAc:cyclohexane afforded the title compound as a cream coloured solid (1.27 g).

LC/MS: m/z 252.2 [M+H]⁺; m/z 293.3 [M+CH₃CN]⁺, R$_t$ 3.6 min.

Intermediate 30: N-Butyl-N-[2-methyl-4'-(trifluoromethyl)-1,1'-biphenyl-3-yl]amine

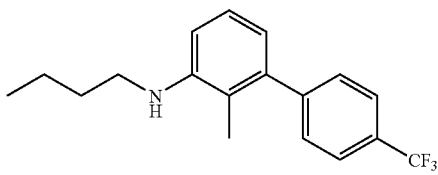

To a solution of 2-methyl-4'-(trifluoromethyl)-1,1'-biphenyl-3-ylamine (0.32 g, 1.26 mmol) in anhydrous CH₂Cl₂ (10 mL) under nitrogen at room temperature was added butyraldehyde (0.114 mL, 1.26 mmol), followed 10 min later by sodium triacetoxyborohydride (0.374 g, 1.76 mmol) and acetic acid (72 μL, 1.26 mmol). The resultant mixture was stirred for 22 h at room temperature. The reaction mixture was quenched with sat. NaHCO₃ aq. (15 mL), then extracted with CH₂Cl₂ (2×20 mL). The organic solution was passed through a hydrophobic frit and the solvent was removed in vacuo. Purification by SPE (20 g Silica cartridge) eluted with 1:200 EtOAc:cyclohexane afforded the title compound as a colourless oil (221 mg).

LC/MS: m/z 308 [M+H]⁺, R$_t$ 4.3 min.

Intermediate 31: N-(2-Methoxyethyl)-2-methyl-4'-(trifluoromethyl)-1,1'-biphenyl-3-amine

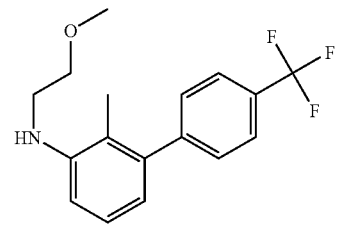

1,1,2-trimethoxyethane (0.162 mL, 1.26 mL) was added to 0.5N HCl (2.52 mL, 1.26 mmol) and the resultant solution heated for 1 h at 50° C. The cooled reaction mixture was extracted with CH₂Cl₂. The organic solution was passed through a hydrophobic frit, dried for 2 h (3A molecular sieves). 2-Methyl-4'-(trifluoromethyl)-1,1'-biphenyl-3-ylamine (0.32 g, 1.26 mmol) was added to the organic solution and the solution stirred for 20 min at rt. Sodium triacetoxyborohydride (0.325 g, 1.77 mmol) and acetic acid (0.072 mL, 1.26 mmol) were then added, and the resultant mixture stirred for 16 h at rt. Saturated sodium bicarbonate was added to the reaction mixture and once effervescence had ceased the mixture was extracted with CH₂Cl₂. The organic solution was passed through a hydrophobic frit and the solvents removed in vacuo. Purification by Biotage™ chromatography (silica, 40 g) eluted with 10% EtOAc/cyclohexane afforded the title compound (42 mg).

¹H NMR (400 MHz; CDCl₃) δ: 2.02 (3H, s), 3.38 (2H, t, J 5.5 Hz), 3.42 (3H, s), 3.69 (2H, t, J 5.5 Hz), 4.0 (1H, s, broad), 6.63 (1H, d, J 8 Hz), 6.68 (1H, d, J 8 Hz), 7.18 (1H, t, J 8 Hz), 7.41 (2H, d, J 8 Hz), 7.65 (2H, d, J 8 Hz).

Intermediate 32: Ethyl [4-({butyl[2-methyl-4'-(trifluoromethyl)-1,1'-biphenyl-3-yl]amino}methyl)-2-methylphenoxy]acetate

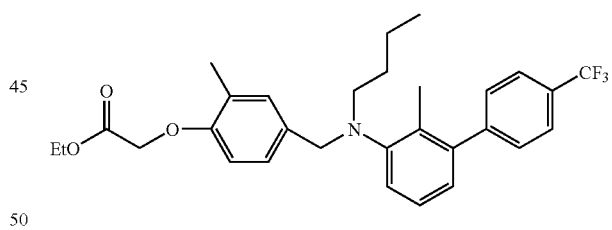

To a solution of N-butyl-N-[2-methyl-4'-(trifluoromethyl)-1,1'-biphenyl-3-yl]amine (102 mg, 0.33 mmol) in anhydrous MeCN (8 mL) under nitrogen at room temperature was added ethyl [4-(bromomethyl)-2-methylphenoxy] acetate (95.3 mg, 0.33 mmol) and N,N-diisopropyethylamine (57.8 μL, 0.33 mmol). The resultant solution was heated to reflux and stirred for 3 h. The reaction mixture was allowed to cool to room temperature and the solvent was removed in vacuo. The residue was partitioned between CHCl₃ (2×10 mL) and water (10 mL). The organic solution was passed through a hydrophobic frit and the solvent was removed in vacuo. Purification by Biotage™ chromatography (40 g Silica column) eluted with 1:99–1:49 EtOAc:cyclohexane afforded the title compound as a colourless oil (110 mg).

Thermospray (positive) m/z 514 [M+H]⁺.

Intermediate 33: Ethyl [4-({(2-methoxyethyl)[2-methyl-4'-(trifluoromethyl)-1,1'-biphenyl-3-yl]amino}methyl)-2-methylphenoxy]acetate

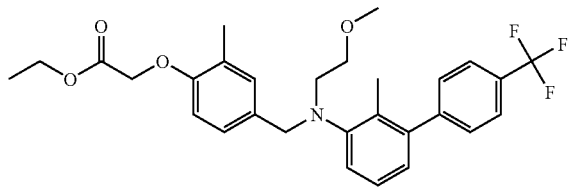

To a solution of N-(2-methoxyethyl)-2-methyl-4'-(trifluoromethyl)-1,1'-biphenyl-3-amine (500 mg, 1.62 mmol) in acetonitrile (30 mL) was added ethyl [4-(bromomethyl)-2-methylphenoxy]acetate (488 mg, 1.7 mmol) and N,N-diisopropylethylamine (295 μl, 1.7 mmol). The resultant mixture was heated for 4.5 h at 80° C. On cooling the solvents were removed in vacuo, the residue diluted with water and extracted with CH$_2$Cl$_2$. The organic solution was passed through a hydrophobic frit and the solvent removed in vacuo. Purification by Biotage™ chromatography (silica, 40 g) eluted with 5% EtOAc/cyclohexane afforded the title compound as a colourless oil (503 mg).

$^1$H NMR (400 MHz; CDCl$_3$) δ: 1.29 (3H, t, J 7 Hz), 2.22 (3H, s), 2.26 (3H, s), 3.16 (2H, t, J 6.5 Hz), 3.25 (3H, s), 3.39 (2H, t, J 6.5 Hz), 4.10 (2H, s), 4.26 (2H, q, J 7 Hz), 4.61 (2H, s), 6.62 (1H, d, J 8 Hz), 6.95 (1H, dd, J 7 Hz, 1.5 Hz), 7.05–7.09 (2H, m), 7.15–7.22 (2H, m), 7.42 (2H, d, J 8 Hz), 7.66 (2H, d, J 8 Hz).

Intermediate 34: Ethyl [2-methyl-4-({[4'-(trifluoromethyl)-1,1'-biphenyl-3-yl]amino}methyl)phenoxy]acetate

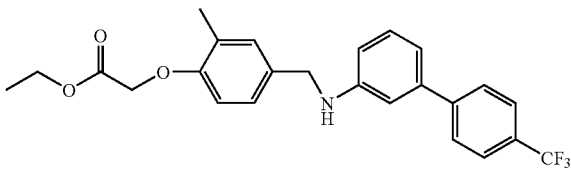

To a solution of ethyl (4-formyl-2-methylphenoxy)acetate (0.2 g, 0.9 mmol) in anhydrous CH$_2$Cl$_2$ (8 mL) was added 4'-(trifluoromethyl)-1,1'-biphenyl-3-ylamine (0.214 g, 0.9 mmol). The resulting mixture was stirred under nitrogen at room temperature for 15 mins, prior to addition of sodium triacetoxyborohydride (0.267 g, 1.26 mmol) and acetic acid (0.052 mL, 0.9 mmol). The resultant mixture was stirred for 18 h prior to quenching by cautious addition of sat. sodium bicarbonate solution (20 mL) the reaction mixture was then extracted CH$_2$Cl$_2$ (20 mL). The organic extract separated by hydrophobic frit and the solvent removed in vacuo. Purification by Biotage™ chromatography (Silica, 40 g) eluting 9:1 cyclohexane:EtOAc afforded the title compound as a colourless oil (0.342 g).

LC/MS: m/z 444.3 [M+H]$^+$, R$_t$ 4.1 min

Intermediate 35: Ethyl [4-({butyryl[4'-(trifluoromethyl)-1,1'-biphenyl-3-yl]amino}methyl)-2-methylphenoxy]acetate

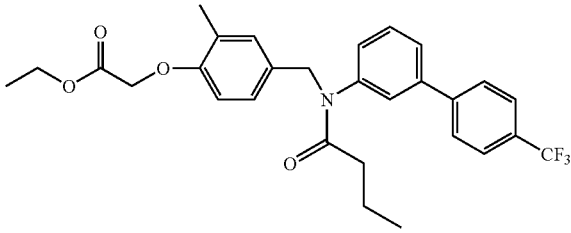

To a solution of ethyl [2-methyl-4-({[4'-(trifluoromethyl)-1,1'-biphenyl-3-yl]amino}methyl)phenoxy]acetate (0.07 g, 0.16 mmol) in anhydrous CH$_2$Cl$_2$ (2 mL) at 0° C. under nitrogen was added butyric acid (0.016 mL, 0.17 mmol), 1-(3-dimethylaminopropyl)-3-ethylcarbodimide hydrochloride (33 mg, 0.17 mmol) was then added in portions followed by triethylamine (0.022 mL, 0.16 mmol). After stirring for 15 mins at 0° C. the reaction was allowed to attain room temperature and stirred for 18 h. The reaction mixture was diluted with CH$_2$Cl$_2$ (20 mL) and shaken with 1 M HCl (5 mL). The organic extract was separated by hydrophobic frit and the solvent removed in vacuo. Purification by Biotage™ chromatography (Silica, 12 g) eluting 9:1 cyclohexane:EtOAc afforded the title compound as a colourless oil (40 mg).

LC/MS: m/z 513.9 [M+H]$^+$, R$_t$ 4.0 min.

Intermediate 36: Ethyl [2-methyl-4-({(propylsulfonyl)[4'-(trifluoromethyl)-1,1'-biphenyl-3-yl]amino}methyl)phenoxy]acetate

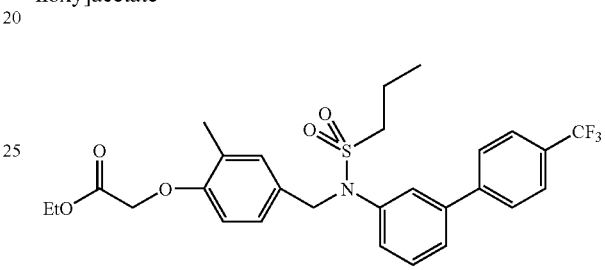

To a reactivial containing ethyl [2-methyl-4-({[4'-(trifluoromethyl)-1,1'-biphenyl-3-yl]amino}methyl)phenoxy]acetate (100 mg, 0.225 mmol) was added pyridine (0.321 mL, 3.97 mmol) and 1-propanesulfonyl chloride (25.3 μL, 0.225 mmol). The resulting mixture was stirred in a sealed reactivial at 80° C. for 16 h. The reaction mixture was allowed to cool to room temperature and was partitioned between CH$_2$Cl$_2$ (2×10 mL) and water (10 mL). The organic solution was passed through a hydrophobic frit and the solvent was removed in vacuo. Purification by Biotage™ chromatography (12 g Silica column) eluted with 1:9 EtOAc:cyclohexane afforded the title compound as a yellow oil (20 mg).

LC/MS: m/z 567.1 [M+NH$_4$]$^+$ R$_t$ 3.9 min.

Intermediate 37: Ethyl [4-({butyl[4'-(trifluoromethyl)-1,1'-biphenyl-3-yl]amino}sulfonyl)-2-methylphenoxy]acetate

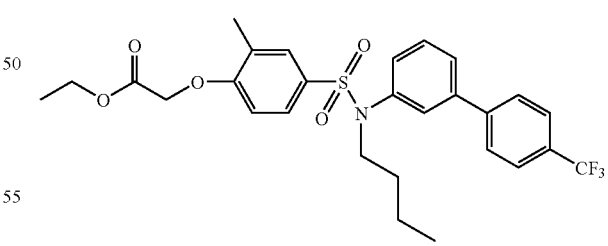

To a solution of N-butyl-N-[4'-(trifluoromethyl)-1,1'-biphenyl-3-yl]amine (0.128 g, 0.44 mmol) In anhydrous CH$_2$Cl$_2$ (10 mL) was added ethyl [4-(chlorosulfonyl)-2-methylphenoxy]acetate (0.121 g, 0.41 mmol) and triethylamine (0.122 mL, 0.87 mmol). The resultant mixture was stirred for 24 h at room temperature prior to addition of sulfonyl chloride (0.121 mg, 0.41 mmol) and triethylamine (0.122 mL, 0.87 mmol). After a further 18 h stirring at room temperature the reaction was diluted with water (10 mL) and extracted with CH$_2$Cl$_2$ (2×10 mL). The organic solution was dried (Na$_2$SO$_4$) and the solvents removed in vacuo. Purification by SPE (Silica, 10 g) eluting 49:1–19:1 cyclohexane:EtOAc afforded the title compound as a pale yellow oil (0.182 g).

LC/MS: m/z 550.3 [M+H]$^+$, R$_t$ 4.2 min

Intermediate 38: Ethyl [2-methyl-4-({pentyl[4'-(trifluoromethyl)-1,1'-biphenyl-3-yl]amino}sulfonyl)phenoxy]acetate

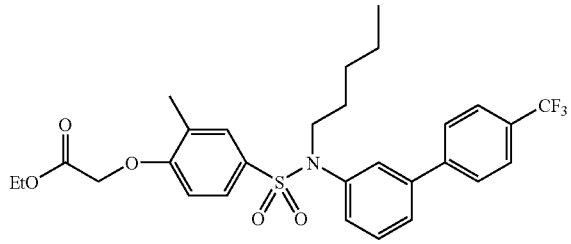

To a solution of N-pentyl-N-[4'-(trifluoromethyl)-1,1'-biphenyl-3-yl]amine (70.6 mg, 0.23 mmol) in CH$_2$Cl$_2$ (5 mL) under nitrogen at room temperature was added ethyl [4-(chlorosulfonyl)-2-methylphenoxy]acetate (101 mg, 0.35 mmol) and triethylamine (96 μL, 0.69 mmol). The resultant mixture was stirred for 24 h at room temperature. The reaction mixture was extracted with CH$_2$Cl$_2$ (15 mL) and water (10 mL). The organic solution was passed through a hydrophobic frit and the solvent was removed in vacuo. Purification by SPE (5 g Silica cartridge) eluted with 1:49–1:19 EtOAc:cyclohexane afforded the title compound as a white crystalline solid (76 mg).

LC/MS: m/z 564.4 [M+H]$^+$ R$_t$ 4.3 min.

Intermediate 39: Ethyl [4-({(2-cyclopropylethyl)[4'-(trifluoromethyl)-1,1'-biphenyl-3-yl]amino}sulfonyl)-2-methylphenoxy]acetate

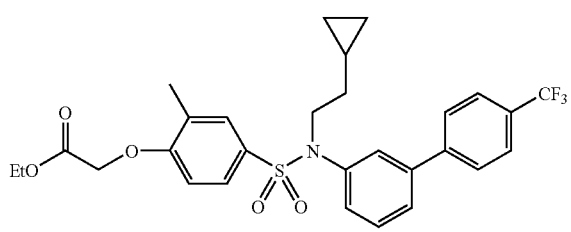

To a solution of N-(2-cyclopropylethyl)-N-[4'-(trifluoromethyl)-1,1'-biphenyl-3-yl]amine (155 mg, 0.51 mmol) in anhydrous CH$_2$Cl$_2$ (10 mL) under nitrogen at room temperature was added ethyl [4-(chlorosulfonyl)-2-methylphenoxy]acetate (223 mg, 0.76 mmol) and triethylamine (0.213 mL, 1.53 mmol). The resultant mixture was stirred for 40 h at room temperature. The reaction mixture was diluted with water (15 mL) and extracted with CH$_2$Cl$_2$ (30 mL). The organic solution was passed through a hydrophobic frit and the solvent was removed in vacuo. Purification by Biotage™ chromatography (40 g Silica column) eluted with 1:19–1:9 EtOAc:cyclohexane afforded the title compound as a white crystalline solid (156 mg).

LC/MS: m/z 561.8 [M+H]$^+$ R$_t$ 4.3 min.

Intermediate 40: 2-(Methylthio)-4-[4-(trifluoromethyl)phenyl]pyrimidine

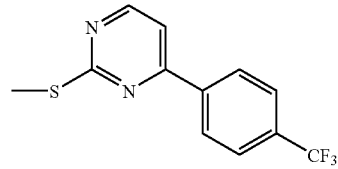

To a solution of 4-chloro-2-methylthiopyrimidine (2.17 mL, 18.7 mmol) in dimethoxyethane (140 mL) and water (70 mL) was added sodium carbonate (5.15 g, 48.5 mmol), 4-trifluoromethylphenylboronic acid and tetrakis(triphenylphosphine) palladium (0) (0.43 g). The resulting mixture was heated at reflux under nitrogen for 18 h, then allowed to cool to room temperature and the dimethoxyethane removed in vacuo. The residue was diluted with water (30 mL) and extracted CH$_2$Cl$_2$ (2×100 mL). The organic solution was dried (MgSO$_4$) and the solvents removed in vacuo. Purification by Biotage™ chromatography (Silica, 90 g) eluting 19:1 cyclohexane:EtOAc yielded the title compound as a pale yellow solid (4.47 g).

LC/MS: m/z 471.0 [M+H]$^+$, R$_t$ 3.7 min.

Intermediate 41: 4-(4-Chlorophenyl)-2-(methylthio)pyrimidine

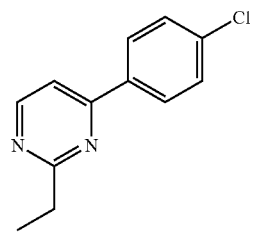

A mixture of 4-chloro-2-(methylthio)pyrimidine (3 g, 18.7 mmol), 4-chloro-phenylboronic acid (3.5 g, 22.3 mmol), tetrakis(triphenylphosphine)palladium (0) (0.43 g, 0.37 mmol), sodium carbonate (5.15 g, 48.5 mmol) in 1,2-dimethoxyethane (140 mL) and water (70 mL) was heated at 90° C. for 20 h under nitrogen. The cooled reaction mixture was concentrated In vacuo, diluted with water (50 mL), extracted with CH$_2$Cl$_2$ (2×100 ml), dried (Na$_2$SO$_4$) and the solvent removed in vacuo. Purification by Biotage™ chromatography (silica, 90 g) eluting with 10:1 to 2:1 cyclohexane:EtOAc afforded the title compound as a white solid (3.98 g).

LC/MS: m/z 237 [M+H]$^+$, R$_t$ 3.56 min.

Intermediate 42: 2-(Methylsulfonyl)-4-[4-(trifluoromethyl)phenyl]pyrimidine

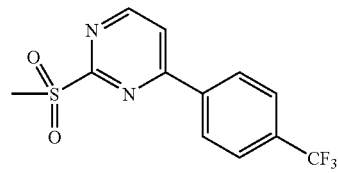

To a suspension of 2-(methylthio)-4-[4-(trifluoromethyl)phenyl]pyrimidine (2.24 g, 8.4 mmol) in methanol (85 mL)

and water (85 mL) at 0° C. was added oxone™ (15.25 g, 24.8 mmol). The reaction was stirred at 0° C. for 1 h and then at room temperature for 18 h. The reaction mixture was diluted with water (200 mL) and extracted with chloroform (2×250 mL). The organic solution was dried (Na₂SO₄) filtered and evaporated to afford the title compound as a white solid (2.235 g).

LC/MS: m/z 302.8 [M+H]⁺, R,3.1 min

Intermediate 43: 4-(4-Chlorophenyl)-2-(methylsulfonyl) pyrimidine

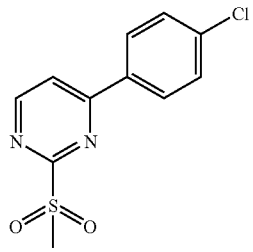

A solution of 4-(4-chlorophenyl)-2-(methylthio)pyrimidine (3 g, 12.71 mmol), in methanol (125 mL) and water (125 mL) under nitrogen at 4° C. was treated with oxone™ (23.44 g, 38.13 mmol), stirred and allowed to warm up to room temperature for 18 h. The reaction mixture was diluted with water (220 mL), extracted with CHCl₃ (250 mL), dried (Na₂SO₄) and the solvent removed in vacuo to afford the title compound as a yellow solid (3.36 g).

LC/MS: m/z 269 [M+H]⁺, R, 2.82 min.

Intermediate 44: Ethyl {4-[(butyl{4-[4-(trifluoromethyl) phenyl]pyrimidin-2-yl}amino)methyl]-2-methylphenoxy}acetate

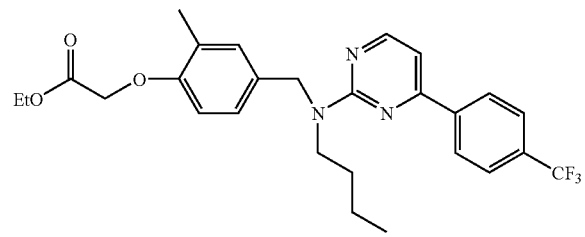

A mixture of 2-(methylsulfonyl)-4-[4-(trifluoromethyl) phenyl]pyrimidine (0.3 g, 1 mmol), N,N-diisopropylethylamine (0.18 mL, 1 mmol) and ethyl {4-[(butylamino) methyl]-2-methylphenoxy}acetate (0.424 g, 1.53 mmol) was heated at 100° C. in a sealed reactivial for 18 h. The residue was dissolved in CH₂Cl₂ and purified by Biotage™ chromatography (Silica, 40 g) eluting 3:97 EtOAc:cyclohexane to afford the title compound as a pale yellow oil (110 mg).

¹H NMR (400 MHz; CDCl₃) δ: 0.94 (3H, t, J 7 Hz), 1.28 (3H, t, J 7 Hz), 1.37 (2H, m), 1.64 (2H, m), 2.26 (3H, s),3.63 (2H, t, J7.5 Hz), 4.25 (2H, q, J 7 Hz), 4.61 (2H, s), 4.88 (2H, s), 6.63 (1H, d, J 8.5 Hz), 6.94 (1H, d, J 5.5 Hz), 7.04 (1H, d, J 8.5 Hz), 7.09 (1H, s), 7.70 (2H, d, J 8 Hz), 8.13 (2H, br d, J 8 Hz),8.42 (1H, d, J 5.5 Hz).

Intermediate 45: Ethyl [4-({butyl[4-(4-chlorophenyl)pyrimidin-2-yl]amino}methyl)-2-methylphenoxy]acetate

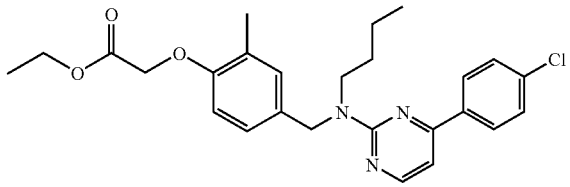

To a mixture of the ethyl {4-[(butylamino)methyl]-2-methylphenoxy}acetate (686 mg, 2.46 mmol) and N,N-diisopropylethylamine (285 µL, 1.64 mmol) was added 4-(4-chlorophenyl)-2-(methylsulfonyl)pyrimidine (439 mg, 1.64 mmol) and the resultant mixture heated at 100° C. for 16 h in a reactivial. The cooled reaction mixture were then treated with N,N-diisopropylethylamine (285 µL, 1.64 mmol) and heated for a further 16 h at 100° C. in the reactivial. The cooled reaction mixtures were diluted with CH₂Cl₂ (30 mL), washed with water (20 mL), the aqueous extracted with CH₂Cl₂ (30 mL), the CH₂Cl₂ extracts combined and the solvent removed in vacuo. Purification by Biotage™ chromatography (silica, 90 g) eluted with 10:1 cyclohexane:EtOAc gave the title compound as a colourless gum (178 mg).

¹H NMR (400 MHz; CDCl₃) δ: 0.95 (3H, t, J 7.5 Hz), 1.3 (3H, t, J 7 Hz), 1.37 (2H, m), 1.64 (2H, m), 2.27 (3H, s), 3.63 (2H, t, J 7.5 Hz), 4.26 (2H, q, J 7 Hz), 4.62 (2H, s), 4.89 (2H, s), 6.64 (1H, d, J 8.5 Hz), 6.90 (1H, d, J 5 Hz), 7.03–7.13 (2H, m), 7.43 (2H, d, J 8.0 Hz), 8.00 (2H, d, J 8.0 Hz), 8.39 (1H, d, J 5 Hz).

LC/MS: m/z 468 [M+H]⁺, R, 4.34 min

Intermediate 46: Ethyl {4-[((2-methoxyethyl){4-[4-(trifluoromethyl)phenyl]pyrimidin-2-yl}amino)methyl]-2-methylphenoxy}acetate

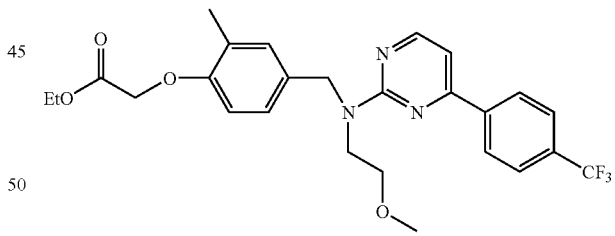

A mixture of 2-(methylsulfonyl)-4-[4-(trifluoromethyl) phenyl]pyrimidine (0.2 g, 0.66 mmol), N,N-diisopropylethylamine (0.11 mL, 0.66 mmol) and ethyl (4-{[(2-methoxyethyl)amino]methyl}-2-methylphenoxy)acetate (0.28 g. 0.99 mmol) was heated at 100° C. in a sealed reactivial for 20 h. The reaction mixture was then allowed to come to room temperature, and the residue dissolved in CH₂Cl₂ (30 mL), the organic extract was washed water (20 mL) and passed through a hydrophobic frit before concentrating in vacuo. Purification by Biotage™ chromatography (Silica, 90 g) eluting 1:9 EtOAc:cyclohexane afforded the title compound as a pale yellow oil (0.08 g).

LC/MS: m/z 503.8 [M+H]⁺, R,4.1 min.

Intermediate 47: Ethyl (4-{[[4-(4-chlorophenyl)pyrimidin-2-yl](2-methoxyethyl)amino]methyl}-2-methylphenoxy)acetate

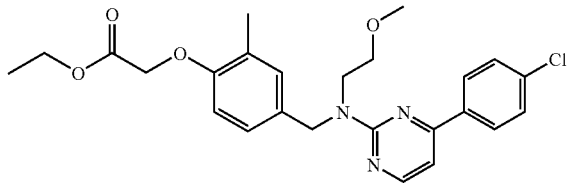

Prepared from ethyl (4-{[(2-methoxyethyl)amino]methyl}-2-methylphenoxy)acetate using the synthetic procedure described for Intermediate 45. Purification by Biotage™ chromatography (silica, 90 g) eluted with 100:15 to 100:25 cyclohexane:EtOAc afforded the title compound as a colourless gum (165 mg).

$^1$H NMR (400 MHz; CDCl$_3$) δ: 1.28 (3H, t, J 7 Hz), 2.26 (3H, s), 3.34 (3H, s), 3.63 (2H, t, J 5.5 Hz), 3.83 (2H, t, J 5.5 Hz), 4.25 (2H, q, J 7 Hz), 4.6 (2H, s), 4.96 (2H, s), 6.63 (1H, d, J 8 Hz), 6.92 (1H, d, J 5 Hz), 7.06 (1H, d, J 8 Hz), 7.11 (1H, s), 7.42 (2H, d, J 8.5 Hz), 7.98 (2H, d, J 8.5 Hz), 8.39 (1H, d, 5 Hz).

LC/MS: m/z 470 [M+H]$^+$, R$_t$ 3.98 min

Intermediate 48: Ethyl {2-methyl-4-[(propyl{4-[4-(trifluoromethyl)phenyl]pyrimidin-2-yl}amino)methyl]phenoxy}acetate

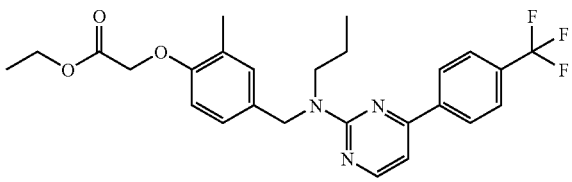

To a mixture of ethyl {2-methyl-4-[(propylamino)methyl]phenoxy}acetate (652 mg, 2.46 mmol) and N,N-diisopropylethylamine (570 μL, 3.28 mmol) was added 2-(methylsulfonyl)-4-[4-(trifluoromethyl)phenyl]pyrimidine (495 mg, 1.64 mmol) and the resultant mixture heated at 100° C. for 16 h in a reactivial. The cooled reaction mixture was diluted with CH$_2$Cl$_2$ (30 mL), washed with water (20 mL), the aqueous extracted with CH$_2$Cl$_2$ (30 mL) and the CH$_2$Cl$_2$ extracts combined and the solvent removed in vacuo. Purification by Biotage™ chromatography (silica, 90 g) eluted with cyclohexane:EtOAc 10:1 afforded the title compound as a colourless gum (139 mg).

$^1$H NMR (400 MHz; CDCl$_3$) δ: 0.95 (3H, t, J 7.5 Hz), 1.30 (3H, t, J 7 Hz), 1.69 (2H, m), 2.28 (3H, s), 3.61 (2H, t, J 7.5 Hz), 4.26 (2H, q, J 7 Hz), 4.62 (2H, s), 4.9 (2H, s), 6.65 (1H, d, J 8 Hz), 6.95 (1H, d, J 5 Hz), 7.06 (1H, d, J 8 Hz), 7.11 (1H, s), 7.72 (2H, d, J 8 Hz), 8.145 (2H, d, J 8 Hz), 8.44 (1H, d, J 5 Hz).

LC/MS: m/z 488 [M+H]$^+$, R$_t$ 4.24 min.

Intermediate 49: 2-Chloro-6-[4-(trifluoromethyl)phenyl]pyrazine

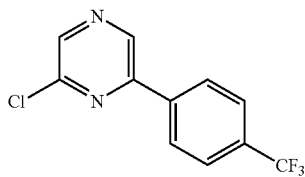

To a mixture of 2,6-dichloropyrazine (0.5 g, 3.36 mmol), sodium carbonate (0.925 g, 8.73 mmol) and 4-trifluoromethylphenylboronic acid (0.638 g, 3.36 mmol) in dimethoxyethane (15 mL) and water (7.5 mL) under nitrogen was added tetrakis(triphenylphosphine) palladium (0) (0.078 g). The resulting mixture was heated at reflux for 5 h under nitrogen, before stirring at room temperature overnight. The reaction was diluted with water (50 mL) and extracted with chloroform (2×75 mL). The organic solution was dried (MgSO$_4$) and the solvents removed in vacuo. Purification by Biotage™ chromatography (Silica, 90 g) 10:1–6:1 cyclohexane:EtOAc afforded the title compound as a white solid (0.317 g).

$^1$H NMR (400 MHz; CDCl$_3$) δ: 7.78 (2H, d, J 8 Hz), 8.16 (2H, d, J 8 Hz), 8.61 (1H, s), 8.98 (1H, s).

Intermediate 50: 2-Chloro-6-(4-methylphenyl)pyrazine

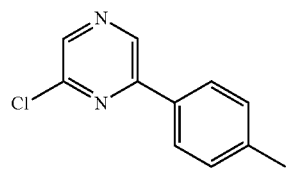

To a mixture of 2,6-dichloropyrazine (3 g, 20 mmol), sodium carbonate (5.55 g, 52 mmol) and 4-methylphenylboronic acid (2.74 g 20 mmol) in dimethoxyethane (90 mL) and water (45 mL) under nitrogen was added tetrakis(triphenylphosphine) palladium (0) (0.46 g). The resulting mixture was heated at reflux for 18 h under nitrogen. After cooling to room temperature, the reaction was diluted with water (100 mL) and extracted with chloroform (2×150 mL). The organic solution was dried MgSO$_4$ and the solvents removed in vacuo. Purification by Biotage™ chromatography (Silica, 90 g) 9:1 cyclohexane:EtOAc afforded the title compound as a white solid (2.3 g).

LC/MS: m/z 205.1 [M+H]$^+$, R$_t$ 3.4 min.

Intermediate 51: 2-Bromo-6-[4-(trifluoromethyl)phenyl]pyrazine

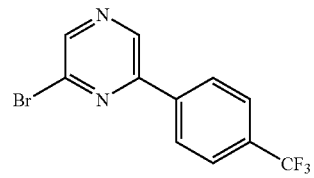

To a flask containing 2-chloro-6-[4-(trifluoromethyl)phenyl]pyrazine (0.8 g, 3.1 mmol), was added phosphorus tribromide (20 mL) and the mixture heated at reflux for 6 h under nitrogen. The reaction mixture was cooled to room temperature prior to pouring carefully into iced water (400 mL), the resulting mixture was adjusted to pH 6–7 using aqueous ammonia and extracted with diethylether (3×250 mL). The organic solution was dried (MgSO$_4$) and the solvent removed in vacuo to afford the title compound as a pale yellow crystalline solid (0.97 g).

$^1$H NMR (400 MHz; CDCl$_3$) δ: 7.78 (2H, d, J 8 Hz), 8.15 (2H, J 8 Hz), 8.69 (1H, s), 8.99 (1H, s).

Intermediate 52: 2-Bromo-6-(4-methylphenyl)pyrazine

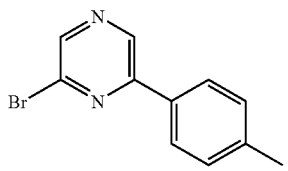

To a flask containing 2-chloro-6-(4-methylphenyl)pyrazine (2.5 g, 12.3 mmol), was added phosphorus tribromide (20 mL) and the mixture heated at reflux for 6 h under nitrogen. The reaction mixture was cooled to room temperature prior to pouring carefully into iced water (600 mL). The resulting solution was adjusted to pH 6–7 using aqueous ammonia and extracted with Et$_2$O (2×250 mL). The organic solution was dried (MgSO$_4$) and the solvent removed in vacuo to afford the title compound as a white solid (2.32 g).

LC/MS: m/z 249.0, 251.0 [M+H]$^+$, R$_t$3.4 min.

Intermediate 53: Ethyl {4-[(butyl{6-[4-(trifluoromethyl)phenyl]pyrazin-2-yl}amino)methyl]-2-methylphenoxy}acetate

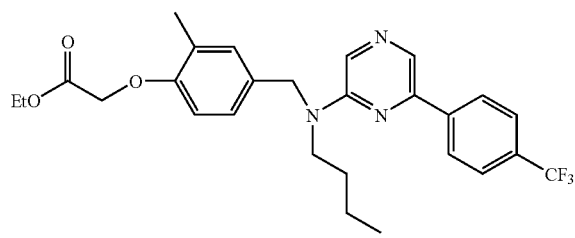

A mixture of 2-bromo-6-[4-(trifluoromethyl)phenyl]pyrazine (0.5 g, 1.6 mmol), N,N-diisopropylethylamine (0.29 mL, 1.6 mmol) and ethyl {4-[(butylamino)methyl]-2-methylphenoxy}acetate (0.5 g, 1.8 mmol) was heated at 100° C. in a sealed reactivial for 18 h. The reaction mixture was then allowed to come to room temperature, and the residue dissolved in CH$_2$Cl$_2$ (130 mL), the organic extract was washed water (30 mL) passed through a hydrophobic frit and concentrated in vacuo. Purification by Biotage™ chromatography (Silica, 90 g) eluting 1:19–1:4 EtOAc:cyclohexane afforded the title compound as a pale yellow oil (0.15 g).

LC/MS: m/z 501.8 [M+H]$^+$, R$_t$4.3 min.

Intermediate 54: Ethyl [4-({butyl[6-(4-methylphenyl)pyrazin-2-yl]amino}methyl)-2-methylphenoxy]acetate

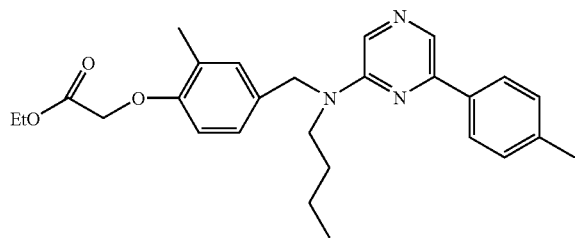

A mixture of 2-bromo-6-(4-methylphenyl)pyrazine (0.25 g, 1 mmol), N,N-diisopropylethylamine (0.35 mL, 2 mmol) and ethyl {4-[(butylamino)methyl]-2-methylphenoxy}-acetate (0.42 g, 1.5 mmol) was heated at 100° C. in a sealed reactivial for 18 h. The reaction mixture was then allowed to come to room temperature and the residue dissolved in CH$_2$Cl$_2$ (30 mL), the organic extract was washed water (15 mL) and passed through a hydrophobic frit before concentrating in vacuo. Purification by Biotage™ chromatography (Silica, 40 g) eluting 1:19–1:4 EtOAc:cyclohexane afforded the title compound as a pale yellow oil (37 mg).

LC/MS: m/z 448.2 [M+H]$^+$, R$_t$4.1 min.

Intermediate 55: Ethyl {4-[((2-methoxyethyl){6-[4-(trifluoromethyl) phenyl]pyrazin-2-yl}amino)methyl]-2-methylphenoxy}acetate

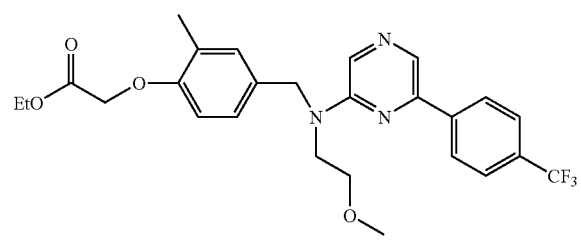

A mixture of 2-bromo-6-[4-(trifluoromethyl)phenyl]pyrazine (0.5 g, 1.65 mmol), N,N-diisopropylethylamine (0.29 mL, 1.65 mmol) and ethyl (4-{[(2-methoxyethyl)amino]methyl}-2-methylphenoxy)acetate (0.7 g, 2.47 mmol) was heated at 100° C. in a sealed reactivial for 20 h. The reaction mixture was then allowed to come to room temperature, and the residue was diluted with water (40 mL) and extracted CH$_2$Cl$_2$ (2×40 mL). The organic extract was passed through a hydrophobic frit and concentrated in vacuo. Purification by Biotage™ chromatography (Silica, 90 g) eluting 1:19–1:4 EtOAc:cyclohexane afforded the title compound as a pale yellow oil (0.16 g).

LC/MS: m/z 503.8 [M+H]$^+$, R$_t$4.0 min.

Intermediate 56: 3-Bromo-2-methyl-N-propylaniline

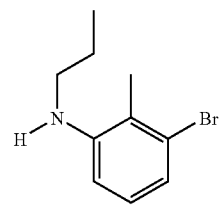

To a solution of 3-bromo-2-methylphenylamine (1.5 g, 8.06 mmol) in dry CH$_2$Cl$_2$ with 3A molecular sieves was added propionaldehyde (580 μL, 8.06 mmol) and the resultant mixture stirred at room temperature for 20 min under nitrogen. Acetic acid (561 μL, 8.06 mmol) and sodium triacetoxyborohydride (4.78 g, 22.56 mmol) were added and the resultant mixture stirred under nitrogen at room temperature for 16 h. Saturated sodium bicarbonate (60 mL) was added portionwise and the resultant mixture stirred for 0.5 h and extracted with CH$_2$Cl$_2$ (2×100 mL). The organic solution was dried (Na$_2$SO$_4$) and the solvents removed in vacuo to afford the title compound as a yellow oil (1.8 g).

LC/MS: m/z 230 [M+H]$^+$, R$_t$ 3.64 min

Intermediate 57: 3-Bromo-N-butyl-2-methylaniline

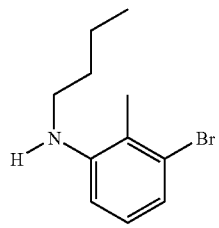

Prepared from butyraldehyde and 3-bromo-2-methylphenylamine using the procedure described Intermediate 56.

LC/MS: m/z 244 [M+H]$^+$, R$_t$ 3.82 min

Intermediate 58: 3-Bromo-N-(2-methoxyethyl)-2-methylaniline

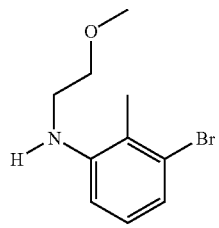

A solution of 1,1,-2-trimethoxyethane (2.07 mL, 16.07 mmol) in 0.5M HCl (32 mL) was heated at 100° C. for 2 h. The cooled mixture was extracted with CH$_2$Cl$_2$ (30 mL) and the organic solution dried (3A molecular sieves). 3-Bromo-2-methylphenylamine was added and the resultant solution stirred under nitrogen for 20 min. Acetic acid (461 µL, 8.05 mmol) and sodium triacetoxyborohydride (4.78 g, 22.56 mmol) were added and the reaction mixture stirred under nitrogen at room temperature for 16 h. Saturated sodium bicarbonate (60 mL) was added portionwise and the resultant mixture stirred for 0.5 h and extracted with CH$_2$Cl$_2$ (2×100 mL). The organic solution was dried (Na$_2$SO$_4$) and the solvents removed in vacuo. Purification by SPE (silica, 2×20 g) eluted with 100:2 to 100:5 cyclohexane:EtOAc afforded the title compound as a yellow oil (687 mg).

LC/MS: m/z 246 [M+H]$^+$, R$_t$ 3.27 min.

Intermediate 59: Ethyl (4-{[(3-bromo-2-methylphenyl)(butyl)amino]methyl}-2-methylphenoxy)acetate

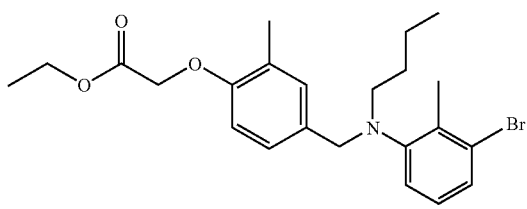

To a solution of 3-bromo-N-butyl-2-methylaniline (700 mg, 2.89 mmol) in dry acetonitrile (75 mL) was added ethyl [4-(bromomethyl)-2-methylphenoxy]acetate (830 mg, 2.89 mmol) and N,N-diisopropylethylamine (331 µL, 1.9 mmol). The resultant mixture was heated at 80° C. for 3 h. The reaction mixture was cooled and the solvents removed in vacuo, diluted with water (50 mL) and extracted with CH$_2$Cl$_2$ (2×100 mL). The organic solution was dried (Na$_2$SO$_4$) and the solvents removed in vacuo. Purification by SPE (silica, 20 g) eluted with 100:2 to 100:5 cyclcohexane:EtOAc afforded the title compound as a colourless oil (749 mg).

LC/MS: m/z 450 [M+H]$^+$, R$_t$ 4.32 min.

Intermediate 60: Ethyl (4-{[(3-bromo-2-methylphenyl)(propyl)amino]methyl}-2-methylphenoxy)acetate

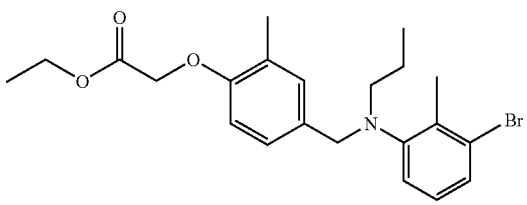

Prepared from 3-bromo-2-methyl-N-propylaniline using the procedure described for Intermediate 59.

LC/MS: m/z 436 [M+H]$^+$, R$_t$ 4.24 min.

Intermediate 61: Ethyl (4-{[(3-bromo-2-methylphenyl)(2-methoxyethyl)amino]methyl}-2-methylphenoxy)acetate

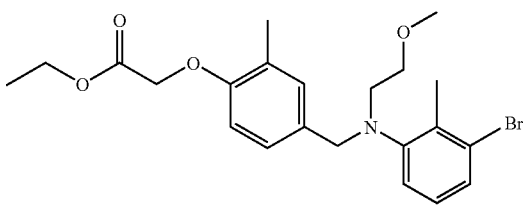

Prepared from 3-bromo-N-(2-methoxyethyl)-2-methylaniline using the procedure described for Intermediate 59.

LC/MS: m/z 452 [M+H]$^+$, R$_t$ 3.92 min.

Intermediate 62: 4-Chloro-5-methyl-6-[4-(trifluoromethyl)phenyl]pyrimidine

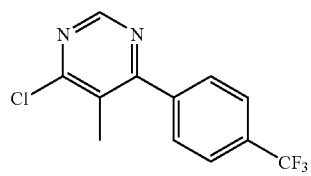

To a solution of 4,6-dichloro-5-methylpyrimidine (1 g, 6.13 mmol) in dimethoxyethane (28 mL) and water (14 mL) was added sodium carbonate (1.69 g, 16.0 mmol), 4-trifluoromethylphenylboronic acid (1.165 g, 6.13 mmol) and tetrakis(triphenylphosphine)palladium (0) (0.14 g). The resulting mixture was heated at reflux under nitrogen for 18 h, the reaction mixture was allowed to cool to room temperature and diluted with water (100 mL) before extraction into CHCl$_3$ (2×100 mL). The organic solution separated by hydrophobic frit and the solvents removed in vacuo. Purification by Biotage™ chromatography (Silica, 90 g) eluting with 19:1 cyclohexane:EtOAc afforded the title compound as a white solid (1.1 g).

LC/MS: m/z 273.1 [M+H]$^+$, R$_t$ 3.3 min.

Intermediate 63: 4-Chloro-6-(4-chlorophenyl)-5-methylpyrimidine

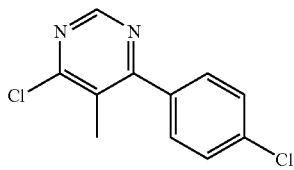

Prepared from 4-chlorophenylboronic acid and 4,6-dichloro-5-methylpyrimidine using the procedure described for Intermediate 62.

LC/MS: m/z 239.1 [M+H]$^+$, R$_t$ 3.2 min.

Intermediate 64: 4-Chloro-5-methyl-6-(4-methylphenyl)pyrimidine

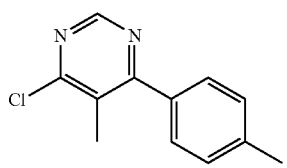

Prepared from 4-methylphenylboronic acid and and 4,6-dichloro-5-methylpyrimidine using the procedure described for Intermediate 62.

LC/MS: m/z 219.1 [M+H]$^+$, R$_t$ 3.2 min.

Intermediate 65: 4-Chloro-6-(4-methoxyphenyl)-5-methylpyrimidine

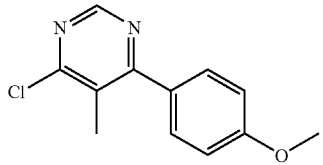

Prepared from 4-methoxyphenylboronic acid (0.93 g, 6.13 mmol) and 4,6-dichloro-5-methylpyrimidine using the procedure described for Intermediate 62.

LC/MS: m/z 235.1 [M+H]$^+$, R$_t$ 3.0 min.

Intermediate 66: Ethyl {4-[(butyl{5-methyl-6-[4-(trifluoromethyl)phenyl]pyrimidin-4-yl}amino)methyl]-2-methylphenoxy}acetate

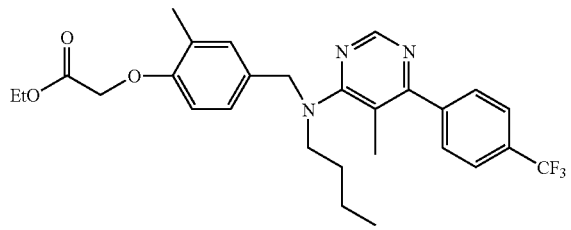

A mixture of 4-chloro-5-methyl-6-[4-(trifluoromethyl)phenyl]pyrimidine (0.229 g, 0.84 mmol), N,N-diisopropylethylamine (0.293 mL, 1.68 mmol) and ethyl {4-[(butylamino)methyl]-2-methylphenoxy}acetate (0.35 g, 1.26 mmol) was heated at 100° C. in a sealed reactivial for 18 h. The reaction mixture was then allowed to come to room temperature, and the residue dissolved in CH$_2$Cl$_2$ (50 mL), the organic extract was washed water (20 mL) and passed through a hydrophobic frit then concentrated in vacuo. Purification by Biotage™ chromatography (Silica, 90 g) eluting with 1:19–1:9 EtOAc:cyclohexane afforded the title compound as a colourless oil (0.19 g).

LC/MS: m/z 516.2 [M+H]$^+$, R$_t$ 3.9 min.

Intermediate 67: Ethyl [4-({butyl[6-(4-methoxyphenyl)-5-methylpyrimidin-4-yl]amino}methyl)-2-methylphenoxy]acetate

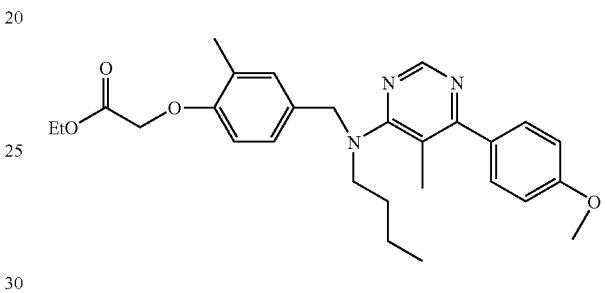

A mixture of 4-chloro-6-(4-methoxyphenyl)-5-methylpyrimidine (0.164 g, 0.7 mmol), diisopropylethylamine (0.24 mL, 1.4 mmol) and ethyl {4-[(butylamino)methyl]-2-methylphenoxy}acetate (0.29 g, 1.05 mmol) was heated at 100° C. in a sealed reactivial for 18 h. The reaction mixture was then allowed to come to room temperature. The residue was dissolved in CH$_2$Cl$_2$ (50 mL), the organic solution was washed water (20 mL) and passed through a hydrophobic frit before concentrating in vacuo. Purification by Biotage™ chromatography (Silica, 90 g) eluting with 3:17–1:4 EtOAc:cyclohexane afforded the title compound as a pale yellow oil (62 mg).

LC/MS: m/z 478.3 [M+H]$^+$, R$_t$ 3.2 min.

Intermediate 68: Ethyl [4-({butyl[6-(4-chlorophenyl)-5-methylpyrimidin-4-yl]amino}methyl)-2-methylphenoxy]acetate

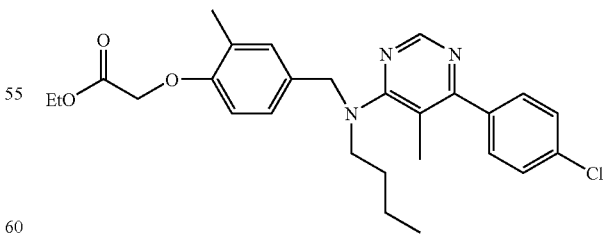

Prepared from 4-chloro-6-(4-chlorophenyl)-5-methylpyrimidine and ethyl {4-[(butylamino)methyl]-2-methylphenoxy}acetate using the procedure of Intermediate 67.

LC/MS: m/z 482.2 [M+H]$^+$, R$_t$ 3.7 min.

Intermediate 69: Ethyl [4-({butyl[5-methyl-6-(4-methylphenyl)pyrimidin-4-yl]amino}methyl)-2-methylphenoxy]acetate

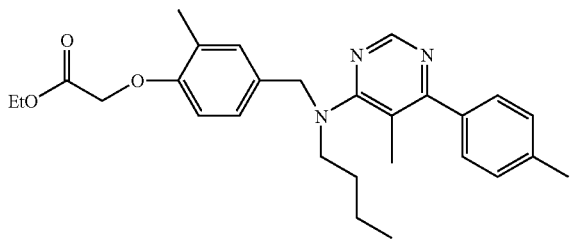

Prepared from 4-chloro-5-methyl-6-(4-methylphenyl)pyrimidine and ethyl {4-[(butylamino)methyl]-2-methylphenoxy}acetate using the procedure of Intermediate 67.

LC/MS: m/z 462.3 [M+H]$^+$, R$_t$ 3.4 min.

Intermediate 70: 2,4'-Dimethyl-1,1'-biphenyl-3-ylamine

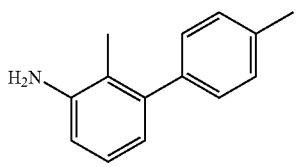

To a solution of 3-bromo-2-methylaniline (15 g, 0.0806 mol) in 1,2-dimethoxyethane (330 ml) and water (165 ml) was added 4-methylphenylboronic acid (12.05 g, 0.0886 mol) and sodium carbonate (22.2 g, 0.2095 mol). The apparatus was flushed with nitrogen prior to the addition of tetrakis(triphenylphosphine) palladium (0) (1.86 g, 1.61 mmol). The resultant mixture was heated at 90° C. and stirred under nitrogen for 22 h, then allowed to cool to room temperature and the solvents removed in vacuo. The residue was partitioned between EtOAc (2×400 ml) and water (400 ml). The organic solution was dried (Na$_2$SO$_4$) and the solvent was removed in vacuo. Purification by Biotage™ chromatography (4×90 g Si column) eluted with 9:1 to 8:1 EtOAc:cyclohexane afforded the title compound as a yellow oil (14.78 g).

LC/MS: m/z 198 [M+H]$^+$, R$_t$ 3.22 min

Intermediate 71: N-(2,4'-Dimethyl-1,1'-biphenyl-3-yl)butanamide

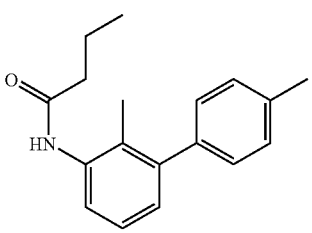

To a solution of 2,4'-dimethyl-1,1'-biphenyl-3-ylamine (20 g, 0.1015 mol) in anhydrous CH$_2$Cl$_2$ (250 ml) at 0° C. under nitrogen was added triethylamine (28.29 ml, 0.203 mol). Butyrylchloride (11.07 ml, 0.1066 mol) was added dropwise over 0.5 h, the rate of addition ensured temperature of reaction mixture was below 10° C. Reaction mixture was then stirred at room temperature for 2 h under nitrogen, diluted with CH$_2$Cl$_2$ (200 ml), washed with water (400 ml), saturated sodium bicarbonate (400 ml) and saturated sodium chloride (400 ml). The organic solution was dried (Na$_2$SO$_4$) and the solvent removed in vacuo to give a cream solid. To the solid was added cyclohexane (400 ml), the mixture stirred for 2 h and filtered. The solid residues were dissolved in CH$_2$Cl$_2$ and the solvents removed in vacuo to afford the title compound as a cream solid (25 g).

LC/MS: m/z 268 [M+H]$^+$, R$_t$ 3.37 min

Intermediate 72: N-Butyl-N-(2,4'-dimethyl-1,1'-biphenyl-3-yl)amine

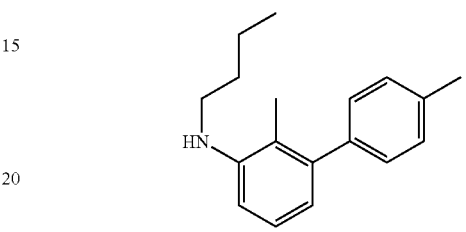

To solution of N-(2,4'-dimethyl-1,1'-biphenyl-3-yl)butanamide (15 g, 0.056 mol) in anhydrous tetrahydrofuran (500 ml) was added dropwise lithiumaluminium hydride (1 M solution in ether; 112 ml) under nitrogen. The resultant mixture was heated at 75° C. for 5.5 h then allowed to cool to room temperature for 16 h. To the reaction mixture was added dropwise wet ether (50 ml), then 2M NaOH (50 ml) and water (50 ml). The mixture was filtered, the solid residues washed with ether and the filtrate dried (Na$_2$SO$_4$), and the solvents removed in vacuo. The residue was partitioned between CH$_2$Cl$_2$ (400 ml) and water (20 ml). The CH$_2$Cl$_2$ layer was dried (Na$_2$SO$_4$) and the solvent removed in vacuo to afford the title compound as a yellow oil (13.12 g).

LC/MS: m/z 254 [M+H]$^+$, R$_t$ 4.07 min

Intermediate 73: Ethyl [4-(chloromethyl)-2-methylphenoxy]acetate

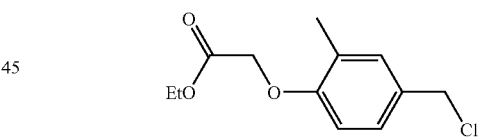

Ethyl [4-(hydroxymethyl)-2-methylphenol (54.1 g, 0.241 mol) was dissolved in dry DCM (540 mL) and cooled to −6° C. under nitrogen. Triethylamine (67 mL, 0.48 mol) was then added over 15 mins. Mesyl chloride (28 mL, 0.362 mol) was then added over 40 min keeping the reaction temperature below 5° C. After the addition was complete the mixture was stirred at 0° C. for 30 mins, before warming to RT and stirring overnight. The reaction was quenched by addition of water (22 mL). Reaction mixture was washed with water (370 mL) and aqueous extracted with DCM (370 mL). The combined organic extracts were dried over Na$_2$SO$_4$ and concentrated in vacuo to give the title compound as an oil, which formed a low melting orange solid when stored at +5° C. (52.05 g).

$^1$H NMR (400 MHz; CDCl$_3$) δ: 1.3 (3H, t, J 7 Hz), 2.29 (3H, s), 4.27 (2H, q, J 7 Hz), 4.54 (2H, s), 4.64 (2H, s), 6.66 (1H, d, J 8.5 Hz), 7.15 (1H, dd, J 8.5 Hz, 2.5 Hz) 7.20 (1H, d, J 2.5 Hz).

Intermediate 74: Ethyl (4-{[butyl(2,4'-dimethyl-1,1'-biphenyl-3-yl)amino]methyl}-2-methylphenoxy)acetate

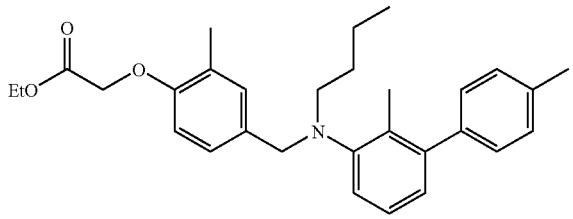

Ethyl [4-(chloromethyl)-2-methylphenoxy]acetate (35.9 g, 0.148 mols) was dissolved in dry acetonitrile (285 mL). Sodium iodide (20.1 g, 0.135 mols 1 eq) was added in one portion and mixture stirred for 5 mins. A solution of the N-butyl-N-(2,4'-dimethyl-1,1'-biphenyl-3-yl)amine (34 g. 0.135 mol) and disopropylethylamine (23.5 mL, 0.135 mol) in dry acetonitrile (285 mL) was added over 10 min and cooling applied to maintain reaction temperature at ca. 16° C. during the addition. The reaction was concentrated in vacuo and the resultant orange oil partitioned between DCM (700 mL) and water (700 mL). The aqueous was extracted with DCM (500 mL) and the combined organic extracts were cautiously washed with brine (300 mL). After drying (Na$_2$SO$_4$) the mixture was concentrated in vacuo to give a dark orange oil. Purification using flash chromatography on (2 kg silica column), eluting with 1:1–0:1 cyclohexane:DCM afforded the title compound as a yellow oil (48.8 g).

LC/MS: m/z 460.2 [M+H]$^+$, R$_t$ 4.42 min

Intermediate 75: 2-Chloro-6-(4-chlorophenyl)pyrazine

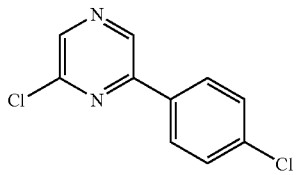

To a mixture of 2,6-dichloropyrazine (3 g, 20 mmol), sodium carbonate (5.5 g, 52 mmol) and 4-chlorophenylboronic acid (3.79 g, 3.36 mmol) in dimethoxyethane (140 mL) and water (70 mL) under nitrogen was added tetrakis (triphenylphosphine) palladium (0) (0.46 g). The resulting mixture was heated at reflux for 18 h under nitrogen. The reaction mixture was allowed to cool to room temperature and diluted with water (150 mL) and extracted with dichloromethane (2×200 mL). The organic solution was passed through a hydrophobic frit and the solvents removed in vacuo. Purification by Biotage™ (Si, 90 g) 9:1 cyclohexane:EtOAc afforded the title compound as a white solid (2.33 g).

LC/MS: m/z 225.0 [M+H]$^+$, R$_t$ 3.45 min

Intermediate 76: 2-Bromo-6-(4-chlorophenyl)pyrazine

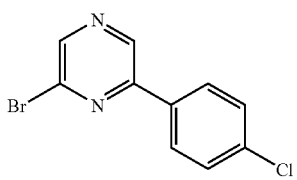

To a flask containing 2-chloro-6-(4-chlorophenyl)pyrazine (2.35 g, 10.4 mmol), was added phosphorus tribromide (17 mL) and the mixture heated at reflux for 6 h under nitrogen. The reaction mixture was cooled to room temperature prior to pouring carefully into iced water (600 mL) the resulting mixture was adjusted to pH 6–7 using aqueous ammonia and extracted with diethyl ether (2×250 mL). The organic solution was dried (MgSO$_4$) and the solvent removed in vacuo. The reaction had not gone to completion so the residue was treated with added phosphorus tribromide (17 mL) and heated at reflux for a further 5 h under nitrogen. Work up as before afforded the title compound as a pale yellow solid (0.97 g).

LC/MS: m/z 270 [M+H]$^+$, R$_t$ 3.53 min

Intermediate 77: Ethyl [4-({butyl[6-(4-chlorophenyl)pyrazin-2-yl]amino}methyl)-2-methylphenoxy]acetate

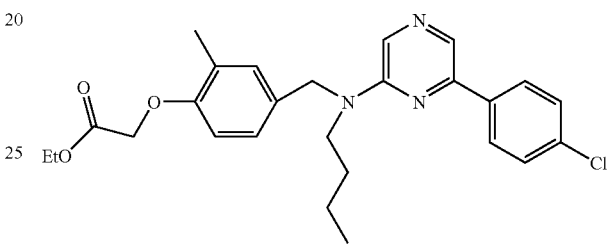

A mixture of 2-bromo-6-(4-chlorophenyl)pyrazine (0.27 g, 1 mmol), N,N-diisopropylethylamine (0.18 mL, 1 mmol) and ethyl {4-[(butylamino)methyl]-2-methylphenoxy}-acetate (0.42 g, 1.5 mmol) was heated at 100° C. in a sealed reactivial for 18 h. The reaction mixture was then allowed to come to room temperature and the residue dissolved in CH$_2$Cl$_2$ (50 mL), the organic extract was washed water (15 mL) and passed through a hydrophobic frit before concentrating in vacuo. Purification by Biotage™ chromatography (Si, 40 g) eluting 1:9–1:1.5 EtOAc:cyclohexane afforded the title compound as a pale yellow oil 78 mg.

LC(MS: m/z 468 [M+H]$^+$, R$_t$ 4.2 min.

Intermediate 78: Ethyl [4-({[6-(4-chlorophenyl)pyrazin-2-yl][2-(methyloxy)ethyl]amino}methyl)-2-methylphenoxy]acetate

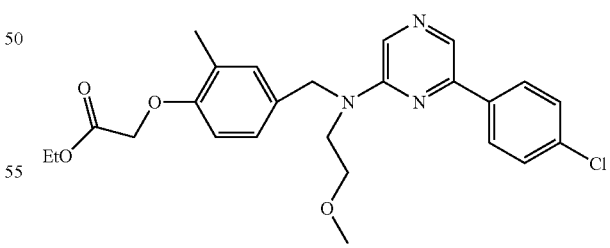

Using ethyl (4-{[(2-methoxyethyl)amino]methyl}-2-methylphenoxy)acetate (0.42 g, 1.5 mmol) and the synthetic procedure described for intermediate 77. Purification by Biotage™ chromatography (Si, 40 g) eluting 1:4–1:1 EtOAc:cyclohexane afforded the title compound as a pale yellow oil (81 mg).

LC/MS: m/z 470 [M+H]$^+$, R$_t$ 3.8 min.

Intermediate 79: Ethyl {2-methyl-4-[(propyl{6-[4-(trifluoromethyl)phenyl]pyrazin-2-yl}amino)methyl]phenoxy}acetate

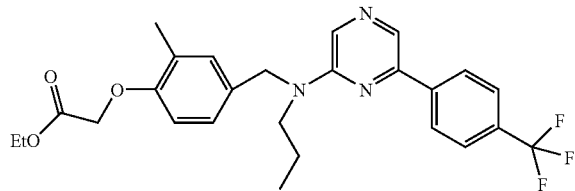

Using 2-chloro-6-(4-(trifluoromethyl)phenyl]pyrazine (0.303 g, 1 mmol) and ethyl {2-methyl-4-[(propylamino)methyl]phenoxy}acetate (0.4 g, 1.5 mmol) and the synthetic procedure described for Intermediate 77. Purification by Biotage™ chromatography (Si, 40 g) eluting 9:1–7:3 cyclohexane:EtOAc afforded the title compound as a pale yellow oil (56 mg).

LC/MS: m/z 488 [M+H]$^+$, R$_t$4.1 min

Intermediate 80: Ethyl (2-methyl-4-{[{5-methyl-6-[4-(trifluoromethyl)phenyl]pyrimidin-4-yl}(propyl)amino]methyl}phenoxy)acetate

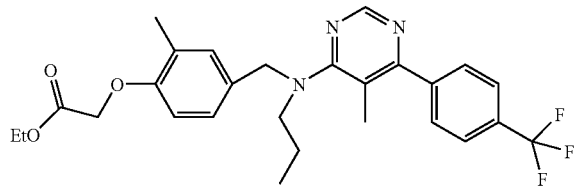

A mixture of ethyl {2-methyl-4-[(propylamino)methyl]phenoxy}acetate (0.279 g, 1.05 mmol), N,N-diisopropylethylamine (0.24 mL, 1.4 mmol) and 4-chloro-5-methyl-6-[4-(trifluoromethyl)phenyl]pyrimidine (0.191 g, 0.7 mmol) were heated at 100° C. in a sealed reactivial for 18 h. After this time the reactivial was allowed to cool to room temperature and the residue dissolved in CH$_2$Cl$_2$ (50 mL) and washed with water (20 mL). The organic extract was separated by hydrophobic frit and evaporated. Purification by Biotage™ chromatography (Si, 40 g) eluting 9:1 cyclohexane:EtOAc afforded the title compound as a pale yellow oil (159 mg).

LC/MS: m/z 502.2 [M+H]$^+$, R$_t$3.8 min.

Intermediate 81: Ethyl (4-{[[6-(4-chlorophenyl)-5-methylpyrimidin-4-yl](propyl)amino]methyl}-2-methylphenoxy)acetate

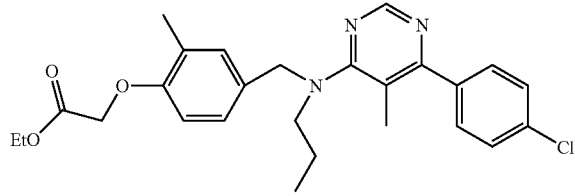

Using 4-chloro-6-(4-chlorophenyl)-5-methylpyrimidine (167 mg, 0.7 mmol) and the synthetic procedure described for Intermediate 80. Purification by Biotage™ chromatography (Si, 40 g) eluting 9:1 cyclohexane:EtOAc afforded the title compound as a pale yellow oil (116 mg).

LC/MS: m/z 468.1 [M+H]$^+$, R$_t$3.6 min

Intermediate 82: Ethyl (2-methyl-4-{[[5-methyl-6-(4-methylphenyl)pyrimidin-4-yl](propyl)amino]methyl}phenoxy)acetate

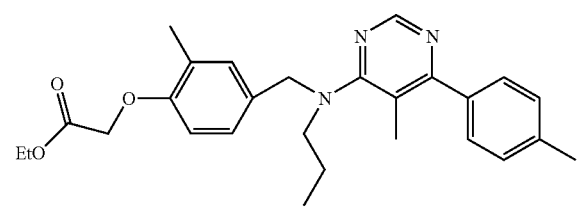

Using 4-chloro-5-methyl-6-(4-methylphenyl)pyrimidine (153 mg, 0.7 mmol) and the synthetic procedure described for Intermediate 80. Purification by Biotage™ chromatography (Si, 40 g) eluting 9:1 cyclohexane:EtOAc afforded the title compound as a pale yellow oil (80 mg).

LC/MS: m/z 448.2 [M+H]$^+$, R$_t$3.2 min

Intermediate 83: Ethyl (2-methyl-4-{[{5-methyl-6-[4-(methyloxy)phenyl]pyrimidin-4-yl}(propyl)amino]methyl}phenoxy)acetate

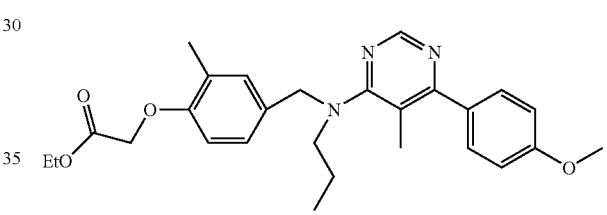

Using 4-chloro-6-(4-methoxyphenyl)-5-methylpyrimidine (164 mg, 0.7 mmol) and the synthetic procedure described for Intermediate 80. Purification by Biotage™ chromatography (Si, 40 g) eluting 4:1 cyclohexane:EtOAc afforded the title compound as a pale yellow oil (60 mg).

LC/MS: m/z 464.2 [M+H]$^+$, R$_t$3.1 min

Intermediate 84: 2-Ethyl-4-(hydroxymethyl)phenol

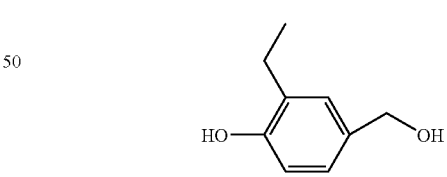

To a solution of 3-ethyl-4-hydroxybenzaldehyde (4.7 g, 26 mmol) in anhydrous THF (150 mL) at 0° C. under N$_2$ was added dropwise 1 M LiAlH$_4$ in Et$_2$O (52 mL, 52.2 mmol). The resulting mixture was stirred at 0° C. for 2 h and then quenched by cautious addition of water and stirred for 15 minutes. The reaction mixture was then absorbed onto silica and loaded onto a silica pad which was washed with EtOAc. The EtOAc washings were collected and concentrated in vacuo to afford the title compound as a colourless oil (3.67 g).

LC/MS: m/z 151.1 [M–H]$^-$, R$_t$2.1 min.

Intermediate 85: Ethyl [2-ethyl-4-(hydroxymethyl)phenoxy]acetate

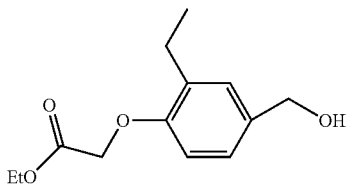

To a solution of 2-ethyl-4-(hydroxymethyl)phenol (3.67 g, 24.1 mmol) in anhydrous acetonitrile (125 mL) was added caesium carbonate (8.65 g, 26.6 mmol), the reaction mixture was then flushed with nitrogen and cooled to 0° C. before addition of ethyl bromoacetate (2.68 mL, 24.1 mmol). The reaction mixture was allowed to gradually attain room temperature and stirred for 18 h. Further ethylbromoacetate (0.26 mL, 2.4 mmol) was added and stirring continued for 4 h. The reaction mixture was diluted with water (100 mL) and then extracted EtOAc (2×100 mL). The combined organic extracts were dried (MgSO$_4$) filtered and evaporated. Purification by Biotage™ chromatography (Silica, 90 g) eluting 4:1 cyclohexane:EtOAc, then EtOAc afforded the title compound as a pale yellow gum (3.54 g).

$^1$H NMR (400 MHz; CDCl$_3$) δ: 1.23 (3H, t, J 7.5 Hz), 1.29 (3H, t, J 7.5 Hz), 2.72 (2H, q, J 7.5 Hz), 4.26 (2H, q, J 7.5 Hz), 4.58–4.68 (4H, m), 6.69 (1H, d, J 8.5 Hz), 7.13 (1H, dd, J 8.5, 2 Hz), 7.19 (1H, d, J 2 Hz).

Intermediate 86: Ethyl (2-ethyl-4-formylphenoxy)acetate

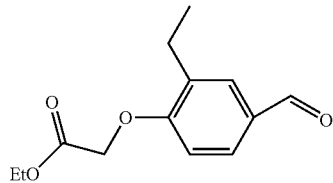

To a solution of ethyl [2-ethyl-4-(hydroxymethyl)phenoxy]acetate (2.74 g, 11.5 mmol) in chloroform (250 mL) was added manganese dioxide (10 g, 11.5 mmol). The resulting mixture was stirred for 18 h at room temperature. The mixture was filtered through a celite pad and then concentrated in vacuo to afford the title compound as a pale yellow oil (2.7 g).

LC/MS: m/z 237.2 [M+H]$^+$, R$_t$3.1 min.

Intermediate 87: Ethyl [2-ethyl-4-({[4'-(trifluoromethyl)-1,1'-biphenyl-3-yl]amino}methyl)phenoxy]acetate

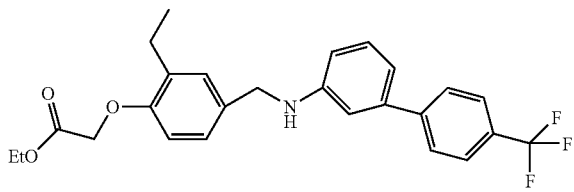

To a solution of ethyl (2-ethyl-4-formylphenoxy)acetate (0.3 g, 1.27 mmol) in anhydrous CH$_2$Cl$_2$ (12 mL) was added 4'-(trifluoromethyl)-1,1'-biphen-3-ylamine (0.3 g, 1.27 mmol). The resulting solution was stirred at room temperature under N$_2$ for 15 mins and then sodium triacetoxyborohydride (0.376 g, 1.77 mmol) and glacial acetic acid (0.0725 mL, 1.27 mmol) were added. After 20 h stirring at room temperature under nitrogen, sat NaHCO$_3$ aq. (40 mL) was added dropwise and the mixture stirred for 20 mins. The mixture was then extracted CH$_2$Cl$_2$ (2×50 mL) and the organic extracts separated by hydrophobic frit and concentrated in vacuo. Purification by Biotage™ chromatography (Silica, 40 g) eluting 9:1 cyclohexane:EtOAc, afforded the title compound as a pale yellow crysatline solid (0.47 g).

LC/MS: m/z 458.2 [M+H]$^+$, R$_t$4.1 min.

Intermediate 88: Ethyl {4-[(butylamino)methyl]-2-ethylphenoxy}acetate

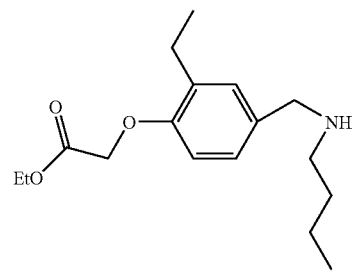

To a solution of ethyl (2-ethyl-4-formylphenoxy)acetate (0.52 g, 2.2 mmol) in anhydrous ethanol (10 mL) was added butylamine (0.26 mL, 2.6 mmol). The resulting solution was stirred at room temperature under N$_2$ for 18 h over 4A molecular sieves. The reaction was quenched by cautious addition of sat. NaHCO$_3$ aq. (30 mL) and the mixture stirred for 30 mins. The mixture was then extracted EtOAc (2×100 mL). The combined organic extracts were dried (MgSO$_4$), filtered and concentrated in vacuo. Purification by SPE (SCX, 20 g) conditioning the cartridge with ethanol and then loading the compound and washing with CH$_2$Cl$_2$, then ethanol before eluting the title compound using 10% NH$_3$ in ethanol, evaporation of the 10% NH$_3$ in ethanol extract afforded the title compound as a pale yellow oil (0.364 g).

LC/MS: m/z 294.3 [M+H]$^+$, R$_t$2.43 min.

Intermediate 89: Ethyl [2-ethyl-4-{[2-(methoxyethyl)amino]methyl}phenoxy]acetate

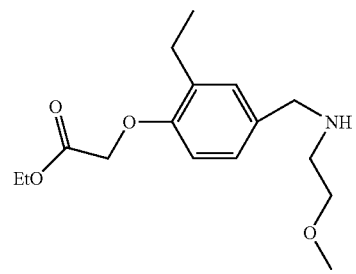

Using 2-methoxyethylamine (0.23 mL, 0.26 mmol) and the synthetic procedure described for the synthesis of Intermediate 88. Purification by SPE (SCX, 20 g) conditioning the cartridge with ethanol and then loading the compound and washing with CH$_2$Cl$_2$, then ethanol before eluting the title compound using 10% NH$_3$ in ethanol, evaporation of the 10% NH$_3$ in ethanol extract afforded the title compound as a pale yellow oil (0.341 g).

LC/MS: m/z 296.2 [M+H]$^+$, R$_t$2.2 min.

Intermediate 90: Ethyl {4-[(butyl{6-[4-(trifluoromethyl)phenyl]pyrazin-2-yl}amino)methyl]-2-ethylphenoxy}acetate

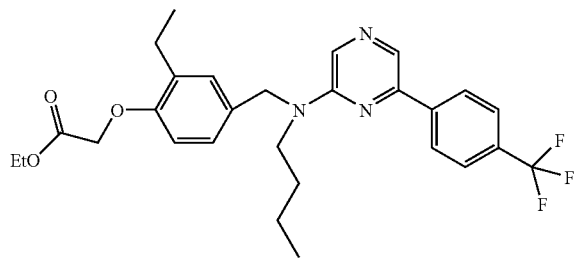

A mixture of 2-chloro-6-[4-(trifluoromethyl)phenyl]pyrazine (0.172 g, 0.56 mmol), ethyl {4-[(butylamino)methyl]-2-ethylphenoxy}acetate (0.25 g, 0.85 mmol) and N,N-diisopropylethylamine (0.099 mL, 0.56 mmol) were heated together in a reactivial at 100° C. for 18 h. The vial was then allowed to cool to room temperature and the residue dissolved in CH$_2$Cl$_2$ (50 mL) and the organic solution washed with water (15 mL) and brine (10 mL). The solution was then passed through a hydrophobic frit and evaporated. Purification by Biotage™ chromatography (Silica, 40 g) eluting 9:1cyclohexane:EtOAc, afforded the title compound as a pale yellow oil (50 mg).

LC/MS: m/z 516.3 [M+H]$^+$, R$_t$4.3 min.

Intermediate 91: Ethyl {2-ethyl-4-[(2-methyloxyethyl){6-[4-(trifluoromethyl)phenyl]pyrazin-2-yl}amino)methyl]phenoxy}acetate

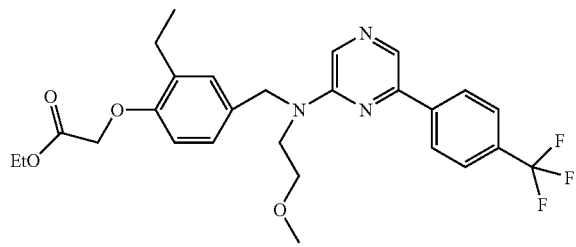

A mixture of 2-chloro-6-[4-(trifluoromethyl)phenyl]pyrazine (0.109 g, 0.36 mmol), ethyl [2-ethyl-4-{[2-(methoxyethyl)amino]methyl}phenoxy]acetate (0.159 g, 0.54 mmol) and N,N-diisopropylethylamine (0.063 mL, 0.36 mmol) were heated together in a reactivial at 100° C. for 18 h. The vial was then allowed to cool to room temperature, the residue dissolved in CH$_2$Cl$_2$ (50 mL) and the organic solution washed with water (15 mL) and brine (10 mL). The solution was passed through a hydrophobic frit and evaporated. Purification by Biotage™ chromatography (Silica, 40 g) eluting 9:1–4:1 cyclohexane:EtOAc, afforded the title compound as a pale yellow oil (48 mg).

LC/MS: m/z 518.3 [M+H]$^+$, R$_t$3.9 min.

Intermediate 92: Ethyl [4-({butyl[5-methyl-6-(4-methylphenyl)pyrimidin-4-yl]amino}methyl)-2-ethylphenoxy]acetate

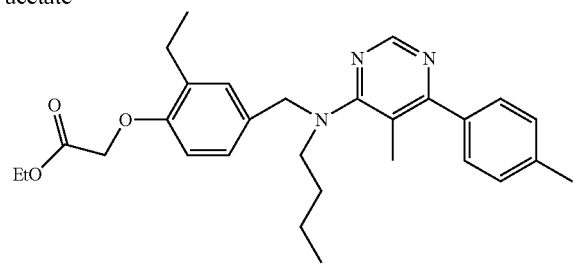

A mixture of ethyl {4-[(butylamino)methyl]-2-ethylphenoxy}acetate (0.23 g, 0.78 mmol), N,N-diisopropylethylamine (0.18 mL, 1.05 mmol) and 4-chloro-5-methyl-6-(4-methylphenyl)pyrimidine (0.114 g, 0.52 mmol) were heated at 100° C. in a sealed reactivial for 18 h. After this time the reactivial was allowed to cool to room temperature and the residue dissolved in CH$_2$Cl$_2$ (50 mL) and washed with water (10 mL) and brine (10 mL). The organic extract was separated by hydrophobic frit and evaporated. Purification by Biotage™ chromatography (Silica, 40 g) eluting 9:1 cyclohexane:EtOAc afforded the title compound as a pale yellow oil (46 mg).

LC/MS: m/z 476.3 [M+H]$^+$, R$_t$3.6 min.

Intermediate 93: Ethyl [4-({butyl[2-methyl-4'-(trifluoromethyl)-1,1'-biphenyl-3-yl]amino}sulfonyl)-2-methylphenoxy]acetate

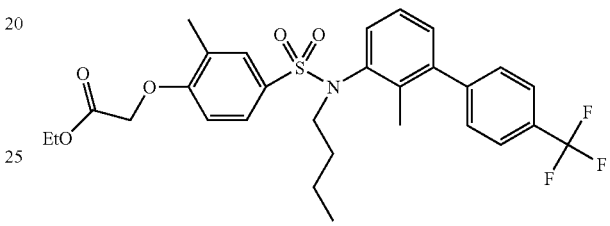

To a solution of N-butyl-N-[2-methyl-4'-(trifluoromethyl)-1,1'-biphenyl-3-yl]amine (58 mg, 0.19 mmol) in anhydrous CH$_2$Cl$_2$ (5 mL) was added ethyl [4-(chlorosulfonyl)-2-methylphenoxy]acetate (83 mg, 0.28 mmol) and triethylamine (0.052 mL, 0.38 mmol). The resulting solution was stirred 20 h at room temperature under nitrogen. The reaction was diluted with CH$_2$Cl$_2$ (50 mL), and the organic solution washed with aq. sat. NaHCO$_3$ (10 mL) and brine (10 mL). The organic extract was separated by hydrophobic frit and evaporated. Purification by mass directed autoprep afforded the title compound as a colourless oil (15 mg).

LC/MS: m/z 564.2 [M+H]$^+$, R$_t$4.2 min.

Intermediate 94: Ethyl [2-ethyl-4-({(propylsulfonyl)[4'-(trifluoromethyl)-1,1'-biphenyl-3-yl]amino}methyl)pheoxy]acetate

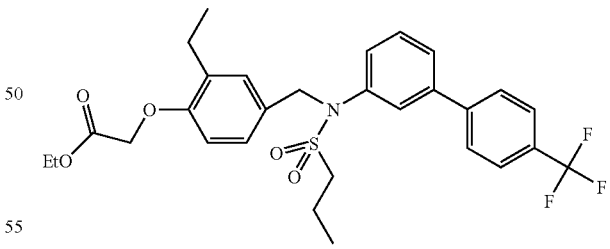

To a solution of ethyl [2-ethyl-4-({[4'-(trifluoromethyl)-1,1'-biphenyl-3-yl]amino}methyl)phenoxy]acetate (0.1 g 0.22 mmol) in anhydrous pyridine (0.3 mL) was added 1-propane sulfonylchloride (0.037 mL, 0.3 mmol). The reaction mixture was then heated at 80° C. in a sealed reactivial for 18 h. Once the reaction mixture had cooled to room temperature the vial was opened and the residue dissolved in CH$_2$Cl$_2$ (30 mL) and washed with water (20 mL) and brine (20 mL). Th organic extract was separated by hydrophobic firt and evaporated. Purification by Biotage™ chromatography (Silica, 12 g) eluting 9:1–17:3 cyclohexane:EtOAc, afforded the title compound as a yellow solid (65 mg).

LC/MS: m/z 581.3 [M+NH₄]+, R,4.0 min.

Intermediate 95: Ethyl [4-({butyl[6-(4-chlorophenyl)-5-methylpyrimidin-4-yl]amino}methyl)-2-ethylphenoxy]acetate

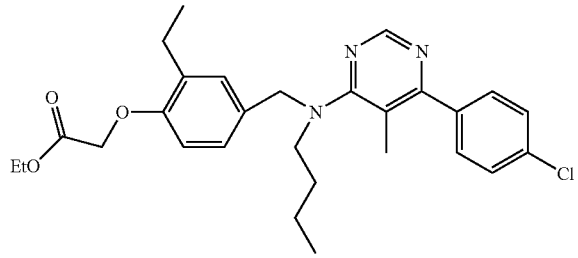

Using 4-chloro-6-(4-chlorophenyl)-5-methylpyrimidine (0.125 g, 0.52 mmol) and the synthetic procedure described for Example 92. Purification by Biotage™ chromatography (Silica, 40 g) eluting 9:1 cyclohexane:EtOAc, followed by further purification using OPTIX (Silica, 4 g) 19:1 eluting cyclohexane:EtOAc afforded the title compound as a pale yellow oil (64 mg).

LC/MS: m/z 496.2 [M+H]+, R,4.0 min.

Intermediate 96: Ethyl {4-[(butyl{5-methyl-6-[4-(trifluoromethyl)phenyl]pyrimidin-4-yl}amino)methyl]-2-ethylphenoxy}acetate

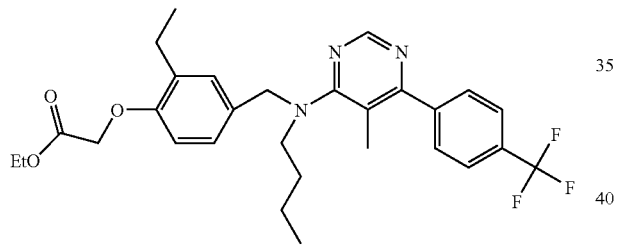

Using 4-chloro-5-methyl-6-[4-(trifluoromethyl)phenyl]pyrimidine (0.143 g, 0.52 mmol) and the synthetic procedure described for Example 92. Purification by Biotage™ chromatography (Silica, 40 g) eluting 9:1 cyclohexane:EtOAc, followed by further purification using OPTIX (Silica, 4 g) 19:1 eluting cyclohexane:EtOAc afforded the title compound as a pale yellow oil (64 mg).

LC/MS: m/z 430.2 [M+H]+, R,4.2 min.

Intermediate 97: Ethyl {2-ethyl-4-[([2-(methyloxy)ethyl]{4-[4-(trifluoromethyl)phenyl]pyrimidin-2-yl}amino)methyl]phenoxy}acetate

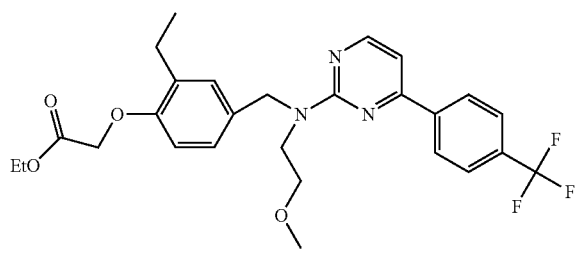

A mixture of pyrimidine 2-(methylsulfonyl)-4-[4-(trifluoromethyl)phenyl]pyrimidine (0.109 g, 0.36 mmol), ethyl [2-ethyl-4-{[2-(methoxyethyl)amino]methyl}phenoxy]acetate (0.159 g, 0.54 mmol) and N,N-diisopropylethylamine (0.063 mL, 0.36 mmol) were heated together in a reactivial at 100° C. for 18 h. The vial was then allowed to cool to room temperature and the residue dissolved in CH₂Cl₂ (50 mL). The organic solution washed with water (15 mL) and brine (10 mL). The solution was then passed through a hydrophobic frit and evaporated. Purification by SPE (Silica, 10 g) eluting 9:1–4:1 cyclohexane:EtOAc, afforded the title compound as a pale yellow oil (52 mg).

LC/MS: m/z 518.3 [M+H]+, R,4.1 min.

Intermediate 98: N-2-Propen-1-yl-6-[4-(trifluoromethyl)phenyl]-2-pyridinamine

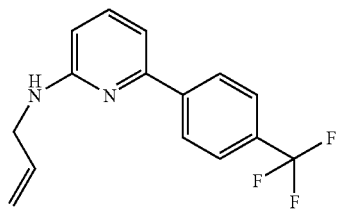

A mixture of of allylamine (0.447 mL, 5.96 mmol) and 2-bromo-6-[4-(trifluoromethyl)phenyl]pyridine (0.1 g, 0.298 mmol) in ethanol (5 mL) were heated at 100° C. in a 25 mL pressure vessel. After heating overnight the reaction was cooled and copper sulfate was added and heating continued at 100° C. overnight. After this time the reaction was allowed to coole to room temperature and concentrated in vacuo. Purification by SPE (Silica, 10 g) eluting 3:1 cyclohexane:chloroform afforded the title compound as a dark yellow solid (0.062 g).

LC/MS: m/z 279.1 [M+H]+, R, 3.7 min.

EXAMPLE 1

2-Methyl-2-{2-methyl-4-[([4-(trifluoromethyl)benzyl]{6-[4-(trifluoromethyl)phenyl]pyridin-2-yl}amino)methyl]phenoxy}propanoic acid

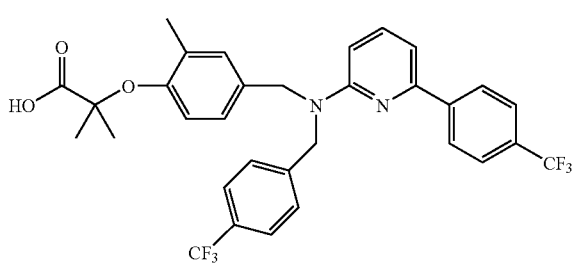

To a solution of ethyl 2-methyl-2-{2-methyl-4-[([4-(trifluoromethyl)benzyl]{6-[4-(trifluoromethyl)phenyl]pyridin-2-yl}amino)methyl]phenoxy}propanoate (0.07 g, 0.11 mmol) in tetrahydrofuran (2 mL) and methanol (2 mL) was added 2M aq. NaOH (1 mL). The resulting solution was stirred at room temperature for 20 h then concentrated in vacuo. The residue was acidified with 2M HCl aq. and extracted with CH₂Cl₂ (2×30 mL). The combined organic extracts were dried (Na₂SO₄), filtered and evaporated to afford the title compound as a colourless oil (60 mg).

¹H NMR (400 MHz; CDCl₃) δ: 1.60 (6H, s), 2.20 (3H, s), 4.77 (2H, s), 4.93 (2H, s), 6.47 (1H, d, J 8.5 Hz), 6.77 (1H, d, J 8 Hz), 7.00 (1H, dd, J 8.5, 2 Hz), 7.07 (1H, d, J 2 Hz), 7.14 (1H, d, J 7.5 Hz), 7.37 (2H, d, J 8.5 Hz), 7.47–7.58 (3H, m), 7.64 (2H, d, J 8.5 Hz), 8.05 (2H, d J 8.5 Hz), CO$_2$H not observed.

LC/MS: m/z 603.2 [M+H]$^+$, R$_t$ 4.6 min.

EXAMPLE 2

2-{4-[(Butyl{6-[4-(trifluoromethyl)phenyl]pyridin-2-yl}amino) methyl]-2-methylphenoxy}-2-methyl-propanoic acid

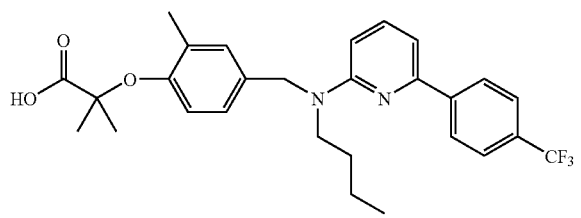

To a solution of ethyl 2-{4-[(butyl{6-[4-(trifluoromethyl)phenyl]pyridin-2-yl}amino)methyl]-2-methylphenoxy}-2-methylpropanoate (45 mg, 0.085 mmol) in methanol (1.5 mL) and tetrahydrofuran (1.5 mL) was added 2M NaOH aq. (1 mL). The resulting mixture was heated to 70° C. for 1 h and then stirred at room temperature for 18 h, before heating to 70° C. for a further 4 h. The reaction mixture was allowed to attain room temperature and the solvents removed in vacuo. The residue was acidified with 2M HCl and extracted with EtOAc (2×10 mL). The organic solution was dried (MgSO$_4$) and the solvents removed in vacuo. Purification by aminopropyl SPE (5 g) conditioning the cartridge, loading the compound and washing with methanol before eluting using 10% NH$_3$ in methanol. Evaporation of the methanolic ammonia yielded a white solid, which was treated with 1 M HCl (5 mL) and then extracted into CH$_2$Cl$_2$ (20 mL). The organic extract was dried (Na$_2$SO$_4$) and the solvent removed in vacuo to afford the title compound as a colourless oil (19 mg).

$^1$H NMR (400 MHz; CDCl$_3$) δ: 0.95 (3H, t, J 7 Hz), 1.37 (2H, m), 1.56 (6H, s), 1.64 (2H, m), 2.19 (3H, s), 3.55 (2H, t, J 7.5 Hz), 4.74 (2H, s), 6.44 (1H, d, J 8.5 Hz), 6.75 (1H, d, J 8.5 Hz), 6.98 (1H, dd, J 8.5, 1.5 Hz), 7.04 (1H, d, J 7.5 Hz), 7.08 (1H, d, J 1.5 Hz), 7.48 (1H, dd, J 8.5, 7.5 Hz), 7.64 (2H, d, J 8 Hz), 8.08 (2H, d J 8 Hz), CO$_2$H not observed.

LC/MS: m/z 501.2 [M+H]$^+$, R$_t$ 4.7 min.

EXAMPLE 3

{4-[(Butyl{6-[4-(trifluoromethyl)phenyl]pyridin-2-yl}amino)methyl]-2-methylphenoxy}acetic acid

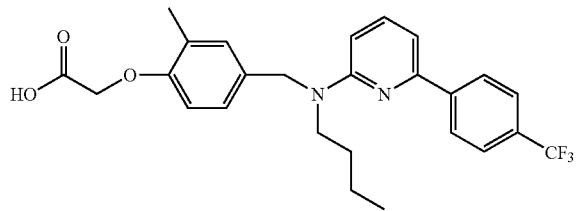

To a solution of methyl {4-[(butyl{6-[4-(trifluoromethyl)phenyl]pyridin-2-yl}amino)methyl]-2-methylphenoxy}acetate (40 mg, 0.082 mmol) in methanol (2 mL) and tetrahydrofuran (2 mL), was added 2M NaOH aq. (2 mL). After stirring for 1 h at room temperature the solvent was removed in vacuo and the residue acidified with 2M HCl, before extraction into ethyl acetate (2×15 mL). The organic solution was dried (MgSO$_4$) and the solvents removed in vacuo to afford the title compound as a white solid (35 mg).

$^1$H NMR (400 MHz; CDCl$_3$) δ: 0.96 (3H, t, J 7.5 Hz), 1.39 (2H, m), 1.66 (2H, m), 2.26 (3H, s), 3.57 (2H, t, J 8 Hz), 4.66 (2H, s), 4.76 (2H, s), 6.47 (1H, d, J 8.5 Hz), 6.67 (1H, d, J 8.5 Hz), 7.02–7.14 (3H, m), 7.50 (1H, m), 7.66 (2H, d, J 8 Hz), 8.08 (2H, d, J 8 Hz), CO$_2$H not observed.

LC/MS: m/z 473.2 [M+H]$^+$, R$_t$ 5.0 min.

EXAMPLE 4

[4-({Butyl[4'-(trifluoromethyl)-1,1'-biphenyl-3-yl]amino}methyl)-2-methylphenoxy]acetic acid

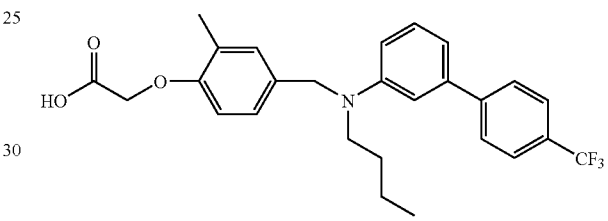

To a solution of ethyl [4-({butyl[4'-(trifluoromethyl)-1,1'-biphenyl-3-yl]amino}methyl)-2-methylphenoxy]acetate (105 mg, 0.21 mmol) in methanol (4 mL) and tetrahydrofuran (4 mL), was added 2M NaOH (2 mL) aq. After stirring for 1 h at room temperature the solvent was removed in vacuo and the residue acidified with 2M HCl, before extraction into ethyl acetate (2×20 mL). The organic solution was dried (MgSO$_4$) and the solvents removed in vacuo to afford the title compound as a pale yellow foam (90 mg).

$^1$H NMR (400 MHz; MeOH-d$^4$) δ: 0.97 (3H, t, J 7.5 Hz), 1.42 (2H, m), 1.60 (2H, m), 2.20 (3H, s), 3.69 (2H, m), 4.66–4.70 (4H, m), 6.77 (1H, d, J 8 Hz), 7.00–7.07 (2H, m), 7.10–7.57 (4H, m), 7.71 (2H, d, J 8 Hz), 7.76 (2H, d J 8 Hz), CO$_2$H not observed.

LC/MS: m/z 472.1 [M+H]$^+$, R$_t$ 4.6 min

EXAMPLE 5

[4-({(2-Methoxyethyl)[4'-(trifluoromethyl)-1,1'-biphenyl-3-yl]amino}methyl)-2-methylphenoxy]acetic acid

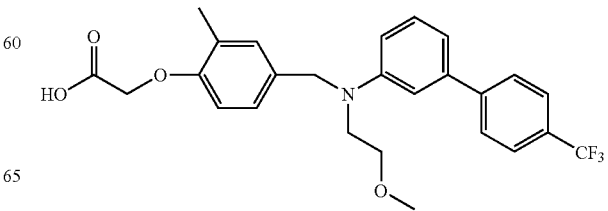

To a solution of ethyl [4-({(2-methoxyethyl)[4'-(trifluoromethyl)-1,1'-biphenyl-3-yl]amino}methyl)-2-methylphenoxy]acetate (90 mg, 0.18 mmol) in methanol (2 mL) and tetrahydrofuran (2 mL), was added 2M NaOH aq. (1 mL). After stirring for 1 h at room temperature the solvent was removed in vacuo and the residue diluted with water (10 mL) acidified with 2M HCl, before extraction into ethyl acetate (2×20 mL). The organic solution was dried (MgSO$_4$) and the solvents removed in vacuo to afford the title compound as a white solid (28 mg).

$^1$H NMR (400 MHz; CDCl$_3$) δ: 2.22 (3H, s), 3.33 (3H, s), 3.68 (4H, s), 4.58 (2H, s), 4.65 (2H, s), 6.63 (1H, d J 9 Hz), 6.88–7.15 (5H, m), 7.31 (1H, t, J 8 Hz), 7.58 (2H, d, J 8 Hz), 7.65 (2H, d, J 8 Hz), CO$_2$H not observed.

LC/MS: m/z 471.9 [M−H]$^-$, R$_t$ 4.1 min.

EXAMPLE 6

[2-Methyl-4-({pentyl[4'-(trifluoromethyl)-1,1'-biphenyl-3-yl]amino}methyl)phenoxy]acetic acid

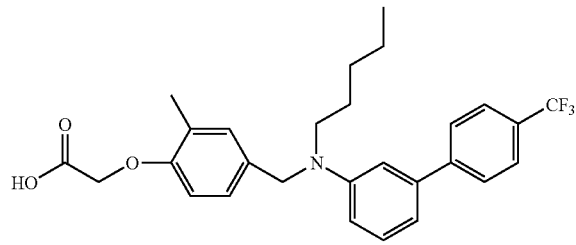

To a solution of ethyl [2-methyl-4-({pentyl[4'-(trifluoromethyl)-1,1'-biphenyl-3-yl]amino}methyl)phenoxy]acetate (54 mg, 0.11 mmol) in MeOH (2 mL) and THF (2 mL) at room temperature was added 2M NaOH (1 mL, 2 mmol). The resultant mixture was stirred for 1 h and then the solvents were removed in vacuo. The residue was partitioned between CH$_2$Cl$_2$ (2×10 mL) and 2M HCl (10 mL). The organic solution was passed through a hydrophobic frit and the solvent was removed, affording the title compound as a white solid (59 mg).

$^1$H NMR (400 MHz; MeOH-d$^4$) δ: 0.91 (3H, t, J 7 Hz), 1.35 (4H, m), 1.61 (2H, br.s), 2.19 (3H, s), 3.73 (2H, m), 4.70 (4H, s), 6.76 (1H, d, J 8.5 Hz), 7.04 (2H, m), 7.25–7.43 (2H, m), 7.51–7.63 (2H, m), 7.72 (2H, d, J 8 Hz), 7.78 (2H, d, J 8 Hz), CO$_2$H not observed.

LC/MS: m/z 486.3 [M+H]$^+$ R$_t$ 4.9 min.

EXAMPLE 7

[4-({(2-Cyclopropylethyl)[4'-(trifluoromethyl)-1,1'-biphenyl-3-yl]amino}methyl)-2-methylphenoxy]acetic acid

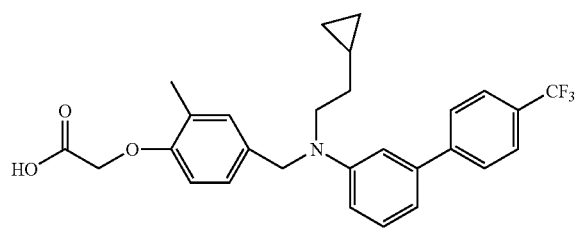

To a solution of ethyl [4-({(2-cyclopropylethyl)[4'-(trifluoromethyl)-1,1'-biphenyl-3-yl]amino}methyl)-2-methylphenoxy]acetate (141 mg, 0.28 mmol) in MeOH (2 mL) and THF (2 mL) at room temperature was added 2M NaOH (1 mL, 2 mmol). The resultant mixture was stirred for 1.5 h, then the solvents were removed in vacuo. The residue was partitioned between CH$_2$Cl$_2$ (2×20 mL) and 2M HCl (20 mL). The organic solution was passed through a hydrophobic frit and the solvent was removed, affording the title compound as a white solid (115 mg).

$^1$H NMR (400 MHz; MeOH-d$^4$) δ: 0.07 (2H, m), 0.50 (2H, dm, J 8 Hz), 0.70 (1H, m), 1.46 (2H, m), 2.15 (3H, s), 3.89 (2H, t, J 7.5 Hz), 4.68 (2H, s), 4.74 (2H, br s) 6.75 (1H, d, J 8.5 Hz), 6.97 (1H, d, J 1.5 Hz), 7.04 (1H, dd, J 8.5 Hz, 2.5 Hz), 7.42 (1H, br s), 7.50 (1H, br s), 7.63 (1H, t, J 8 Hz), 7.68–7.81 (5H, m), CO$_2$H not observed.

LC/MS: m/z 484.3 [M+H]$^+$ R$_t$ 4.6 min.

EXAMPLE 8

[2-Methyl-4-({propyl[4'-(trifluoromethyl)-1,1'-biphenyl-3-yl]amino}methyl)phenoxy]acetic acid

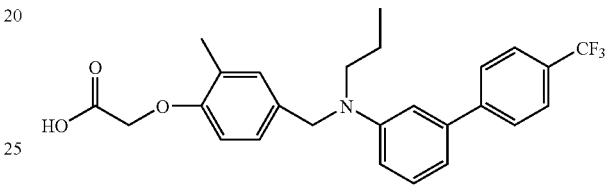

To a solution of ethyl [2-methyl-4-({propyl[4'-(trifluoromethyl)-1,1'-biphenyl-3-yl]amino}methyl)phenoxy]acetate (88 mg, 0.18 mmol) in MeOH (2 ml) and THF (2 mL) at room temperature was added 2M NaOH (1 mL, 2 mmol). The resultant solution was stirred for 1 h, then the solvents were removed in vacuo. The residue was diluted with HCl (10 mL) and extracted with CH$_2$Cl$_2$ (2×10 mL), followed by EtOAc (2×10 mL). The organic solutions were dried (MgSO$_4$) and the solvents were removed in vacuo affording the title compound as a white crystalline solid (64.1 mg).

$^1$H NMR (400 MHz; MeOH-d$^4$) δ: 0.95 (3H, t, J 7.5 Hz), 1.69 (2H, m), 2.21 (3H, s), 3.42 (2H, t, J 7.5 Hz), 4.50 (2H, s), 4.56 (2H, s), 6.68–6.75 (2H, m), 6.82–6.88 (2H, m), 6.98 (1H, dd, J 8.5 Hz, 2 Hz), 7.03 (1H, s), 7.21 (1H, t, J 8.5 Hz), 7.64 (4H, m), CO$_2$H not observed.

LC/MS: m/z 455.9 [M−H]$^-$ R$_t$ 4.4 min.

EXAMPLE 9

[2-Methyl-4-({[2-(methylthio)ethyl][4'-(trifluoromethyl)-1,1'-biphenyl-3-]amino}methyl)phenoxy]acetic acid

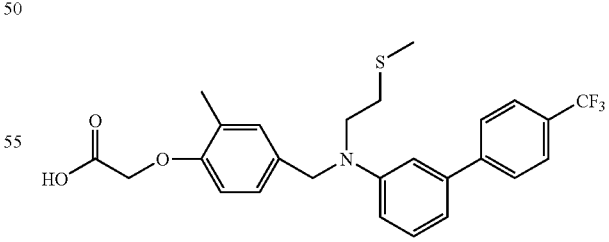

To a solution of methyl [2-methyl-4-({[2-(methylthio)ethyl][4'-(trifluoromethyl)-1,1'-biphenyl-3-yl]amino}methyl)phenoxy]acetate (96.4 mg, 0.19 mmol) in MeOH (2 mL) and THF (2 mL) at room temperature was added 2M NaOH (1 mL, 2 mmol). The resultant mixture was stirred for 16 h, and then the solvents were removed in vacuo. The residue was partitioned between CH$_2$Cl$_2$ (2×20 mL) and 2M HCl (20 mL). The organic solution was passed through a hydrophobic frit and the solvent was removed in vacuo affording the title compound as a yellow solid (94 mg).

$^1$H NMR (400 MHz; CDCl$_3$) δ: 2.15 (3H, s), 2.27 (3H, s), 2.76 (2H, t, J 7.5 Hz), 3.66 (2H, t, J 7.5 Hz), 4.55 (2H, s), 4.67 (2H, s), 6.68 (1H, d, J 8.5 Hz), 6.74 (1H, d, J 7.5 Hz), 6.87 (1H, s), 6.91 (1H, d, J 7 Hz), 7.02 (1H, d, J 8 Hz), 7.07 (1H, s), 7.29 (1H, m), 7.59 (2H, d, J 8 Hz), 7.65 (2H, d, J 8 Hz), CO$_2$H not observed.

LC/MS: m/z 487.8 [M−H]$^-$ R$_t$ 4.3 min.

EXAMPLE 10

[4-({Butyl[2-methyl-4'-(trifluoromethyl)-1,1'-biphenyl-3-yl]amino}methyl)-2-methylphenoxy]acetic acid

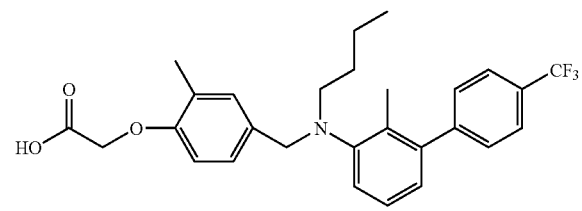

To a solution of ethyl [4-({butyl[2-methyl-4'-(trifluoromethyl)-1,1'-biphenyl-3-yl]amino}methyl)-2-methylphenoxy]acetate (110 mg, 0.21 mmol) in MeOH (2 mL) and THF (2 mL) at room temperature was added 2M NaOH (1 mL, 2 mmol). The resultant mixture was stirred for 2 h. The solvents were removed in vacuo and the residue was partitioned between CH$_2$Cl$_2$ (2×20 mL) and 2M HCl (20 mL). The organic solution was passed through a hydrophobic frit and the solvent was removed in vacuo affording the title compound as a white solid (103 mg).

$^1$H NMR (400 MHz; DMSO-d$^6$+DCl, 85° C.) δ: 0.82 (3H, t, J 7.5 Hz), 1.28 (2H, m), 1.42 (2H, m), 1.89 (3H, s), 2.03 (3H, s), 3.69 (2H, t, J 7.5 Hz), 4.59 (2H, br s), 4.61 (2H, s), 6.69 (1H, d, J 8.5 Hz), 6.98 (1H, d, J 2 Hz), 7.08 (1H, dd, J 8.5 Hz, 2 Hz), 7.21 (1H, d, J 7.5 Hz), 7.27 (2H, d, J 8 Hz), 7.47 (1H, t, J 8 Hz), 7.72 (2H, d, J 8 Hz), 7.82 (1H, d, J 8.5 Hz), CO$_2$H not observed.

LC/MS: m/z 486.4 [M+H]$^+$ R$_t$ 4.6 min.

EXAMPLE 11

[4-({(2-Methoxyethyl)[2-methyl-4'-(trifluoromethyl)-1,1'-biphenyl-3-yl]amino}methyl)-2-methylphenoxy]acetic acid

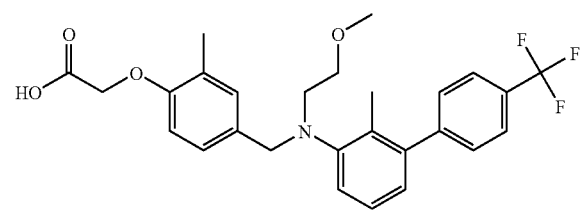

To a solution of ethyl [4-({(2-methoxyethyl)[2-methyl-4'-(trifluoromethyl)-1,1'-biphenyl-3-yl]amino}methyl)-2-methylphenoxy]acetate (500 mg, 0.97 mmol) in THF (6 mL) and MeOH (6 mL) was added NaOH (2M; 3 mL) and the resultant solution stirred for 2 h at room temperature. The mixture was concentrated in vacuo, acidified with 2M HCl and extracted with CH$_2$Cl$_2$. The organic solution was dried (Na$_2$SO$_4$) and the solvent removed in vacuo to afford the title compound as a colourless oil (453 mg).

$^1$H NMR (400 MHz; DMSO-d$^6$) δ: 2.09 (3H, s), 2.14 (3H, s), 3.05 (2H, m), 3.12 (3H, m), 3.32 (2H, m), 4.05 (2H, s), 4.6 (2H, m), 6.67 (1H, d, J 8.5 Hz), 6.89 (1H, m), 6.99–7.02 (2H, m), 7.17 (2H, m), 7.52 (2H, d, J 8 Hz), 7.73 (2H, d, J 8 Hz), 12.9 (1H, s, broad).

LC/MS: m/z 488 [M+H]$^+$, R$_t$ 4.06 min.

EXAMPLE 12

[4-({Butyryl[4'-(trifluoromethyl)-1,1'-biphenyl-3-yl]amino}methyl)-2 methylphenoxy]acetic acid

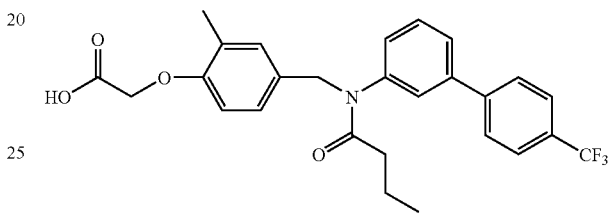

To a solution of ethyl [4-({butyryl[4'-(trifluoromethyl)-1,1'-biphenyl-3-yl]amino}methyl)-2-methylphenoxy]acetate (40 mg, 0.078 mmol) in methanol (2 mL) and tetrahydrofuran (2 mL), was added 2M sodium hydroxide (1 mL). After stirring for 1 h at room temperature the solvent was removed in vacuo and the residue acidified with 2M HCl, before extraction into ethyl acetate (2×15 mL). The organic solution was dried (MgSO$_4$) and the solvents removed in vacuo to afford the title compound as a white solid (28 mg).

$^1$H NMR (400 MHz; CDCl$_3$) δ: 0.84 (3H, t, J 7.5 Hz), 1.64 (2H, m), 2.08 (2H, m), 2.24 (3H, s), 4.67 (2H, s), 4.84 (2H, s), 6.64 (1H, d, J 8 Hz), 6.98–7.05 (3H, m), 7.12 (1H, br s), 7.45 (1H, t, J 8 Hz), 7.55 (3H, d, J 8 Hz), 7.69 (2H, d, J 8 Hz), CO$_2$H not observed.

LC/MS: m/z 485.9 [M+H]$^+$, R$_t$ 3.9 min.

EXAMPLE 13

[2-Methyl-4-({(propylsulfonyl)[4'-(trifluoromethyl)-1,1'-biphenyl-3-yl]amino}methyl)phenoxy]acetic acid

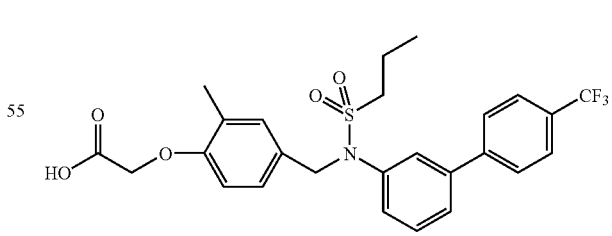

To a solution of ethyl [2-methyl-4-({(propylsulfonyl)[4'-(trifluoromethyl)-1,1'-biphenyl-3-yl]amino}methyl)phenoxy]acetate (20 mg, 0.036 mmol) in MeOH (1 mL) and THF (1 mL) at room temperature was added 2M NaOH (0.5 mL, 1 mmol). The resultant mixture was stirred for 2 h. The solvents were removed in vacuo and the residue was partitioned between CH$_2$Cl$_2$ (2×10 mL) and 2M HCl (10 mL).

The organic solution was passed though a hydrophobic frit and the solvent was removed in vacuo. Purification by autoprep. HPLC conducted on a Supelco ABZ+ column (5 μm, 10 cm×21.2 mm ID), eluting at a flow rate of 8 mL/min with a gradient of 50–95% B over 20 mins and held at 95% B for 10 mins. Where solvent A=0.1% $HCO_2H$ in $H_2O$ and solvent B=0.05% $HCO_2H$ in MeCN. The title compound was afforded as a yellow oil (10.7 mg).

$^1$H NMR (400 MHz; $CDCl_3$) δ: 1.06 (3H, t, J 7.5 Hz), 1.93 (2H, m), 2.23 (3H, s), 3.04 (2H, m), 4.64 (2H, s), 4.82 (2H, s), 6.61 (1H, d, J 8.5 Hz), 7.03 (1H, dd, J 8.5 Hz, 2 Hz), 7.09 (1H, d, J 2 Hz), 7.28 (1H, m), 7.39–7.50 (3H, m), 7.56 (2H, d, J 8 Hz), 7.68 (2H, d, J 8 Hz), $CO_2H$ not observed.

LC/MS: m/z 520.1 [M−H]$^-$, $R_t$ 3.6 min.

EXAMPLE 14

[4-({Butyl[4'-(trifluoromethyl)-1,1'-biphenyl-3-yl]amino}sulfonyl)-2-methylphenoxy]acetic acid

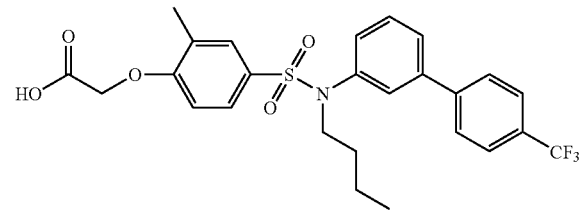

To a solution of ethyl [4-({butyl[4'-(trifluoromethyl)-1,1'-biphenyl-3-yl]amino}sulfonyl)-2-methylphenoxy]acetate (100 mg, 0.18 mmol) in methanol (4 mL) and tetrahydrofuran (4 mL), was added 2M NaOH aq. (2 mL). After stirring for 1 h at room temperature the solvent was removed in vacuo and the residue acidified with 2M HCl, before extraction into ethyl acetate (2×20 mL). The organic solution was dried ($MgSO_4$) and the solvents removed in vacuo to afford the title compound as a white solid (85 mg).

$^1$H NMR (400 MHz; $CDCl_3$) δ: 0.87 (3H, t, J 7 Hz), 1.30–1.45 (4H, m), 2.28 (3H, s), 3.55 (2H, t, J 7 Hz), 4.78 (2H, s), 6.74 (1H, d, J 8.5 Hz), 7.10 (1H, dm, J 8 Hz), 7.25 (1H, t, J 2 Hz), 7.39–7.47 (3H, m), 7.51–7.60 (3H, m), 7.69 (2H, d, J 8 Hz), $CO_2H$ not observed.

LC/MS: m/z 522.3 [M+H]$^+$, $R_t$ 4.5 min.

EXAMPLE 15

[2-Methyl-4-({pentyl[4'-(trifluoromethyl)-1,1'-biphenyl-3-yl]amino}sulfonyl)phenoxy]acetic acid

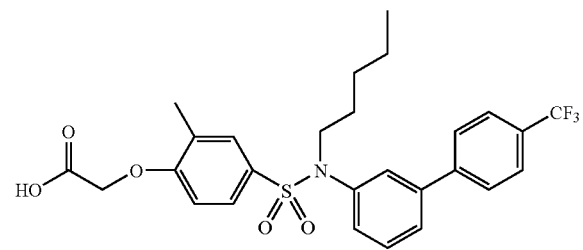

To a solution of ethyl [2-methyl-4-({pentyl[4'-(trifluoromethyl)-1,1'-biphenyl-3-yl]amino}sulfonyl)phenoxy]acetate (76 mg, 0.13 mmol) in MeOH (2 mL) and THF (2 mL) at room temperature was added 2M NaOH aq. (1 mL, 2 mmol). The resultant mixture was stirred for 1 h. The solvents were removed in vacuo and the residue was partitioned between $CH_2Cl_2$ (2×15 mL) and 2M HCl (10 mL). The organic solution was passed through a hydrophobic frit and the solvent was removed in vacuo affording the title compound as a white solid (75 mg).

$^1$H NMR (400 MHz; MeOH-d$^4$) δ: 0.85 (3H, t, J 7.5 Hz), 1.22–1.45 (6H, m), 2.23 (3H, s), 3.60 (2H, t, J 7 Hz), 4.81 (2H, s), 6.96 (1H, d, J 8.5 Hz), 7.14 (1H, dm, J 7 Hz), 7.23 (1H, t, J 2 Hz), 7.32 (1H, d, J 1.5 Hz), 7.40–7.50 (2H, m), 7.62–7.68 (3H, m), 7.75 (2H, d, J 8 Hz), $CO_2H$ not observed.

LC/MS: m/z 536.3 [M+H]+$R_t$ 4.5 min.

EXAMPLE 16

[4-({(2-Cyclopropylethyl)[4'-(trifluoromethyl)-1,1'-biphenyl-3-yl]amino}sulfonyl)-2-methylphenoxy]acetic acid

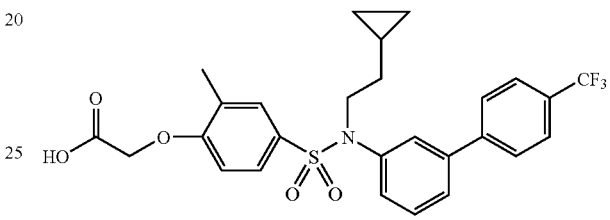

To a solution of ethyl [4-({(2-cyclopropylethyl)[4'-(trifluoromethyl)-1,1'-biphenyl-3-yl]amino}sulfonyl)-2-methylphenoxy]acetate (156 mg, 0.28 mmol) in MeOH (2 mL) and THF (2 mL) at room temperature was added 2M NaOH aq. (1 mL, 2 mmol). The resultant mixture was stirred for 2 h. The solvents were removed in vacuo and the residue was partitioned between EtOAc (2×20 mL) and 2M HCl (20 mL). The organic solution was dried ($MgSO_4$) and the solvent was removed in vacuo. Purification by SPE (5 g aminopropyl cartridge), loading crude material in $CH_2Cl_2$ and then washing with MeOH, prior to eluting with 5% $NH_3$ in MeOH. The 5% $NH_3$ in MeOH extract was concentrated in vacuo and the residue was partitioned between $CH_2Cl_2$ (20 mL) and 2M HCl (2 mL). The organic solution was dried ($MgSO_4$) and the solvent was removed in vacuo affording the title compound as a white solid (64.4 mg).

$^1$H NMR (400 MHz; MeOH-d$^4$) δ: −0.03 (2H, m), 0.40 (2H, m), 0.70 (1H, m), 1.32 (2H, q, J 7 Hz), 2.23 (3H, s), 3.68 (2H, t, J 7 Hz), 4.82 (2H, s), 6.96 (1H, d, J 9 Hz), 7.14 (1H, dm, J 8 Hz), 7.24 (1H, m), 7.32 (1H, m) 7.42–7.50 (2H, m), 7.62–7.68 (3H, m), 7.74 (2H, d, J 8.5 Hz), $CO_2H$ not observed.

LC/MS: m/z 531.9 [M−H]$^-$ $R_t$ 4.3 min.

EXAMPLE 17

{4-[(Butyl{4-[4-(trifluoromethyl)phenyl]pyrimidin-2-yl}amino)methyl]-2-methylphenoxy}acetic acid

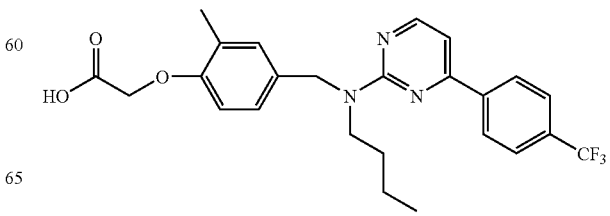

To a solution of ethyl {4-[(butyl{4-[4-(trifluoromethyl)phenyl]pyrimidin-2-yl}amino)methyl]-2-thylphenoxy}acetate (100 mg, 0.2 mmol) in methanol (2 mL) and tetrahydrofuran (2 mL) was added 2M sodium hydroxide (2 mL). After stirring for 1 h at room temperature the solvent was removed in vacuo and the residue was diluted with water (10 mL) and acidified with 2M HCl, before extraction into $CH_2Cl_2$ (2×40 mL). The organic solution was separated by hydrophobic frit and the solvents removed in vacuo to afford the title compound as a cream solid (85 mg).

$^1$H NMR (400 MHz; $CDCl_3$) δ: 0.95 (3H, t, J 7 Hz), 1.42 (2H, m), 1.68 (2H, m), 2.26 (3H, s), 3.74 (2H, m), 4.65 (2H, s), 4.96 (2H, s), 6.68 (1H, d, J 8.5 Hz), 7.05–7.15 (3H, m), 7.75 (2H, d, J 8 Hz), 8.15 (2H, d, J 8 Hz), 8.50 (1H, br s), $CO_2H$ not observed.

LC/MS: m/z 474.0 [M+H]$^+$, $R_t$ 4.3 min.

EXAMPLE 18

[4-({Butyl[4-(4-chlorophenyl)pyrimidin-2-yl]amino}methyl)-2-methylphenoxy]acetic acid

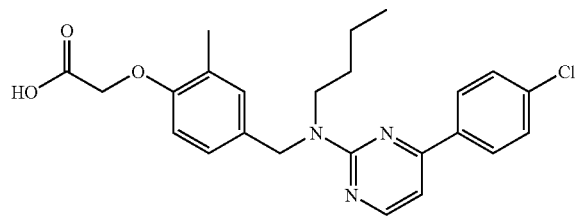

To a solution of ethyl [4-({butyl[4-(4-chlorophenyl)pyrimidin-2-yl]amino}methyl)-2-methylphenoxy]acetate (178 mg, 0.38 mmol) in THF (3 mL) and MeOH (3 mL) was added NaOH (2M; 2 mL) and the resultant mixture agitated for 1.5 h. The mixture was evaporated and acidified with 2M HCl, extracted with $CH_2Cl_2$ (10 mL), EtOAc (10 mL). The aqueous was filtered, the filtered solids and solvent extracts combined and the solvent removed in vacuo to afford the title compound as a white solid (161 mg).

$^1$H NMR (400 MHz; MeOH-$d^4$) δ: 0.99 (3H, t, J 7 Hz), 1.38–1.48 (2H, m), 1.63–1.75 (2H, m), 2.26 (3H, s), 3.6–3.8 (2H, broad s), 4.7 (2H, s), 4.91–5.09 (2H, broad s), 6.81 (1H, d, J 8.5 Hz), 7.09–7.2 (2H, m), 7.50 (1H, d, J 6 Hz), 7.61 (2H, d, J 8.5 Hz), 8.24 (2H, d, J 8.5 Hz), 8.35 (1H, d, J 6 Hz). $CO_2H$ not observed.

LC/MS: m/z 440 [M+H]$^+$, $R_t$ 4.35 min.

EXAMPLE 19

{4-[((2-Methoxyethyl){4-[4-(trifluoromethyl)phenyl]pyrimidin-2-yl}amino)methyl]-2-methylphenoxy}acetic acid

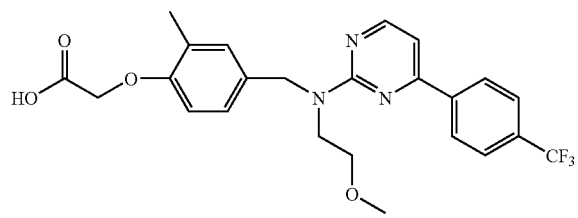

To a solution of ethyl {4-[((2-methoxyethyl){4-[4-(trifluoromethyl)phenyl]pyrimidin-2-yl}amino)methyl]-2-methylphenoxy}acetate (80 mg, 0.16 mmol) in methanol (1.5 mL) and tetrahydrofuran (1.5 mL) was added 2M sodium hydroxide (1.5 mL). The resulting mixture was stirred at room temperature for 1 h. The solvents were removed in vacuo and the residue was diluted with water (10 mL) acidified with 2M HCl and extracted ethyl acetate (2×30 mL). The organic solution was dried ($MgSO_4$) and the solvents removed in vacuo, to afford the title compound as a cream solid (72 mg).

$^1$H NMR (400 MHz; $CDCl_3$) δ: 2.26 (3H, s), 3.36 (3H, s), 3.70 (2H, m), 3.93 (2H, m), 4.65 (2H, s), 5.04 (2H, br s), 6.68 (1H, d, J 8 Hz), 7.04–7.14 (3H, m), 7.74 (2H, d, J 8 Hz), 8.14 (2H, d, J 8 Hz), 8.48 (1H, J 5 Hz), ($CO_2H$ not observed).

LC/MS: m/z 476.3 [M+H]$^+$, $R_t$ 3.9 min.

EXAMPLE 20

(4-{[[4-(4-Chlorophenyl)pyrimidin-2-yl](2-methoxyethyl)amino] methyl}-2-methylphenoxy)acetic acid

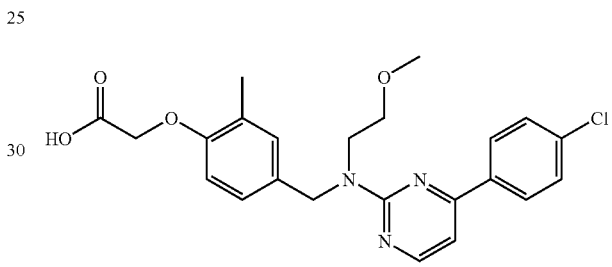

Prepared from ethyl (4-{[[4-(4-chlorophenyl)pyrimidin-2-yl](2-methoxyethyl) amino]methyl}-2-methylphenoxy)acetate using the procedure described for Example 18.

$^1$H NMR (400 MHz; MeOH-$d^4$) δ: 2.21(3H, s), 3.32 (3H, s), 3.62 (2H, t, J 5.5 Hz), 3.83 (2H, t, J 5.5 Hz), 4.64 (2H, s), 4.95 (2H, s), 6.70 (1H, d, J 8 Hz), 7.00–7.10 (2H, m), 7.18 (1H, d, J 5.5 Hz), 7.48 (2H, d, J 8.5 Hz), 8.10 (2H, d, J 8.5 Hz), 8.35 (1H, d, J 5.5 Hz), $CO_2H$ not observed.

LC/MS: m/z 442 [M+H]$^+$, $R_t$ 3.89 min

EXAMPLE 21

{2-Methyl-4-[(propyl{4-[4-(trifluoromethyl)phenyl]pyrimidin-2-yl}amino)methyl]phenoxy}acetic acid

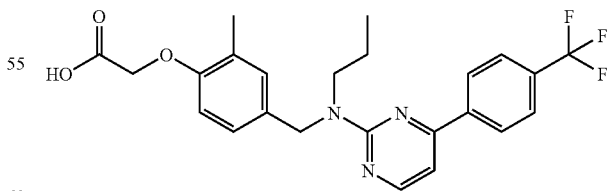

Prepared from ethyl {2-methyl-4-[(propyl{4-[4-(trifluoromethyl)phenyl]pyrimidin-2-yl}amino)methyl]phenoxy}acetate using the procedure described for Example 18.

$^1$H NMR (400 MHz; MeOH-$d^4$) δ: 0.96 (3H, m), 1.7 (2H, m), 2.25 (3H, s), 3.63 (2H, m), 4.68 (2H, s), 4.9 (2H, s), 6.75

(1H, dm, J 8 Hz), 7.02–7.24 (3H, m), 7.73–7.84 (2H, m), 8.21–8.34 (2H, m), 8.38–8.47 (1H, m), $CO_2H$ not observed.

LC/MS: m/z 460 [M+H]$^+$, $R_t$ 4.25 min

EXAMPLE 22

{4-[(Butyl{6-[4-(trifluoromethyl)phenyl]pyrazin-2-yl}amino)methyl]-2-methylphenoxy}acetic acid

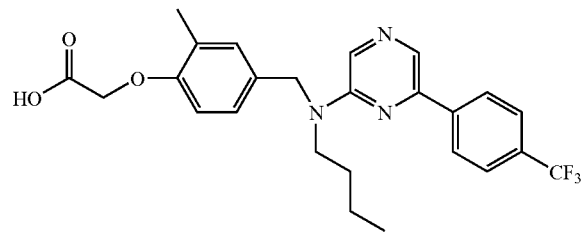

To a solution of ethyl {4-[(butyl{6-[4-(trifluoromethyl)phenyl]pyrazin-2-yl}amino)methyl]-2-methylphenoxy}acetate (150 mg, 0.3 mmol) in methanol (4 mL) and tetrahydrofuran (4 mL), was added 2M NaOH (2 mL). After stirring for 1 h at room temperature the solvent was removed in vacuo and the residue acidified with 2M HCl, before extraction into ethyl acetate (2×50 mL). The organic solution was dried (MgSO$_4$) and the solvents removed in vacuo to afford the title compound as a bright yellow solid (115 mg).

$^1$H NMR (400 MHz; CDCl$_3$) δ: 0.96 (3H, t, J 7.5 Hz), 1.40 (2H, m), 1.66 (2H, m), 2.26 (3H, s), 3.61 (2H, t, J 7.5 Hz), 4.66 (2H, s), 4.73 (2H, s), 6.68 (1H, d, J 8.5 Hz), 6.99 (1H, dm, J 8.5 Hz), 7.05 (1H, s), 7.70 (2H, d, J 8 Hz), 7.91 (1H, s), 8.09 (2H, d, J 8 Hz), 8.29 (1H, s), $CO_2H$ not observed.

LC/MS: m/z 473.9 [M+H]$^+$, $R_t$ 4.4 min.

EXAMPLE 23

[4-({Butyl[6-(4-methylphenyl)pyrazin-2-yl]amino}methyl)-2-methylphenoxy]acetic acid

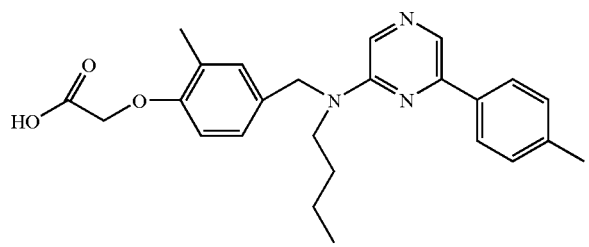

To a solution of ethyl [4-({butyl[6-(4-methylphenyl)pyrazin-2-yl]amino}methyl)-2-methylphenoxy]acetate (39 mg, 0.087 mmol) in methanol (1 mL) and tetrahydrofuran (1 mL), was added 2M sodium hydroxide (1 mL). After shaking for 1 h at room temperature the solvent was evaporated and the residue was then acidified with 2M HCl and extracted CH$_2$Cl$_2$ (2×10 mL). The organic solution separated by hydrophobic frit and the solvents removed in vacuo to afford the title compound as a bright yellow solid (34 mg).

$^1$H NMR (400 MHz; MeOH-d$^4$) δ: 0.98 (3H, t, J 7 Hz), 1.43 (2H, m), 1.69 (2H, m), 2.24 (3H, s), 2.41 (3H, s), 3.72 (2H, t, J 7.5 Hz), 4.66 (2H, s), 4.84 (2H, s), 6.76 (1H, d, J 8.5 Hz), 7.08 (1H, dm, J 8.5 Hz), 7.13 (1H, s), 7.34 (2H, d, J 8 Hz), 7.92 (1H, s), 7.98 (2H, d, J 8 Hz), 8.29 (1H, s), $CO_2H$ not observed.

LC/MS: m/z 420.2 [M+H]$^+$, $R_t$ 4.2 min.

EXAMPLE 24

{4-[((2-Methoxyethyl){6-[4-(trifluoromethyl)phenyl]pyrazin-2-yl}amino)methyl]-2-methylphenoxy}acetic acid

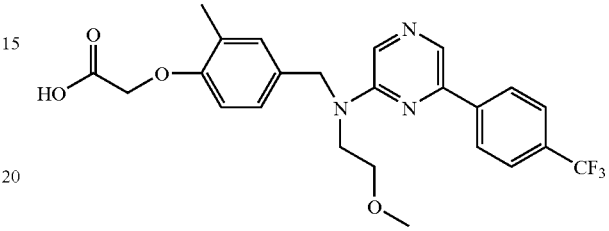

To a solution of ethyl {4-[((2-methoxyethyl){6-[4-(trifluoromethyl)phenyl]pyrazin-2-yl}amino)methyl]-2-methylphenoxy}acetate (160 mg, 0.32 mmol) in methanol (2 mL) and tetrahydrofuran (2 mL) was added 2M sodium hydroxide (2 mL). The resulting mixture was stirred at room temperature for 1 h. The solvents were removed in vacuo and the residue was diluted with water (10 mL) acidified with 2M HCl and extracted with ethyl acetate (2×30 mL). The organic solution was dried (MgSO$_4$) and the solvents removed in vacuo, to afford the title compound as a bright yellow solid (140 mg).

$^1$H NMR (400 MHz; CDCl$_3$) δ: 2.26 (3H, s), 3.34 (3H, s), 3.66 (2H, t, J 5.5 Hz), 3.86 (2H, t, J 5.5 Hz), 4.67 (2H, s), 4.82 (2H, s), 6.68 (1H, d, J 8.5 Hz), 7.00 (1H, dd, J 8.5, 2 Hz), 7.06 (1H, m), 7.72 (2H, d, J 8 Hz), 7.99 (1H, s), 8.07 (2H, d, J 8 Hz), 8.30 (1H, s), $CO_2H$ not observed.

LC/MS: m/z 476.3 [M+H]$^+$, $R_t$ 3.8 min.

EXAMPLE 25

(4-{[Butyl(2,4'-dimethyl-1,1'-biphenyl-3-yl)amino]methyl}-2-methylphenoxy)acetic acid (Method A)

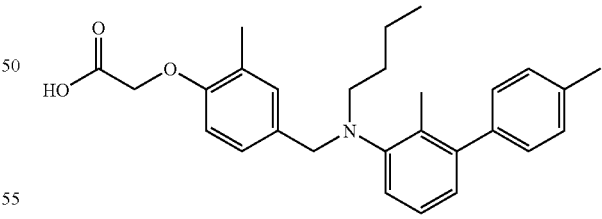

A mixture of ethyl (4-{[(3-bromo-2-methylphenyl)(butyl)amino]methyl}-2-methylphenoxy)acetate (90 mg, 0.2 mmol), 4-methylphenylboronic acid (32 mg, 0.23 mmol), tetrakis(triphenylphosphine)palladium (0) (5 mg, 4.32 mmol), sodium carbonate (55 mg, 0.52 mmol) in 1,2-dimethoxyethane (10 mL) and water (5 mL) was heated at 90° C. for 18 h under nitrogen. The reaction mixture was cooled and the solvents removed in vacuo. Purification by SPE (C$_{18}$, 10 g) eluting with 20 mL each of 5%, 10%, 30%, 50% acetonitrile/water, acetonitrile, MeOH. Further purification with SPE (amino propyl, 10 g), eluted with CH$_2$Cl$_2$ (40 mL), CHCl₃ (20 mL), ether (20 mL), EtOAc (40 mL), MeOH (20 mL), 10% NH₃/MeOH (40 mL) afforded the title compound as a colourless oil (50 mg).

$^1$H NMR (400 MHz; CDCl₃) δ: 0.67 (3H, t, J 7 Hz), 1.07 (2H, m), 1.25 (2H, m), 1.91 (3H, s), 2.18 (3H, s), 2.33 (3H, s), 2.72 (2H, m), 3.76 (2H, s), 4.09 (2H, s), 6.48 (1H, d, J 8 Hz), 6.79–6.90 (4H, m), 7.02 (1H, t, J 7.5 Hz), 7.12 (4H, s), CO₂H not observed.

LC/MS: m/z 432 [M+H]⁺, R$_t$ 4.33 min.

EXAMPLE 25

(4-{[Butyl(2,4'-dimethyl-1,1'-biphenyl-3-yl)amino]methyl}-2-methylphenoxy)acetic acid (Method B)

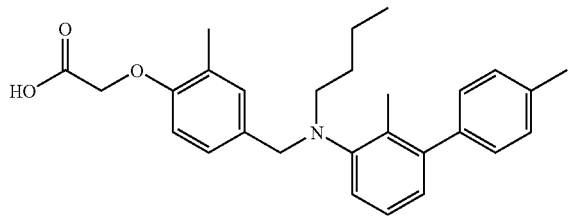

Ethyl (4-{[butyl(2,4'-dimethyl-1,1'-biphenyl-3-yl)amino]methyl}-2-methylphenoxy)acetate (12.7 g, 27.6 mmol) was dissolved in THF (210 mL) and water (70 ml) was added, followed by 2M aq. NaOH (61 mL, 122 mmol). The reaction was stirred at room temperature for 1/2 hr and then evaporated to give a white slurry. The suspension was diluted with water (100 mL) and pH adjusted to pH7 with 2M aq HCl. EtOAc (200 mL) the aqueous layer was separated and extracted with EtOAc (2×100 mL). The combined organics were washed with brine (200 mL), dried (Na₂SO₄) and concentrated In vacuo to give the title compound as a white foam (11.1 g).

$^1$H NMR (400 MHz; DMSO-d⁶) δ: 0.79 (3H, t, J 7 Hz), 1.20 (2H, m), 1.36 (2H, m), 2.14 (3H, s), 2.21 (3H, s), 2.34 (3H, s), 2.87 (2H, m), 3.92 (2H, s), 4.64 (2H, s), 6.72 (1H, d, J 8 Hz), 6.87 (1H, d, J 7.5 Hz), 7.03–7.17 (4H, m), 7.22 (4H, s), 12.95 (1H, s, broad).

EXAMPLE 26

(4-{[Butyl (4'-fluoro-2-methyl-1,1'-biphenyl-3-yl)amino]methyl}-2-methylphenoxy)acetic acid

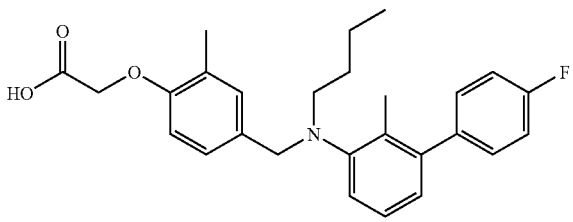

Prepared from ethyl (4-{[(3-bromo-2-methylphenyl)(butyl)amino]methyl}-2-methylphenoxy)acetate and 4-fluorophenylboronic acid using the procedure described for Example 25 (Method A).

$^1$H NMR (400 MHz; CDCl₃) δ: 0.73 (3H, t, J 7.5 Hz), 1.13 (2H, m), 1.3 (2H, m), 2.01 (3H, s), 2.16 (3H, s), 2.78 (2H, t, J 7.5 Hz), 3.84 (2H, s), 4.17 (2H, s), 6.50 (1H, d, J 8 Hz), 6.85–7.10 (7H, m), 7.18 (2H, m), CO₂H not observed.

LC/MS: m/z 436 [M+H]⁺, R$_t$ 4.25 min.

EXAMPLE 27

(4-{[Butyl(4'-cyano-2-methyl-1,1'-biphenyl-3-yl)amino]methyl}-2-methylphenoxy)acetic acid

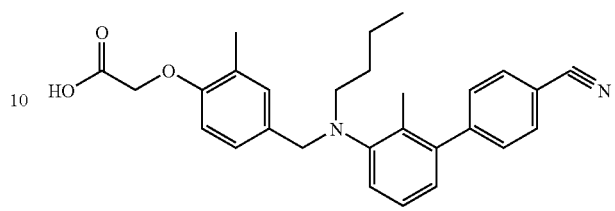

Prepared from ethyl (4-{[(3-bromo-2-methylphenyl)(butyl)amino]methyl}-2-methylphenoxy)acetate and 4-cyanophenylboronic acid using the procedure described for Example 25 (Method A).

$^1$H NMR (400 MHz; CDCl₃) δ: 0.75 (3H, t, J 7.5 Hz), 1.14 (2H, m), 1.31 (2H, m), 2.03 (3H, s), 2.15 (3H, s), 2.8 (2H, t, J 7 Hz), 3.86 (2H, s), 4.17 (2H, s) 6.51 (1H, d, J 8.5 Hz) 6.84–6.89 (2H, m), 6.93 (1H, s), 7.02 (1H, d, J 8 Hz), 7.11 (1H, t, J 8 Hz), 7.33 (2H, d, J 8.5 Hz), 7.61 (2H, d, J 8.5 Hz), CO₂H not observed.

LC/MS: m/z 443 [M+H]⁺, R$_t$ 4.13 min.

EXAMPLE 28

(4-{[Butyl(4-methoxy-2-methyl-1,1'-biphenyl-3-yl)amino]methyl}-2-methylphenoxy)acetic acid

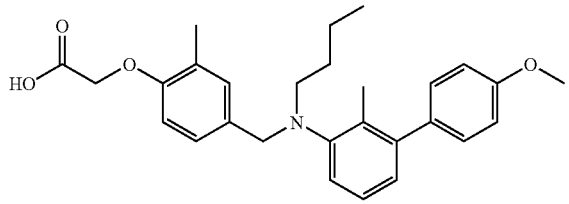

Prepared from ethyl (4-{[(3-bromo-2-methylphenyl)(butyl)amino]methyl}-2-methylphenoxy)acetate and 4-methoxyphenylboronic acid using the procedure described for Example 25 (Method A).

$^1$H NMR (400 MHz; CDCl₃) δ: 0.71 (3H, t, J 7.5 Hz), 1.11 (2H, m), 1.29 (2H, m), 1.99 (3H, s), 2.2 (3H, s), 2.76 (2H, t, J 7.5 Hz), 3.78 (3H, s), 3.82 (2H, s), 4.14 (2H, s), 6.49 (1H, d, J 8.5 Hz), 6.82–6.95 (6H, m), 7.05 (1H, t, J 7.5 Hz), 7.17 (2H, d, J 8.5 Hz), CO₂H not observed.

LC/MS: m/z 448 [M+H]⁺, R$_t$ 4.01 min.

EXAMPLE 29

(4-{[Butyl(4'-chloro-2-methyl-1,1'-biphenyl-3-yl)amino]methyl}-2-methylphenoxy)acetic acid

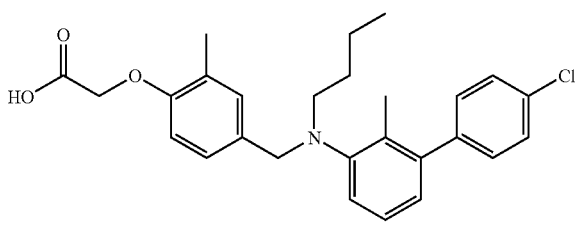

Prepared from ethyl (4-{[(3-bromo-2-methylphenyl)(butyl)amino]methyl}-2-methylphenoxy)acetate and 4-chlorophenylboronic acid using the procedure described for Example 25 (Method A).

$^1$H NMR (400 MHz; CDCl$_3$) δ: 0.71 (3H, t, J 7.5 Hz), 1.10 (2H, m), 1.28 (2H, m), 1.96 (3H, s), 2.15 (3H, s), 2.76 (2H, t, J 7 Hz), 3.8 (2H, s), 4.1 (2H, s), 6.47 (1H, d, J 8.5 Hz), 6.8–6.96 (4H, m), 7.05 (1H, t, J 7.5 Hz), 7.14 (2H, d, J 8.5 Hz), 7.28 (2H, d, J 8.5 Hz), CO$_2$H not observed.

LC/MS: m/z 452 [M+H]$^+$, R$_t$ 4.48 min.

EXAMPLE 30

(4-{[(4'-Chloro-2-methyl-1,1'-biphenyl-3-yl)(2-methoxyethyl)amino]methyl}-2-methylphenoxy) acetic acid

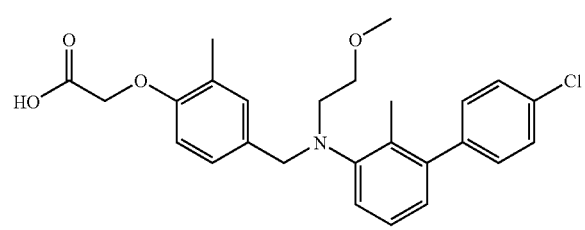

Prepared from 4-chlorophenylboronic acid and ethyl (4-{[(3-bromo-2-methylphenyl)(2-methoxyethyl)amino]methyl}-2-methylphenoxy)acetate using the procedure described for Example 25 (Method A).

$^1$H NMR (400 MHz; CDCl$_3$) δ: 2.03 (3H, s), 2.16 (3H, s), 3.01 (2H, t, J 6 Hz), 3.11 (3H, s), 3.25 (2H, t, J 6 Hz), 3.92 (2H, s), 4.18 (2H, s) 6.53 (1H, d, J 8.5 Hz), 6.84–6.96 (3H, m), 7.0–7.1 (2H, m), 7.15 (2H, d, J 8.5 Hz), 7.29 (2H, d, J 8.5 Hz), CO$_2$H not observed.

LC/MS: m/z 454 [M+H]$^+$, R$_t$ 4.06 min.

EXAMPLE 31

(4-{[(2,4'-Dimethyl-1,1'-biphenyl-3-yl)(2-methoxyethyl)amino]methyl}-2-ethylphenoxy)acetic acid

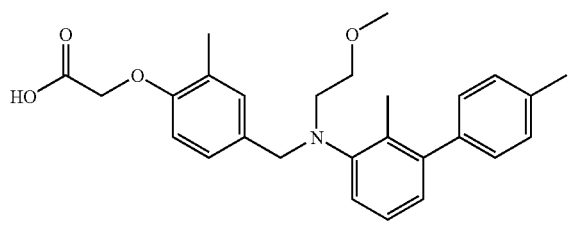

Prepared from 4-methylphenylboronic acid and ethyl (4-{[(3-bromo-2-methylphenyl)(2-methoxyethyl)amino]methyl}-2-methylphenoxy)acetate using the procedure described for Example 25 (Method A).

$^1$H NMR (400 MHz; CDCl$_3$) δ: 2.10 (3H, s), 2.22 (3H, s), 2.36 (3H, s), 3.04 (2H, t, J 6 Hz), 3.14 (3H, s), 3.29 (2H, t, J 6 Hz), 3.96 (2H, s), 4.27 (2H, s), 6.60 (1H, m), 6.9–7.14 (5H, m), 7.16 (4H, s), CO$_2$H not observed.

LC/MS: m/z 434 [M+H]$^+$, R$_t$ 3.94 min.

EXAMPLE 32

(4-{[(2-Methoxyethyl)(4'-methoxy-2-methyl-1,1'-biphenyl-3-yl)amino]methyl}-2-methylphenoxy) acetic acid

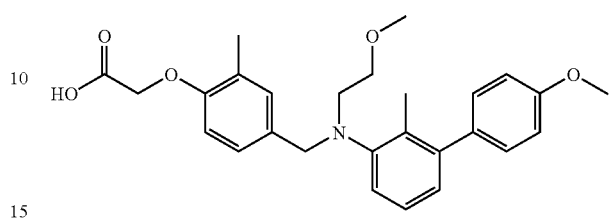

Prepared from 4-methoxyphenylboronic acid and ethyl (4-{[(3-bromo-2-methylphenyl)(2-methoxyethyl)amino]methyl}-2-methylphenoxy)acetate using the procedure described for Example 25 (Method A).

$^1$H NMR (400 MHz; CDCl$_3$) δ: 2.04 (3H, s), 2.2 (3H, s), 3.01 (2H, t, J 6 Hz), 3.1 (3H, s), 3.25 (2H, t, J 6 Hz), 3.79 (3H, s), 3.92 (2H, s), 4.19 (2H, s), 6.56 (1H, d, J 8.5 Hz), 6.86–7.09 (7H, m), 7.165 (2H, J 8.5 Hz), CO$_2$H not observed.

LC/MS: m/z 450 [M+H]$^+$, R$_t$ 3.68 min.

EXAMPLE 33

(2-Methyl-4-{[[2-methyl-4'-(trifluoromethyl)-1,1'-biphenyl-3-yl](propyl)amino]methyl}phenoxy)acetic acid

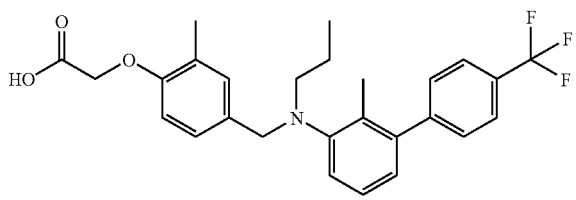

Prepared from 4-(trifluoromethyl)phenylboronic acid and ethyl (4-{[(3-bromo-2-methylphenyl)(propyl)amino]methyl}-2-methylphenoxy)acetate using the procedure described for Example 25 (Method A).

$^1$H NMR (400 MHz; CDCl$_3$) δ: 0.7 (3H, t, J 7 Hz), 1.34 (2H, m), 2.04 (3H, s), 2.16 (3H, s), 2.76 (2H, t, J 7 Hz), 3.86 (2H, s), 4.2 (2H, s), 6.52 (1H, d, J 8.5 Hz), 6.83–7.1 (5H, m), 7.33 (2H, d, J 8 Hz), 7.57 (2H, d, J 8 Hz), CO$_2$H not observed.

LC/MS: m/z 472 [M+H]$^+$, R$_t$ 4.35 min.

EXAMPLE 34

(4-{[(4'-Chloro-2-methyl-1,1'-biphenyl-3-yl)(propyl)amino]methyl}-2-methylphenoxy)acetic acid

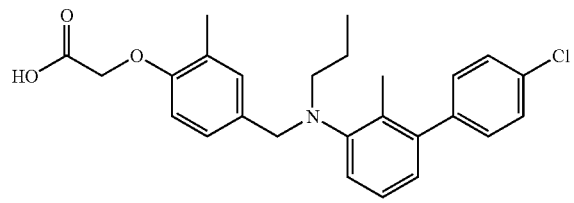

Prepared from 4-chlorophenylboronic acid and ethyl (4-{[(3-bromo-2-methylphenyl)(propyl)amino]methyl}-2-methylphenoxy)acetate using the procedure described Example 25.

$^1$H NMR (400 MHz; CDCl$_3$) δ: 0.71 (3H, t, J 7 Hz), 1.34 (2H, m), 2.04 (3H, s), 2.17 (3H, s), 2.75 (2H, t, J 7 Hz), 3.85 (2H, s), 4.21 (2H, s), 6.5 (1H, d, J 8.5 Hz), 6.83–7.0 (4H, m), 7.07 (1H, t, J 8 Hz), 7.16 (2H, d, J 8.5 Hz), 7.29 (2H, d, J 8.5 Hz), CO$_2$H not observed.

LC/MS: m/z 438 [M+H]$^+$, R$_t$ 4.39 min.

EXAMPLE 35

(4-{[(2,4'-Dimethyl-1,1'-biphenyl-3-yl)(propyl) amino]methyl}-2-methylphenoxy)acetic acid

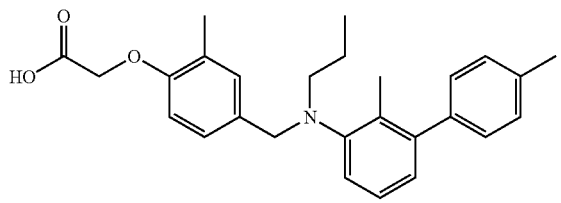

Prepared from 4-methylphenylboronic acid and ethyl (4-{[(3-bromo-2-methylphenyl)(propyl)amino]methyl}-2-methylphenoxy)acetate using the procedure described for Example 25 (Method A).

$^1$H NMR (400 MHz; CDCl$_3$) δ: 0.7 (3H, t, J 7 Hz), 1.33 (2H, m), 2.03 (3H, s), 2.21 (3H, s), 2.35 (3H, s), 2.74 (2H, t, J 7 Hz), 3.85 (2H, s), 4.19 (2H, s), 6.51 (1H, d, J 8.5 Hz), 6.85–6.97 (4H, m), 7.06 (1H, t, J 8 Hz), 7.14 (4H, s), CO$_2$H not observed.

LC/MS: m/z 418 [M+H]$^+$, R$_t$ 4.15 min.

EXAMPLE 36

(4-{[(4'-Fluoro-2-methyl-1,1'-biphenyl-3-yl)(propyl) amino]methyl}-2-methylphenoxy)acetic acid

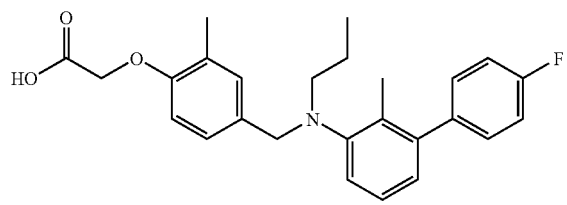

Prepared from 4-fluorophenylboronic acid and ethyl (4-{[(3-bromo-2-methylphenyl)(propyl)amino]methyl}-2-methylphenoxy)acetate using the procedure described for Example 25 (Method A).

$^1$H NMR (400 MHz; CDCl$_3$) δ: 0.69 (3H, t, J 7 Hz), 1.31 (2H, m), 2.01 (3H, s), 2.16 (3H, s), 2.74 (2H, J 7 Hz), 3.83 (2H, s), 4.16 (2H, s), 6.49 (1H, d, J 8 Hz), 6.83–7.09 (7H, m), 7.17 (2H, m) CO$_2$H not observed.

LC/MS: m/z 422 [M+H]$^+$, R$_t$ 4.08 min.

EXAMPLE 37

(4-{[(4'-Cyano-2-methyl-1,1'-biphenyl-3-yl)(propyl) amino]methyl}-2-methylphenoxy)acetic acid

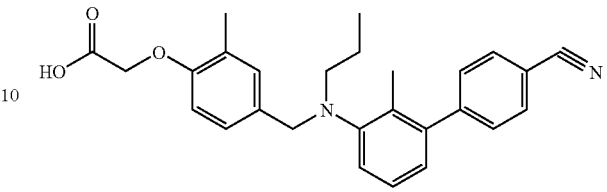

Prepared from 4-cyanophenylboronic acid and ethyl (4-{[(3-bromo-2-methylphenyl)(propyl)amino]methyl}-2-methylphenoxy)acetate using the procedure described for Example 25 (Method A).

$^1$H NMR (400 MHz; CDCl$_3$) δ: 0.8 (3H, t, J 7 Hz), 1.43 (2H, m), 2.22 (6H, s), 2.86 (2H, t, J 7 Hz), 3.99 (2H, s), 4.57 (2H, s), 6.63 (1H, d, J 8 Hz), 6.905 (1H, d, J 7.5 Hz), 7.02–7.22 (4H, m), 7.41 (2H, d, J 8 Hz), 7.68 (2H, d, J 8 Hz), CO$_2$H not observed.

LC/MS: m/z 429 [M+H]$^+$, R$_t$ 4.01 min.

EXAMPLE 38

(4-{[(4'-Methoxy-2-methyl-1,1'-biphenyl-3-yl)(propyl)amino] methyl}-2-methylphenoxy)acetic acid

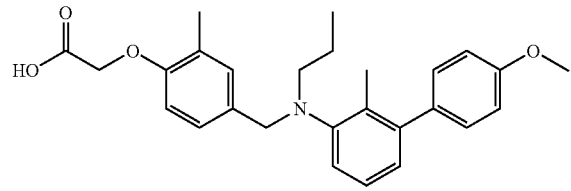

Prepared from 4-methoxyphenylboronic acid and ethyl (4-{[(3-bromo-2-methylphenyl)(propyl)amino]methyl}2-methylphenoxy)acetate using the procedure described for Example 25 (Method A).

$^1$H NMR (400 MHz; CDCl$_3$) δ: 0.7 (3H, t, J 7 Hz), 1.33 (2H, m), 2.04 (3H, s), 2.22 (3H, s), 2.74 (2H, t, J 7 Hz), 3.79 (3H, s), 3.85 (2H, s), 4.21 (2H, s), 6.52 (1H, d, J 8 Hz), 6.84–6.98 (6H, m), 7.06 (1H, t, J 8 Hz), 7.18 (2H, J 8.5 Hz), CO$_2$H not observed.

LC/MS: m/z 434 [M+H]$^+$, R$_t$ 3.86 min.

EXAMPLE 39

{4-[(Butyl{5-methyl-6-[4-(trifluoromethyl)phenyl] pyrimidin-4-yl}amino)methyl]-2-methylphenoxy}acetic acid

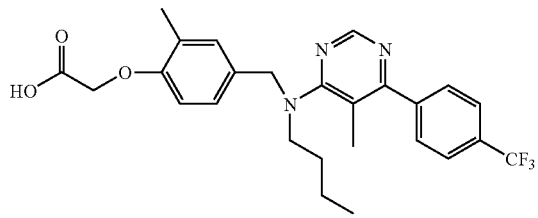

To a solution of ethyl {4-[(butyl{5-methyl-6-[4-(trifluoromethyl)phenyl]pyrimidin-4-yl}amino)methyl]-2-methylphenoxy}acetate (190 mg, 0.37 mmol) in methanol (4 mL) and tetrahydrofuran (4 mL) was added 2M sodium hydroxide (4 mL). The resulting mixture was stirred at room temperature for 2 h. The solvents were removed in vacuo and the residue was diluted with water (20 mL), acidified with 2M HCl and extracted ethyl acetate (50 mL). The organic solution was washed with brine (20 mL), dried (MgSO$_4$) and the solvents removed in vacuo, to afford the title compound as a white foam (180 mg).

$^1$H NMR (400 MHz; CDCl$_3$)δ: 0.94 (3H, t, J 7.5 Hz), 1.34 (2H, m), 1.70 (2H, m), 2.17 (3H, s), 2.26 (3H, s), 3.60 (2H, t, J 7.5 Hz), 4.63 (2H, s), 4.83 (2H, s), 6.68 (1H, d, J 8 Hz), 6.96 (1H, d, J 8 Hz), 7.02 (1H, s), 7.69 (2H, d, J 8 Hz), 7.75 (2H, d, J 8 Hz), 8.71 (1H, s), CO$_2$H not observed.

LC/MS: m/z 488.1 [M+H]$^+$, R$_t$3.6 min.

EXAMPLE 40

[4-({Butyl[6-(4-methoxyphenyl)-5-methylpyrimidin-4-yl]amino}methyl)-2-methylphenoxy]acetic acid

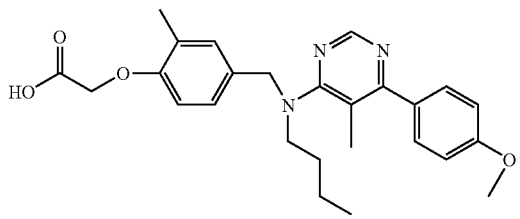

To a solution of ethyl [4-({butyl[6-(4-methoxyphenyl)-5-methylpyrimidin-4-yl]amino}methyl)-2-methylphenoxy]acetate (62 mg, 0.13 mmol) in methanol (2 mL) and tetrahydrofuran (2 mL), was added 2M sodium hydroxide (1 mL). After shaking for 1 h at room temperature the solvent was removed. The residue was then acidified with 0.5M HCl aq. (20 mL), before extraction into EtOAc (2×25 mL). The organic solution was washed with brine, dried (MgSO$_4$) and the solvents removed in vacuo to afford the title compound as a pale yellow solid (58 mg).

$^1$H NMR (400 MHz; CDCl$_3$) δ: 0.95 (3H, t, J 7.5 Hz), 1.33 (2H, m), 1.69 (2H, m), 2.23 (3H, s), 2.26 (3H, s), 3.63 (2H, t J 7 Hz), 3.84 (3H, s), 4.66 (2H, s), 4.88 (2H, s), 6.70 (1H, d, J 8 Hz), 6.90–7.05 (4H, m), 7.58 (2H, d, J 8.5 Hz), 8.69 (1H, s), CO$_2$H not observed.

LC/MS: m/z 450.2 [M+H]$^+$, R$_t$2.9 min.

EXAMPLE 41

[4-({Butyl[5-methyl-6-(4-methylphenyl)pyrimidin-4-yl]amino}methyl)-2-methylphenoxy]acetic acid

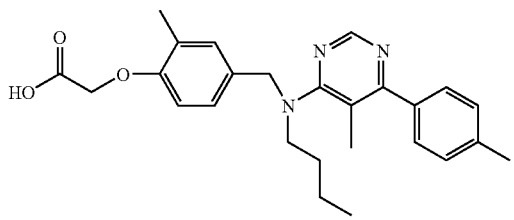

Prepared from ethyl [4-({butyl[5-methyl-6-(4-methylphenyl)pyrimidin-4-yl]amino}methyl)-2-methylphenoxy]acetate (58 mg, 0.126 mmol) using the procedure described for Example 40.

$^1$H NMR (400 MHz; CDCl$_3$) δ: 0.95 (3H, t, J 7.5 Hz), 1.34 (2H, m), 1.70 (2H, m), 2.22 (3H, s), 2.26 (3H, s), 2.40 (3H, s), 3.64 (2H, m), 4.65 (2H, s), 4.89 (2H, s), 6.71 (1H, d, J 8 Hz), 6.95 (1H, d, J 8 Hz), 7.00 (1H, s), 7.32 (2H, d, J 8 Hz), 7.48 (2H, d, J 8 Hz), 8.70 (1H, s), CO$_2$H not observed.

LC/: m/z 434.3 [M+H]$^+$, R$_t$3.1 min.

EXAMPLE 42

[4-({Butyl[6-(4-chlorophenyl)-5-methylpyrimidin-4-yl]amino}methyl)-2-methylphenoxy]acetic acid

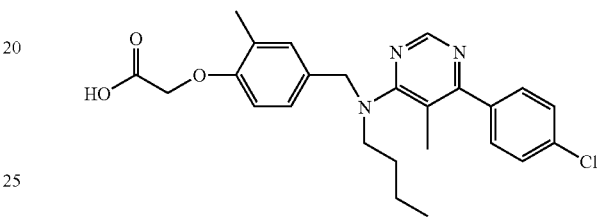

Prepared from ethyl [4-({butyl[6-(4-chlorophenyl)-5-methylpyrimidin-4-yl]amino}methyl)-2-methylphenoxy]acetate (98 mg, 0.203 mmol) using the procedure described for Example 40.

$^1$H NMR (400 MHz; CDCl$_3$) δ: 0.95 (3H, t, J 7 Hz), 1.34 (2H, m), 1.70 (2H, m), 2.18 (3H, s), 2.26 (3H, s), 3.62 (2H, t, J 7.5 Hz), 4.64 (2H, s), 4.85 (2H, s), 6.69 (1H, d, J 8 Hz), 6.95 (1H, d), 7.01 (1H, s), 7.45–7.54 (4H, m), 8.69 (1H, s), CO$_2$H not observed.

LC/MS: m/z 454.2 [M+H]$^+$, R$_t$3.5 min.

EXAMPLE 43

[4-({Butyl[6-(4-chlorophenyl)-2-pyrazin-2-yl]amino}methyl)-2-methylphenoxy]acetic acid

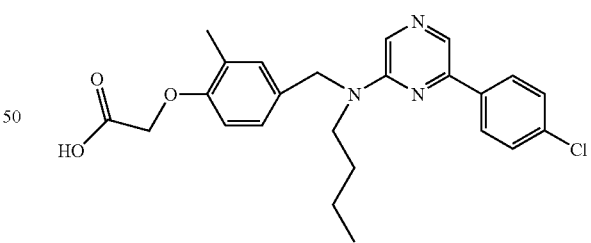

To a solution of ethyl [4-({butyl[6-(4-chlorophenyl)pyrazin-2-yl]amino}methyl)-2-methylphenoxy]acetate (78 mg, 0.17 mmol) in methanol (2 mL) and tetrahydrofuran (2 mL), was added 2M NaOH (1 mL). After stirring for 1 h at room temperature the solvent was removed in vacuo and the residue acidified with 1M HCl (5 mL), before extraction into ethyl acetate (2×25 mL). The organic solution was dried and the solvents removed in vacuo to afford the title compound as a bright yellow solid (70 mg).

$^1$H NMR (400 MHz; MeOH-d$^4$) δ: 0.98 (3H, t, J 7.5 Hz), 1.43 (2H, m), 1.70 (2H, m), 2.23 (3H, s), 3.74 (2H, t, J 6 Hz), 4.66 (2H, s), 4.88 (2H, s), 6.77 (1H, d, J 8.5 Hz), 7.09 (1H, dd, J 8.5, 1.5 Hz), 7.14 (1H, s), 7.55 (2H, d, J 8.5 Hz), 8.06–8.11 (3H, m), 8.39 (1H, s), CO$_2$H not observed.

LC/MS: m/z 440 [M+H]$^+$, R$_t$ 4.3 min.

EXAMPLE 44

[4-({[6-(4-Chlorophenyl)pyrazin-2-yl][2-(methyloxy)ethyl]amino}methyl)-2-methylphenoxy]acetic acid

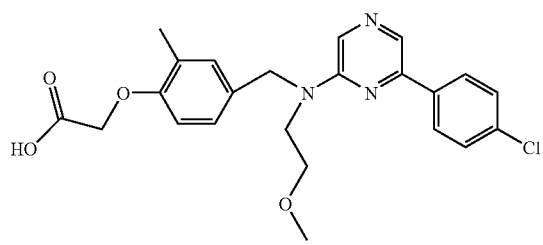

Using ethyl [4-({[6-(4-chlorophenyl)pyrazin-2-yl][2-(methyloxy)ethyl]amino}methyl)-2-methylphenoxy]acetate (81 mg, 0.17 mmol) and the synthetic procedure described for Example 43, to afford the title compound as a bright yellow solid (77 mg).

$^1$H NMR (400 MHz; MeOH-d$^4$) δ: 2.19 (3H, s), 3.30 (3H, s), 3.65 (2H, t, J 5 Hz), 3.91 (2H, t, J 5 Hz), 4.63 (2H, s), 4.92 (2H, s), 6.73 (1H, d, J 8.5 Hz), 7.07 (1H, d, J 8.5 Hz), 7.11 (1H, s), 7.51 (2H, d, J 8.5 Hz), 8.03 (2H, d, J 8 Hz), 8.14 (1H, s), 8.36 (1H, s), CO$_2$H not observed.

LC/MS: m/z 442.1 [M+H]$^+$, R$_t$ 3.7 min.

EXAMPLE 45

{2-Methyl-4-[(propyl{6-[4-(trifluoromethyl)phenyl]pyrazin-2-yl}amino)methyl]phenoxy}acetic acid

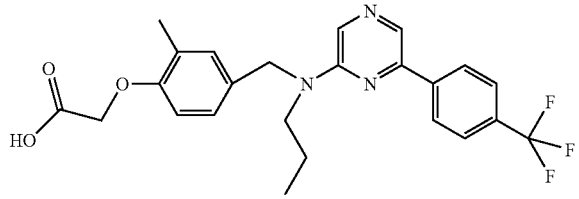

Using ethyl {2-methyl-4-[(propyl{6-[4-(trifluoromethyl)phenyl]pyrazin-2-yl}amino)methyl]phenoxy}acetate (56 mg, 0.12 mmol) and the synthetic procedure described for Example 43, to afford the title compound as a bright yellow solid (50 mg).

$^1$H NMR (400 MHz; MeOH-d$^4$) δ: 1.01 (3H, t, J 7.5 Hz), 1.76 (2H, m), 2.23 (3H, s), 3.72 (2H, t, J 8 Hz), 4.66 (2H, s), 4.90 (2H, s), 6.78 (1H, d, J 8.5 Hz), 7.10 (1H, d, J 8.5 Hz), 7.15 (1H, s), 7.85 (2H, d, J 8 Hz), 8.15 (1H, s), 8.28 (2H, d, J 8 Hz), 8.46 (1H, s), CO$_2$H not observed.

LC/MS: m/z 460.1 [M+H]$^+$, R$_t$ 4.1 min.

EXAMPLE 46

(2-Methyl-4-{[{5-methyl-6-[4-(trifluoromethyl)phenyl]pyrimidin-4-yl}(propyl)amino]methyl}phenoxy)acetic acid

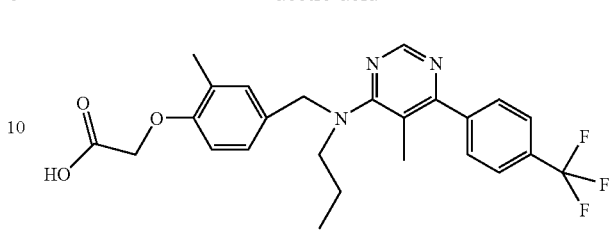

Using ethyl (2-methyl-4-{[{5-methyl-6-[4-(trifluoromethyl)phenyl]pyrimidin-4-yl}(propyl)amino]methyl}phenoxy)acetate (159 mg, 0.32 mmol) and the procedure described for Example 40 to afford the title compound as a white solid (145 mg).

$^1$H NMR (400 MHz; DMSO-d$^6$) δ: 0.87 (3H, t, J 7 Hz), 1.71 (2H, m), 2.15 (3H, s), 2.18 (3H, s), 3.51 (2H, m), 4.69 (2H, s), 4.87 (2H, s), 6.80 (1H, d, J 8.5 Hz), 7.08 (1H, d, J 8.5 Hz), 7.13 (1H, s), 7.88 (2H, d, J 8 Hz), 7.97 (2H, d, J 8 Hz), 8.77 (1H, s), CO$_2$H not observed.

LC/MS: m/z 474.2 [M+H]$^+$, R$_t$ 3.5 min.

EXAMPLE 47

(4-{[[6-(4-Chlorophenyl)-5-methylpyrimidin-4-yl](propyl)amino]methyl}-2-methylphenoxy)acetic acid

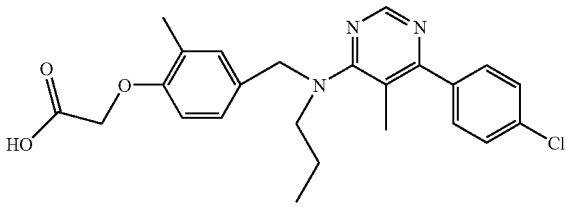

Using ethyl (4-{[[6-(4-chlorophenyl)-5-methylpyrimidin-4-yl](propyl)amino]methyl}-2-methylphenoxy)acetate (116 mg, 0.25 mmol) and the procedure described for Example 40 to afford the title compound as a white solid (56 mg).

$^1$H NMR (400 MHz; DMSO-d$^6$) δ: 0.86 (3H, t, J 7.5 Hz), 1.69 (2H, m), 2.16 (3H, s), 2.18 (3H, s), 3.52 (2H, t, J 7.5 Hz), 4.69 (2H, s), 4.87 (2H, s), 6.79 (1H, d, J 8.5 Hz), 7.08 (1H, d, J 8.5 Hz), 7.12 (1H, s), 7.68 (4H, m), 8.75 (1H, s), CO$_2$H not observed.

LC/MS: m/z 440.1 [M+H]$^+$, R$_t$ 3.3 min.

EXAMPLE 48

(2-Methyl-4-{[[5-methyl-6-(4-methylphenyl)pyrimidin-4-yl](propyl)amino]methyl}phenoxy)acetic acid

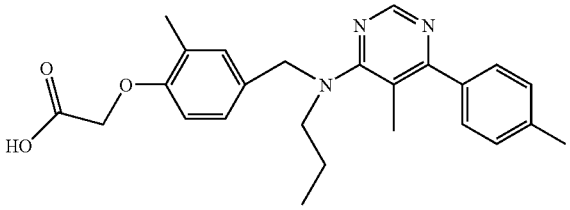

Using ethyl (2-methyl-4-{[[5-methyl-6-(4-methylphenyl)pyrimidin-4-yl](propyl)amino]methyl}phenoxy)acetate (50 mg, 0.11 mmol) and the procedure described for Example 40 to afford the title compound as a white solid (20 mg).

$^1$H NMR (400 MHz; DMSO-d$^6$) δ: 0.87 (3H, t, J 7.5 Hz), 1.71 (2H, m), 2.17 (3H, s), 2.18 (3H, s), 2.41 (3H, s), 3.55 (2H, t, J 7.5 Hz), 4.69 (2H, s), 4.90 (2H, s), 6.80 (1H, d, J 8.5 Hz), 7.08 (1H, dd, J 8.5, 1.5 Hz), 7.13 (1H, s), 7.41 (2H,d, J 8 Hz), 7.55 (2H, d, J 8 Hz), 8.76 (1H, s), CO$_2$H not observed.

LC/MS: m/z 420.2 [M+H]$^+$, R$_t$ 2.9 min.

EXAMPLE 49

(2-Methyl-4-{[{5-methyl-6-[4-(methyloxy)phenyl]pyrimidin-4-yl}(propyl)amino]methyl}phenoxy)acetic acid

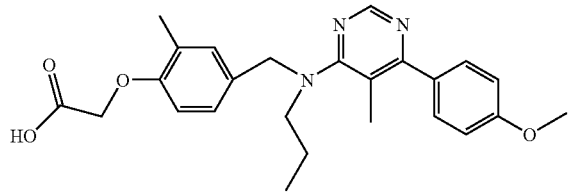

Using Ethyl (2-methyl-4-{[{5-methyl-6-[4-(methyloxy)phenyl]pyrimidin-4-yl}(propyl)amino]methyl}phenoxy)acetate (60 mg, 0.13 mmol) and the procedure described for Example 40 to afford the title compound as a white solid (42 mg).

$^1$H NMR (400 MHz; DMSO-d$^6$) δ: 0.87 (3H, t, J 7.5 Hz), 1.72 (2H, m), 2.18 (3H, s), 2.19 (3H, s), 3.55 (2H, t, J 7.5 Hz), 3.86 (3H, s), 4.69 (2H, s), 4.91 (2H, s), 6.80 (1H, d, J 8 Hz), 7.09 (1H, dd, J 8, 1.5 Hz), 7.12–7.19 (3H, m), 7.62 (2H, d, J 8.5 Hz), 8.75 (1H, s), CO$_2$H not observed.

LC/MS: m/z 436.2 [M+H]$^+$, R$_t$ 2.8 min.

EXAMPLE 50

{4-[(Butyl{6-[4-(trifluoromethyl)phenyl]pyrazin-2-yl}amino)methyl]-2-ethylphenoxy}acetic acid

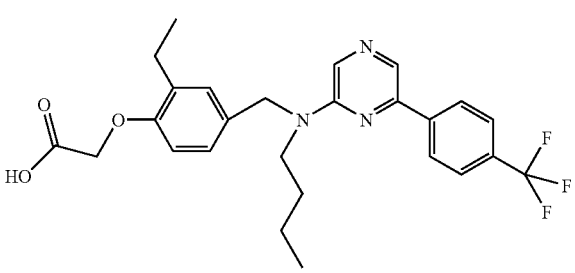

Using ethyl {4-[(butyl{6-[4-(trifluoromethyl)phenyl]pyrazin-2-yl}amino)methyl]-2-ethylphenoxy}acetate (50 mg, 0.10 mmol) and the procedure described for Example 40 to afford the title compound as a bright yellow solid (45 mg).

$^1$H NMR (400 MHz; DMSO-d$^6$) δ: 0.91 (3H, t, J 7.5 Hz), 1.09 (3H, t, J 7.5 Hz), 1.36 (2H, m), 1.60 (2H, m), 2.56 (2H, q, J 7.5 Hz), 3.62 (2H, t, J 7.5 Hz), 4.65 (2H, s), 4.77 (2H, s), 6.76 (1H, d, J 8 Hz), 7.03 (1H, dd, J 8, 2 Hz), 7.13 (1H, s), 7.85 (2H, d, J 8 Hz), 8.13 (1H, s), 8.26 (2H, d, J 8 Hz), 8.46 (1H, s), CO$_2$H not observed.

LC/MS: m/z 488.3 [M+H]$^+$, R$_t$ 4.4 min.

EXAMPLE 51

{2-Ethyl-4-[(2-methyloxyethyl){6-[4-(trifluoromethyl)phenyl]pyrazin-2-yl}amino)methyl]phenoxy}acetic acid

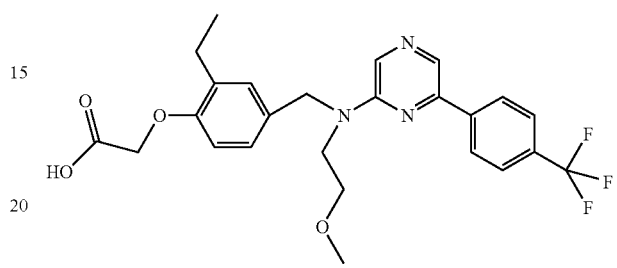

Using ethyl {2-ethyl-4-[(2-methyloxyethyl){6-[4-(trifluoromethyl)phenyl]pyrazin-2-yl}amino)methyl]phenoxy}acetate (48 mg, 0.09 mmol) and the procedure described for Example 40 to afford the title compound as a bright yellow solid (40 mg).

$^1$H NMR (400 MHz; DMSO-d$^6$) δ: 1.09 (3H, t, J 7.5 Hz), 2.56 (2H, q, J 7.5 Hz), 3.26 (3H, s), 3.60 (2H, t, J 5.5 Hz), 3.84 (2H, t, J 5.5 Hz), 4.65 (2H, s), 4.80 (2H, s), 6.76 (1H, d, J 8.5 Hz), 7.03 (1H, dd, J 8.5, 2 Hz), 7.13 (1H, d, J 2 Hz), 7.84 (2H, d, J 8.5 Hz), 8.16 (1H, s), 8.25 (2H, d, J 8.5 Hz), 8.47 (1H, s), CO$_2$H not observed.

LC/MS: m/z 490.3 [M+H]$^+$, R$_t$ 3.9 min.

EXAMPLE 52

[4-({Butyl[5-methyl-6-(4-methylphenyl)pyrimidin-4-yl]amino}methyl)-2-ethylphenoxy]acetic acid

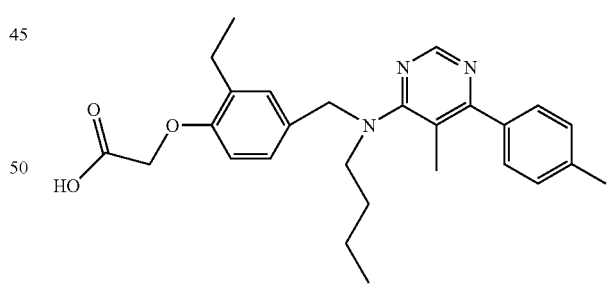

Using ethyl [4-({butyl[5-methyl-6-(4-methylphenyl)pyrimidin-4-yl]amino}methyl)-2-ethylphenoxy]acetate (46 mg, 0.10 mmol) and the procedure described for Example 40 to afford the title compound as a colourless oil (39 mg).

$^1$H NMR (400 MHz; CDCl$_3$) δ: 0.95 (3H, t, J 7.5 Hz), 1.19 (3H, t, J 7.5 Hz), 1.34 (2H, m), 1.70 (2H, m), 2.21 (3H, s), 2.40 (3H, s), 2.69 (2H, q, J 7.5 Hz), 3.65 (2H, t, J 7.5 Hz), 4.66 (2H, s), 4.89 (2H, s), 6.71 (1H, d, J 8 Hz), 6.95 (1H, d, J 8 Hz), 7.03 (1H, s), 7.32 (2H, d, J 8 Hz), 7.46 (2H, d, J 8 Hz), 8.73 (1H, s), CO$_2$H not observed.

LC/MS: m/z 448.3 [M+H]$^+$, R$_t$ 3.2 min

EXAMPLE 53

[4-({Butyl[2-methyl-4'-(trifluoromethyl)-1,1'-biphenyl-3-yl]amino}sulfonyl)-2-methylphenoxy]acetic acid

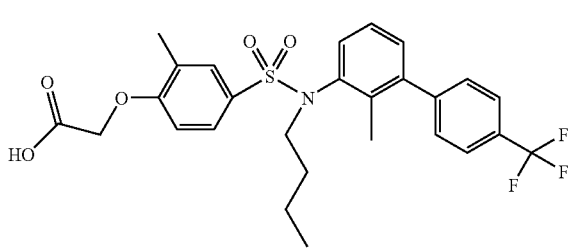

Using ethyl [4-({butyl[2-methyl-4'-(trifluoromethyl)-1,1'-biphenyl-3-yl]amino}sulfonyl)-2-methylphenoxy]acetate (15 mg, 0.03 mmol) and the procedure described for Example 40 to afford the title compound as a colourless oil (13 mg).

$^1$H NMR (400 MHz; CDCl$_3$) δ: 0.87 (3H, t, J 7 Hz), 1.22–1.55 (4H, m), 2.26 (3H, s), 2.33 (3H, s), 3.20 (1H, m), 3.74 (1H, m), 4.80 (2H, s), 6.68 (1H, dd, J 7.5, 1.5 Hz), 6.79 (1H, m), 7.10–7.21 (2H, m), 7.46 (2H, d, J 8 Hz), 7.54 (2H, m), 7.69 (2H, d, J 8 Hz), CO$_2$H not observed.

LC/MS: m/z 536.3 [M+H]$^+$, R$_t$ 4.3 min

EXAMPLE 54

[2-Methyl-4-({(propylsulfonyl)[4'-(trifluoromethyl)-1,1'-biphenyl-3-yl]amino}methyl)pheoxy]acetic acid

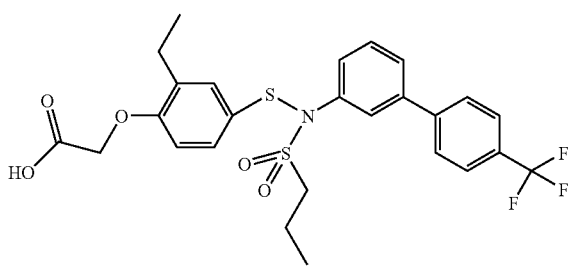

Using ethyl [2-ethyl-4-({(propylsulfonyl)[4'-(trifluoromethyl)-1,1'-biphenyl-3-yl]amino}methyl)pheoxy]acetate (65 mg, 0.12 mmol) and the procedure described for Example 40 to afford the title compound as a yellow solid (56 mg).

$^1$H NMR (400 MHz; CDCl$_3$) δ: 1.06 (3H, t, J 7.5 Hz), 1.12 (3H, t, J7.5 Hz), 1.93 (2H, m), 2.63 (2H, q, J 7.5 Hz), 3.05 (2H, m), 4.65 (2H, s), 4.84 (2H, s), 6.63 (1H, d, J 8.5 Hz), 7.05 (1H, d, J 8.5 Hz), 7.07 (1H, s), 7.29 (1H, m), 7.40–7.50 (3H, m), 7.56 (2H, d, J 8 Hz), 7.68 (2H, d, J 8 Hz), CO$_2$H not observed.

LC/MS: m/z 534.2 [M−H]$^-$, R$_t$ 3.9 min

EXAMPLE 55

[4-({Butyl[6-(4-chlorophenyl)-5-methylpyrimidin-4-yl]amino}methyl)-2-ethylphenoxy]acetic acid

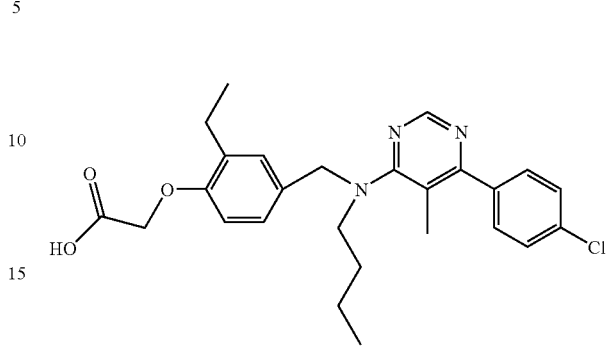

Using ethyl [4-({butyl[6-(4-chlorophenyl)-5-methylpyrimidin-4-yl]amino}methyl)-2-ethylphenoxy]acetate (64 mg, 0.13 mmol) and the procedure described for Example 40 to afford the title compound as a colourless oil (61 mg).

$^1$H NMR (400 MHz; CDCl$_3$) δ: 0.96 (3H, t, J 5.5 Hz), 1.19 (3H, t, J 7.5 Hz), 1.36 (2H, m), 1.72 (2H, m), 2.17 (3H, s), 2.69 (2H, q, J 7.5 Hz), 3.67 (2H, t, J 8 Hz), 4.67 (2H, s), 4.90 (2H, s), 6.71 (1H, d, J 8.5 Hz), 6.93 (1H, d, J 8.5 Hz), 7.02 (1H, s), 7.45–7.55 (4H, m), 8.69 (1H, s), CO$_2$H not observed.

LC/MS: m/z 468.3 [M+H]$^+$, R$_t$ 3.7 min

EXAMPLE 56

{4-[(Butyl{5-methyl-6-[4-(trifluoromethyl)phenyl]pyrimidin-4-yl}amino)methyl]-2-ethylphenoxy}acetic acid

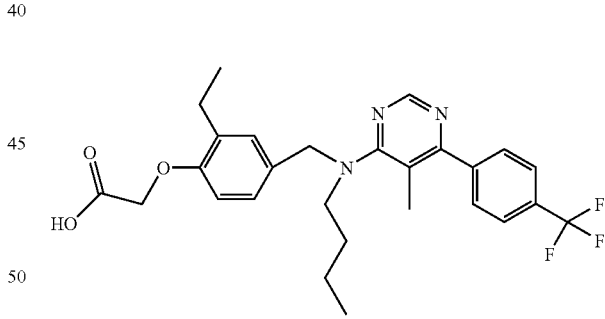

Using ethyl {4-[(butyl{5-methyl-6-[4-(trifluoromethyl)phenyl]pyrimidin-4-yl}amino)methyl]-2-ethylphenoxy}acetate (82 mg, 0.15 mmol) and the procedure described for Example 40 to afford the title compound as a colourless oil (78 mg).

$^1$H NMR (400 MHz; CDCl$_3$) δ: 0.96 (3H, t, J 7.5 Hz), 1.20 (3H, t, J 7.5 Hz), 1.36 (2H, m), 1.73 (2H, m), 2.18 (3H, s), 2.69 (2H, quartet, J 7.5 Hz), 3.67 (2H, t, J 7 Hz), 4.66 (2H, s), 4.90 (2H, s), 6.70 (1H, d, J 8 Hz), 6.94 (1H, d, J 8 Hz), 7.04 (1H, s), 7.70 (2H, d, J 8 Hz), 7.77 (2H, d, J 8 Hz), 8.72 (1H, s), CO$_2$H not observed.

LC/MS: m/z 502.3 [M+H]$^+$, R$_t$ 3.9 min

EXAMPLE 57

{2-Ethyl-4-[([2-(methyloxy)ethyl]{4-[4-(trifluoromethyl)phenyl]pyrimidin-2-yl}amino)methyl]phenoxy}acetic acid

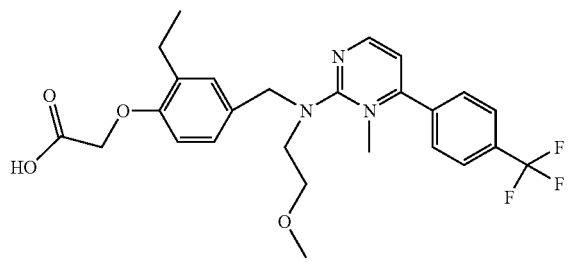

Using ethyl {2-ethyl-4-[([2-(methyloxy)ethyl]{4-[4-(trifluoromethyl)phenyl]pyrimidin-2-yl}amino)methyl]phenoxy}acetate (52 mg, 0.10 mmol) and the procedure described for Example 40 to afford the title compound as a colourless gum (47 mg).

$^1$H NMR (400 MHz; DMSO-d$^6$) δ: 1.09 (3H, br s), 2.58 (2H, m), 3.25 (3H, s), 3.55 (2H, br s), 3.79 (2H, br s), 4.65 (2H, s), 4.88 (2H, s), 6.75 (1H, d, J 8.5 Hz), 6.95–7.2 (2H, m), 7.30 (1H, d, J 5 Hz), 7.88 (2H, J 6.5 Hz), 8.31 (2H, d, J 6.5 Hz), 8.51 (1H, d, J 5 Hz), CO$_2$H not observed.

LC/MS: m/z 490.3 [M+H]$^+$, R$_t$4.1 min

EXAMPLE 58

{2-Methyl-4-[(2-propen-1-yl{6-[4-(trifluoromethyl)phenyl]pyridin-2-yl}amino)methyl]phenoxy}acetic acid

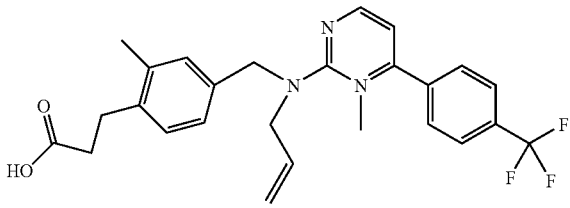

A solution of N-2-propen-1-yl-6-[4-(trifluoromethyl)phenyl]-2-pyridinamine (0.062 g, 0.223 mmol) in anhydrous DMF (3 mL) was cooled to 0° C. under nitrogen and treated with NaH (0.012 g, 0.29 mmol). To this mixture was added ethyl [4-(bromomethyl)-2-methylphenoxy)acetate (0.07 g, 0.245 mmol) and the reaction mixture allowed to attain room temperature and stirred overnight. The reaction was quenched with methanol and concentrated in vacuo. The residue was partitioned between brine/chloroform and the organic extract separated and concentrated. The residue was then treated with further sodium hydride and ethyl [4-(bromomethyl)-2-methylphenoxy)acetate and stirred for 70 h. Work up as before and purification SPE (silica, 10 g) eluting 9:1 cyclohexane:ethyl acetate afforded a colourless oil 75% pure (0.098 g). This material was treated with 2M NaOH (5 mL) in THF (5 mL). After 3 h stirring at room temperature the reaction mixture was acidified 2M HCl and extracted into ethyl acetate. The organic solution was washed with brine, dried (MgSO$_4$) and evaporated. Purifciation by autoprep HPLC afforded the title compound as a white solid (14 mg).

$^1$H NMR (400 MHz; MeOH-d$^4$) δ: 2.25 (3H, s), 4.30 (2H, d, J 5.5 Hz), 4.68 (2H, s), 4.82 (2H, s), 5.22 (1H, s), 5.26 (1H, d, J 4.5 Hz), 5.90–5.99 (1H, m), 6.78 (2H, d, J 8.5 Hz), 7.10 (1H, m), 7.14 (1H, br s), 7.20 (1H, d, J 7 Hz), 7.69 (1H, t, J 8.5 Hz), 7.75 (2H, d, J 8.5 Hz), 8.09 (2H, d, J 8.5 Hz), CO$_2$H not observed.

LC/MS: m/z 457.2 [M+H]$^+$, R$_t$4.3 min.

The following intermediates and ligands were prepared for the binding and transfection assays described below:

(i) 2-{2-Methyl-4-[({4-methyl-2-[4-(trifluoromethyl)phenyl]-1,3-thiazol-5-yl}methyl)sulfanyl]phenoxy}acetic acid This compound was used as a PPAR delta reference in the transfection assays described below and was prepared according to the method reported in WO200100603-A1

(ii) 2-Methyl-2-[4-{[(4-methyl-2-[4-trifluoromethylphenyl]-thiazol-5-yl carbonyl)amino]methyl}-phenoxy] propionic acid This compound was used as a PPAR alpha reference in the transfection assay described below and was prepared according to method reported in WO200140207-A1

(iii) 5-{4-[2-(Methyl-pyridin-2-yl-amino)-ethoxy]-benzyl}-thiazolidine-2,4-dione This compound was used as a PPAR gamma reference in the transfection assay described below and was prepared according to method reported in J. Med. Chem. 1994, 37(23), 3977

Binding Assay:

Compounds were tested for their ability to bind to hPPAR gamma, hPPAR alpha or hPPAR delta using a Scintillation Proximity Assay (SPA). The PPAR ligand binding domain (LBD) was expressed in E. coli as polyHis tagged fusion proteins and purified. The LBD was then labelled with biotin and immobilised on streptavidin-modified scintillation proximity beads. The beads were then incubated with a constant amount of the appropriate radioligand (3H-BRL 49653 for PPAR gamma, and labelled GW 2433 (see Brown, P. J et al. Chem. Biol., 4, 909–918 (1997). For the structure and synthesis of this ligand) for PPAR alpha and PPAR delta) and variable concentrations of test compound, and after equilibration the radioactivity bound to the beads was measured by a scintillation counter. For each compound tested, plots of ligand concentration vs. CPM of radioligand bound were constructed and apparent Ki values were estimated from nonlinear least squares fit of the data assuming simple competitive binding. The details of this assay have been reported elsewhere (see, Blanchard, S. G. et. al. Development of a Scintillation Proximity Assay for Peroxisome Proliferator Activated Receptor gamma Ligand Binding Domain. Anal. Biochem., 257,112–119 (1998)).

Transfection Assay:

Compounds were screened for functional potency in transient transfection assays in CV-1 cells for their ability to activate the PPAR subtypes (transactivation assay). A previously established chimeric receptor system was utilized to allow comparison of the relative transcriptional activity of the receptor subtypes on the same target gene and to prevent endogenous receptor activation from complicating the interpretation of results. See, for example, Lehmann, J. M.; Moore, L. B.; Smith-Oliver, T. A.; Wilkison, W. O.; Willson, T. M.; Kliewer, S. A., An antidiabetic thiazolidinedione is a high affinity ligand for peroxisome proliferator-activated receptor gamma (PPARgamma), J. Biol. Chem., 270, 12953–6 (1995). The ligand binding domains for murine and human PPAR alpha, PPAR gamma, and PPAR delta were each fused to the yeast transcription factor GAL4 DNA binding domain. CV-1 cells were transiently transfected with expression vectors for the respective PPAR chimera along with a reporter construct containing five copies of the GAL4 DNA binding site driving expression of secreted placental alkaline phosphatase (SPAP) and beta-galactosidase. After 16 h, the medium was exchanged to DME medium supplemented with 10% delipidated fetal calf serum and the test compound at the appropriate concentration. After an additional 24 h, cell extracts were prepared and assayed for alkaline phosphatase and β-galactosidase activity. Alkaline phosphatase activity was corrected for transfection efficiency using the beta-galactosidase activity as an internal standard (see, for example, Kliewer, S. A., et. al. Cell 83, 813–819 (1995)). Rosiglitazone (BRL 49653) was used as a positive control in the hPPAR gamma assay. The positive control in the hPPAR alpha assays was 2-methyl-2-[4-{[(4-methyl-2-[4-trifluoromethylphenyl]-thiazol-5-yl-carbonyl)amino]methyl}-phenoxy]propionic acid. The positive control for PPAR delta assays was 2-{2-methyl-4-[({4-methyl-2{trifluoromethyl)phenyl]-1,3-thiazol-5-yl}methyl)sulfanyl]phenoxy}acetic acid.

All the above acid examples showed at least 50% activation of hPPARδ relative to the positive control at concentrations of $10^{-7}$M or less.

The invention claimed is:

1. A compound of formula (I) or a pharmaceutically acceptable salt or hydrolysable ester thereof,

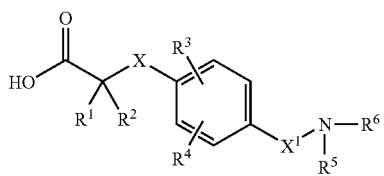

Wherein:
$R^1$ and $R^2$ are independently hydrogen or $C_{1-3}$ alkyl;
X represents a bond, $CH_2$ or O;
one of $R^3$ and $R^4$ is H and the other is $C_{1-3}$ alkyl;
$X^1$ is $CH_2$, $SO_2$, or CO;
$R^5$ is
—$C_{1-6}$ alkyl wherein said —$C_{1-6}$alkyl is optionally substituted by $C_{1-6}$alkoxy or $C_{1-6}$alkylthio,
—$C_{2-6}$ alkenyl,
—$C_{0-6}$ alkyl phenyl wherein said phenyl is optionally substituted by one or more $CF_3$, halogen, $C_{1-3}$ alkyl, or $C_{1-3}$ alkoxy,
—$COC_{1-6}$ alkyl, or $SO_2C_{1-6}$ alkyl;
$R^6$ is phenyl or a 6 membered heteroaryl group containing 1, 2 or 3 N atoms wherein the phenyl or heteroaryl group is optionally substituted with 1, 2 or 3 moieties selected from the group consisting of $C_{1-6}$ alkyl, halogen, —$OC_{1-6}$ alkyl, —$SO_2C_{1-3}$ alkyl, and phenyl optionally substituted by one or more groups selected from halogen, $CF_3$, $C_{1-3}$ alkyl, $OC_{1-3}$ alkyl, acetyl, CN.

2. A compound according to claim 1 wherein each $R^1$ and $R^2$ is independently H or methyl.

3. A compound according to claim 2 wherein $R^1$ and $R^2$ are both H or both methyl.

4. A compound according to claim 3 wherein $R^1$ and $R^2$ are both H.

5. A compound according to claim 1 wherein X is O.

6. A compound according to claim 1 wherein the $C_{1-3}$ alkyl group of $R^3$ or $R^4$ is positioned, on the phenyl on which it is a substituent, ortho to the point of attachment of the depicted phenyl to the X moiety.

7. A compound according to claim 1 wherein $X^1$ is $CH_2$.

8. A compound according to claim 1 wherein $R^5$ is butyl or methoxyethyl.

9. A compound according to claim 1 wherein $R^6$ is phenyl or a 6-membered heterocycle selected from pyrimidine, pyridine, pyridazine and pyrazine each of which phenyl or heterocycle is optionally substituted by a $C_{1-3}$ alkyl substituent, and each phenyl or heterocycle is substituted by a phenyl which is optionally substituted by one or more $CF_3$, $C_{1-3}$ alkyl, halogen, or CN.

10. A compound according to claim 9 wherein the phenyl which is optionally substituted by one or more $CF_3$, $C_{1-3}$ alkyl, halogen, CN is attached to the $R^6$ substituent at the position meta to the point of attachment of $R^6$ to the depicted N.

11. A compound according to claim 1 selected from:
2-Methyl-2-{2-methyl-4-[([4-(trifluoromethyl)benzyl]{6-[4-(trifluoromethyl)phenyl]pyridin-2-yl}amino)methyl]phenoxy}propanoic acid;
2-{4-[(Butyl{6-[4-(trifluoromethyl)phenyl]pyridin-2-yl}amino) methyl]-2-methylphenoxy}-2-methylpropanoic acid;
{4-[(Butyl{6-[4-(trifluoromethyl)phenyl]pyridin-2-yl}amino)methyl]-2-methylphenoxy}acetic acid;
[4-({Butyl[4'-(trifluoromethyl)-1,1'-biphenyl-3-yl]amino}methyl)-2-methylphenoxy]acetic acid;
[4-({(2-Methoxyethyl)[4'-(trifluoromethyl)-1,1'-biphenyl-3-yl]amino}methyl)-2-methylphenoxy]acetic acid;
[2-Methyl-4-{pentyl {4'-(trifluoromethyl)-1,1'-benphenyl-3-yl]amino}methyl)phenoxy]acetic acid;
[4-({(2-Cyclopropylethyl)[4'-trifluoromethyl)-1,1'-biphenyl-3yl]amino}methyl)-2-methylphenoxy]acetic acid;
[2-Methyl-4-({propyl[4'-(trifluoromethyl)-1,1'-biphenyl-3-yl]amino}methyl)phenoxy]acetic acid;
[2-Methyl-4-({[2-(methylthio)ethyl][4'-(trifluoromethyl)-1,1'-biphenyl-3-yl]amino}methyl)phenoxy]acetic acid;
[4-({Butyl[2-methyl-4'-(trifluoromethyl)-1,1'-biphenyl-3-yl]amino}methyl)-2-methylphenoxy]acetic acid;
[4-({(2-Methoxyethyl)[2-methyl-4'-(trifluoromethyl)-1,1'-biphenyl-3-yl]amino}methyl)-2-methylphenoxy]acetic acid;
[4-({Butyryl[4'-(trifluoromethyl)-1,1'-biphenyl-3-yl]amino}methyl)-2-methylphenoxy]acetic acid;
[2-Methyl-4-({(propylsulfonyl)[4'-(trifluoromethyl)-1,1'-biphenyl-3-yl]amino}methyl)phenoxy]acetic acid;
[4-({Butyl[4'-(trifluoromethyl)-1,1'-biphenyl-3-yl]amino}sulfonyl)-2-methylphenoxy]acetic acid;
[2-Methyl-4-({pentyl[4'-(trifluoromethyl)-1,1'-biphenyl-3-yl]amino}sulfonyl)phenoxy]acetic acid;
[4-({(2-Cyclopropylethyl)[4'-(trifluoromethyl)-1,1'-biphenyl-3-yl]amino}sulfonyl)-2-methylphenoxy]acetic acid;
{4-[(Butyl{4-[4-(trifluoromethyl)phenyl]pyrimidin-2-yl}amino) methyl]-2-methylphenoxy}acetic acid;
[4-({Butyl[4-(4-chlorophenyl)pyrimidin-2-yl]amino}methyl)-2-methylphenoxy]acetic acid;
{4-[((2-Methoxyethyl){4-[4-(trifluoromethyl)phenyl]pyrimidin-2-yl}amino)methyl]-2-methylphenoxy}acetic acid;
(4-{[[4-(4-Chlorophenyl)pyrimidin-2-yl](2-methoxyethyl)amino] methyl}-2-methylphenoxy)acetic acid;

{2-Methyl-4-[(propyl{4-[4-(trifluoromethyl)phenyl]pyrimidin-2-yl}amino)methyl]phenoxy}acetic acid;
{4-[(Butyl{6-[4-(trifluoromethyl)phenyl]pyrazin-2-yl}amino)methyl]-2-methylphenoxy}acetic acid;
[4-({Butyl[6-(4-methylphenyl)pyrazin-2-yl]amino}methyl)-2-methylphenoxy]acetic acid;
{4-[((2-Methoxyethyl){6-[4-(trifluoromethyl)phenyl]pyrazin-2-yl}amino)methyl]-2-methylphenoxy}acetic acid;
(4-{[Butyl(2,4'-dimethyl-1,1'-biphenyl-3-yl)amino]methyl}-2-methylphenoxy)acetic acid;
(4-{[Butyl(4'-fluoro-2-methyl-1,1'-biphenyl-3-yl)amino]methyl}-2-methylphenoxy)acetic acid;
(4-{[Butyl(4'-cyano-2-methyl-1,1'-biphenyl-3-yl)amino]methyl}-2-methylphenoxy)acetic acid;
(4-{[Butyl(4'-methoxy-2-methyl-1,1'-biphenyl-3-yl)amino]methyl}-2-methylphenoxy)acetic acid;
(4-([Butyl(4'-chloro-2-methyl-1,1'-biphenyl-3-yl)amino]methyl)₂-methylphenoxy)acetic acid;
(4-{[(4'-Chloro-2-methyl-1,1'-biphenyl-3-yl)(2-methoxyethyl)amino]methyl}-2-methylphenoxy)acetic acid;
(4-{[(2,4'-Dimethyl-1,1'-biphenyl-3-yl)(2-methoxyethyl)amino]methyl}-2-methylphenoxy)acetic acid;
(4-{[(2-Methoxyethyl)(4'-methoxy-2-methyl-1,1'-biphenyl-3-yl)amino]methyl}-2-methylphenoxy)acetic acid;
(2-Methyl-4-{[[2-methyl-4'-(trifluoromethyl)-1,1'-biphenyl-3-yl](propyl)amino]methyl}phenoxy)acetic acid;
(4-{[(4'-Chloro-2-methyl-1,1'-biphenyl-3-yl)(propyl)amino]methyl}-2-methylphenoxy)acetic acid;
(4-{[(2,4'-Dimethyl-1,1'-biphenyl-3-yl)(propyl)amino]methyl}-2-methylphenoxy)acetic acid;
(4-{[(4'-Fluoro-2-methyl-1,1'-biphenyl-3-yl)(propyl)amino]methyl}-2-methylphenoxy)acetic acid;
(4-{[(4'-Cyano-2-methyl-1,1'-biphenyl-3-yl)(propyl)amino]methyl}-2-methylphenoxy)acetic acid;
(4-{[(4'-Methoxy-2-methyl-1,1'-biphenyl-3-yl)(propyl)amino]methyl}-2-methylphenoxy)acetic acid;
{4-[(Butyl(5-methyl-6-[4-(trifluoromethyl)phenyl]pyrimidin-4-ylamino)methyl]-2-methylphenoxy}acetic acid;
[4-({Butyl[6-(4-methoxyphenyl)-5-methylpyrimidin-4-yl]amino}methyl)-2-methylphenoxy]acetic acid;
[4-({Butyl[5-methyl-6-(4-methylphenyl)pyrimidin-4-yl]amino}methyl)-2-methylphenoxy]acetic acid;
[4-({Butyl[6-(4-chlorophenyl)-5-methylpyrimidin-4-yl]amino}methyl)-2-methylphenoxy]acetic acid;
[4-({Butyl[6-(4-chlorophenyl)-2-pyrazin-2-yl]amino}methyl)-2-methylphenoxy]acetic acid;
[4-({[6-(4-Chlorophenyl)pyrazin-2-yl][2-(methyloxy)ethyl]amino}methyl)-2-methylphenoxy]acetic acid;
{2-Methyl-4-[(propyl{6-[4-(trifluoromethyl)phenyl]pyrazin-2-yl}amino)methyl]phenoxy}acetic acid;
(2-Methyl-4-{[{5-methyl-6-[4-(trifluoromethyl)phenyl]pyrimidin-4-yl}(propyl)amino]methyl}phenoxy)acetic acid;
(4-{[[6-(4-Chlorophenyl)-5-methylpyrimidin-4-yl](propyl)amino]methyl}-2-methylphenoxy)acetic acid;
(2-Methyl-4-{[[5-methyl-6-(4-methylphenyl)pyrimidin-4-yl](propyl)amino]methyl}phenoxy)acetic acid;
(2-Methyl-4-{[{5-methyl-6-[4-(methyloxy)phenyl]pyrimidin-4-yl}(propyl)amino]methyl}phenoxy)acetic acid;
{4-[(Butyl{6-[4-(trifluoromethyl)phenyl]pyrazin-2-yl}amino)methyl]-2-ethylphenoxy}acetic acid;
{2-Ethyl-4-[(2-methyloxyethyl){6-[4-(trifluoromethyl)phenyl]pyrazin-2-yl}amino)methyl]phenoxy}acetic acid;
[4-({Butyl[5-methyl-6-(4-methylphenyl)pyrimidin-4-yl]amino}methyl)-2-ethylphenoxy]acetic acid;
[4-({Butyl[2-methyl-4'-(trifluoromethyl)-1,1'-biphenyl-3-yl]amino}sulfonyl)-2-methylphenoxy]acetic acid;
[2-Methyl-4-({(propylsulfonyl)[4'-(trifluoromethyl)-1,1'-biphenyl-3-yl]amino}methyl)pheoxy]acetic acid;
[4-({Butyl[6-(4-chlorophenyl)-5-methylpyrimidin-4-yl]amino}methyl)-2-ethylphenoxy]acetic acid;
{4-[(Butyl{5-methyl-6-[4-(trifluoromethyl)phenyl]pyrimidin-4-yl}amino)methyl]-2-ethylphenoxy}acetic acid;
{2-Ethyl-4-[([2-(methyloxy)ethyl]{4-[4-(trifluoromethyl)phenyl]pyrimidin-2-yl}amino)methyl]phenoxy}acetic acid; and
{2-Methyl-4-[(2-propen-1-yl{6-[4-(trifluoromethyl)phenyl]pyridin-2-yl}amino)methyl]phenoxy}acetic acid.

12. A pharmaceutical composition comprising a compound according to claim 1 and a pharmaceutically acceptable diluent or carrier.

* * * * *

UNITED STATES PATENT AND TRADEMARK OFFICE
CERTIFICATE OF CORRECTION

PATENT NO. : 7,199,239 B2  
APPLICATION NO. : 10/518778  
DATED : April 3, 2007  
INVENTOR(S) : Beswick et al.

Page 1 of 1

It is certified that error appears in the above-identified patent and that said Letters Patent is hereby corrected as shown below:

On the Title page:

A citation in Item (56) should read as follows:

(56) References Cited  
    FOREIGN PATENT DOCUMENTS

FR        2273518   1/1976  
    WO   WO 00/23407  4/2000  
  -- EP       1067109   1/2001 --  
    WO   WO 02/28821  4/2002

In the Claims:

Claim 10 in Column 88 (Line 18) should read as follows:

-- alkyl, halogen or CN is attached to the $R^6$ substituent at the --

Claim 11 in Column 89 (Lines 18-19) should read as follows:

-- (4-([Butyl(4'-chloro-2-methyl-1,1'-biphenyl-3-yl)amino]methyl)-2-methylphenoxy)acetic acid; --

Signed and Sealed this

Twentieth Day of November, 2007

JON W. DUDAS  
*Director of the United States Patent and Trademark Office*